US010466249B2

(12) United States Patent
Verdine et al.

(10) Patent No.: US 10,466,249 B2
(45) Date of Patent: Nov. 5, 2019

(54) METHODS AND REAGENTS FOR ANALYZING PROTEIN-PROTEIN INTERFACES

(71) Applicant: Warp Drive Bio, Inc., Cambridge, MA (US)

(72) Inventors: Gregory L. Verdine, Boston, MA (US); M. James Nichols, Charlestown, MA (US); Sharon A. Townson, Cambridge, MA (US); Uddhav Kumar Shigdel, Cambridge, MA (US); Seung-Joo Lee, Cambridge, MA (US); Dylan T. Stiles, Chestnut Hill, MA (US); Neville J. Anthony, Northborough, MA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 15/974,923

(22) Filed: May 9, 2018

(65) Prior Publication Data

US 2018/0259535 A1 Sep. 13, 2018

Related U.S. Application Data

(63) Continuation of application No. 15/282,430, filed on Sep. 30, 2016, now Pat. No. 9,989,535.

(60) Provisional application No. 62/235,896, filed on Oct. 1, 2015.

(51) Int. Cl.
| | |
|---|---|
| *G01N 33/68* | (2006.01) |
| *C07K 1/08* | (2006.01) |
| *C07K 5/083* | (2006.01) |
| *C07K 7/64* | (2006.01) |
| *C07K 1/13* | (2006.01) |
| *C07K 5/02* | (2006.01) |
| *C12Q 1/533* | (2006.01) |
| *G01N 33/566* | (2006.01) |
| *C07K 5/062* | (2006.01) |

(52) U.S. Cl.
CPC ......... *G01N 33/6845* (2013.01); *C07K 1/086* (2013.01); *C07K 1/13* (2013.01); *C07K 5/0215* (2013.01); *C07K 5/06034* (2013.01); *C07K 5/0808* (2013.01); *C07K 7/64* (2013.01); *C07K 7/645* (2013.01); *C12Q 1/533* (2013.01); *G01N 33/566* (2013.01); *G01N 2333/82* (2013.01); *G01N 2333/90209* (2013.01); *G01N 2410/08* (2013.01); *G01N 2500/02* (2013.01)

(58) Field of Classification Search
CPC .................................................. C07K 5/0215
See application file for complete search history.

(56) References Cited

U.S. PATENT DOCUMENTS

| | | |
|---|---|---|
| 6,183,965 B1 | 2/2001 | Verdine et al. |
| 6,372,712 B1 | 4/2002 | Briesewitz et al. |
| 6,713,607 B2 | 3/2004 | Caggiano et al. |
| 7,220,552 B1 | 5/2007 | Crabtree et al. |
| 8,664,186 B2 | 3/2014 | Aigle et al. |
| 9,250,237 B2 | 2/2016 | Liu et al. |
| 9,428,845 B1 | 8/2016 | Verdine et al. |
| 10,203,323 B2 | 2/2019 | Verdine et al. |
| 2002/0110874 A1 | 8/2002 | Khosla et al. |
| 2002/0147133 A1 | 10/2002 | Briesewitz et al. |
| 2003/0153053 A1 | 8/2003 | Reid |
| 2003/0175901 A1 | 9/2003 | Reeves et al. |
| 2004/0087496 A1 | 5/2004 | Kim et al. |
| 2005/0233431 A1 | 10/2005 | Ashley et al. |
| 2007/0203168 A1 | 8/2007 | Zhao |
| 2011/0117606 A1 | 5/2011 | Jorgensen et al. |
| 2012/0208720 A1 | 8/2012 | Kashiwagi et al. |
| 2012/0270800 A1 | 10/2012 | Verdine et al. |
| 2013/0072439 A1 | 3/2013 | Nash et al. |
| 2014/0073581 A1 | 3/2014 | Liu et al. |
| 2015/0250896 A1 | 9/2015 | Zhao |
| 2015/0307855 A1 | 10/2015 | Yuzawa et al. |
| 2016/0341719 A1 | 11/2016 | Verdine et al. |

FOREIGN PATENT DOCUMENTS

| | | | |
|---|---|---|---|
| EP | 393934 | * 10/1990 | ............... C07K 5/10 |
| EP | 0562853 A1 | 9/1993 | |
| EP | 1079859 B1 | 7/2010 | |
| WO | WO-86/02080 A1 | 4/1986 | |
| WO | WO-95/32294 A1 | 11/1995 | |
| WO | WO-96/020216 A1 | 7/1996 | |
| WO | WO-98/07743 A1 | 2/1998 | |
| WO | WO-99/61055 A1 | 12/1999 | |
| WO | WO-01/36460 A2 | 5/2001 | |
| WO | WO-01/36612 A1 | 5/2001 | |

(Continued)

OTHER PUBLICATIONS

Archibald. Bioorganic and Medicinal Chemistry, 2000, 10, 993-995.*

(Continued)

*Primary Examiner* — Noble E Jarrell

(74) *Attorney, Agent, or Firm* — Clark & Elbing LLP

(57) ABSTRACT

The present disclosure provides methods and reagents useful for analyzing protein-protein interfaces such as interfaces between a presenter protein (e.g., a member of the FKBP family, a member of the cyclophilin family, or PIN1) and a target protein. In some embodiments, the target and/or presenter proteins are intracellular proteins. In some embodiments, the target and/or presenter proteins are mammalian proteins.

2 Claims, 22 Drawing Sheets

Specification includes a Sequence Listing.

(56) References Cited

FOREIGN PATENT DOCUMENTS

| WO | 2001090070 | * | 11/2001 | ........... C07D 211/60 |
|---|---|---|---|---|
| WO | WO-2008/069824 A2 | | 6/2008 | |
| WO | WO-2010/031185 A1 | | 3/2010 | |
| WO | WO-2010/034243 A1 | | 4/2010 | |
| WO | WO-2010/088573 A1 | | 8/2010 | |
| WO | WO-2012/075048 A2 | | 6/2012 | |
| WO | WO-2012/174489 A2 | | 12/2012 | |
| WO | WO-2014/187959 A2 | | 11/2014 | |
| WO | WO-2015/132784 A1 | | 9/2015 | |
| WO | WO-2018/081592 A2 | | 5/2018 | |

OTHER PUBLICATIONS

Bhuyan. Organic and Biomolecular Chemistry, 2012, 10, 2237-47.*
Chevalier. Tetrahedron letters, 2014, 55, 6759-63.*
Kuramochi. Bioconjugate Chemistry, 2008, 19, 2417-26.*
Takakusagi. Bioorganic and Medicinal Chemistry, 2008, 16, 9837-46.*
STN record of WO 2014009774, available online Jan. 16, 2014.*
STN record of WO 9812217, available online Mar. 26, 1998.*
Wu. Journal of Medicinal Chemistry, 2002, 45(16), 3558-68 (Year: 2002).*
Bender. Journal of Organic Chemistry, 1978, 45(16), 3354-62 (Year: 1978).*
U.S. Appl. No. 61/418,038, Johns Hopkins University.
"Substructure Search Report on Specifically Substituted Macrocycles—Substances Only", prepared by Science IP, dated Dec. 17, 2014 (6177 pages).
Andrei et al., "Stabilization of protein-protein interactions in drug discovery," Expert Opin Drug Discov. 12(9):925-40 (2017) (17 pages).
Antunes et al., "A mutational analysis defines Vibrio fischeri LuxR binding sites," J Bacteriol. 190(13):4392-7 (2008).
Banaszynski et al., "Characterization of the FKBP.rapamycin.FRB ternary complex," J Am Chem Soc. 127(13):4715-21 (2005).
Bayle et al., "Rapamycin analogs with differential binding specificity permit orthogonal control of protein activity," Chem Biol. 13(1):99-107 (2006).
Blodgett et al., "Unusual transformations in the biosynthesis of the antibiotic phosphinothricin tripeptide," Nat Chem Biol. 3(8):480-5 (2007).
Briesewitz et al., "Affinity modulation of small-molecule ligands by borrowing endogenous protein surfaces," Proc Natl Acad Sci U.S.A. 96(5):1953-8 (1999).
Bruce, "In vivo protein complex topologies: sights through a cross-linking lens," Proteomics. 12(10):1565-75 (2012).
Burgess et al., "Controlled translocation of palladium(II) within a 22 ring atom macrocyclic ligand," Dalton Trans. 43(45):17006-16 (2014).
Chaurasia et al., "Molecular insights into the stabilization of protein-protein interactions with small molecule: The FKBP12-rapamycin-FRB case study," Chem Phys Lett. 587:68-74 (2013).
Che et al., "Inducing protein-protein interactions with molecular glues," Bioorganic & Medicinal Chemistry Letters (2018).
Findlay et al., "The structure of demethoxyrapamycin," Can J Chem. 60:2046-7 (1982).
Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).
Horton et al., "Engineering hybrid genes without the use of restriction enzymes: gene splicing by overlap extension," Gene. 77(1):61-8 (1989).
Hosted et al., "Use of rpsL for dominance selection and gene replacement in Streptomyces roseosporus,"J Bacteriol. 179(1): 180-6 (1997).

Huang et al., "Enhanced rapamycin production in Streptomyces hygroscopicus by integrative expression of aveR, a LAL family transcriptional regulator," World J Microbiol Biotechnol. 27:2103-9 (2011).
Hubler et al., "Synthetic routes to NEtXaa4-cyclosporin a derivatives as potential anti-HIV I drugs," Tetrahedron Lett. 41:7193-6 (2000).
International Search Report and Written Opinion for International Application No. PCT/US2016/054691, dated Feb. 15, 2017 (28 pages).
Ishizawa et al., "TRAP display: a high-speed selection method for the generation of functional polypeptides," J Am Chem. 135(14):5433-40 (2013).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Laureti et al., "Identification of a bioactive 51-membered macrolide complex by activation of a silent polyketide synthase in Streptomyces ambofaciens," Proc Natl Acad Sci USA. 108(15):6258-63 (2011).
Leskiw et al., "TTA codons in some genes prevent their expression in a class of developmental, antibiotic-negative, Streptomyces mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012).
Ochi et al., "New strategies for drug discovery: activation of silent or weakly expressed microbial gene clusters," Appl Microbiol Biotechnol. 97(1):87-98 (2013).
Papageorgiou et al., "Improved binding affinity for cyclophilin a by a cyclosporin derivative singly modified at its effector domain," J Med Chem. 37(22):3674-6 (1994).
Pfeifer et al., "Biosynthesis of complex polyketides in a metabolically engineered strain of E. coli," Science 291(5509):1790-2 (2001).
Ranganathan et al., "Knowledge-based design of bimodular and trimodular polyketide synthases based on domain and module swaps: a route to simple statin analogues," Chem Biol. 6(10):731-41 (1999).
Ruan et al., "Binding of rapamycin analogs to calcium channels and FKBP52 contributes to their neuroprotective activities," Proc Natl Acad Sci U.S.A. 105(1):33-8 (2008).
Schwecke et al., "The biosynthetic gene cluster for the polyketide immunosuppressant rapamycin," Proc Natl Acad Sci USA. 92(17):7839-43 (1995).
Sieber et al., "Novel inhibitors of the calcineurin/NFATc hub—alternatives to CsA and FK506?," Cell Commun Signal. 7:25 (2009) (19 pages).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
UniProtKB Accession No. A0A061A618, Sep. 3, 2014, available <http://www.uniprot.org/uniprot/A0A061A618>, (12 pages).
UniProtKB Accession No. Q54296, Nov. 1, 1996, available <http://www.uniprot.org/uniprot/Q54296>, (12 pages).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22:816-28 (1983).
Wilson et al., "Comparative X-ray structures of the major binding protein for the immunosuppressant FK506 (tacrolimus) in unliganded form and in complex with FK506 and rapamycin," Acta Cryst. D51:511-21 (1995).

(56) References Cited

OTHER PUBLICATIONS

Wright et al., "Multivalent binding in the design of bioactive compounds," Curr Org Chem. 5(11):1107-31 (2001).

Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).

Wu et al., "Inhibition of ras-effector interactions by cyclic peptides," Med Chem Commun. 4(2):378-82 (2013).

"SMART™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).

Benjamin et al., "Rapamycin passes the torch: a new generation of mTOR inhibitors," Nat Rev Drug Discov. 10(11):868-80 (2011).

Extended European Search Report for European Application No. 16735480.2, dated Aug. 8, 2018 (9 pages).

Kendrew et al., "Recombinant strains for the enhanced production of bioengineered rapalogs," Metab Eng. 15:167-73 (2013).

Revill et al., "Genetically engineered analogs of ascomycin for nerve regeneration," J Pharmacol Exp Ther. 302(3):1278-85 (2002).

UniProtKB Accession No. Q54297, Nov. 1, 1996, available <https://www.uniprot.org/uniprot/Q54297.txt>, (3 pages).

Allain et al., "Cyclophilin B mediates cyclosporin A incorporation in human blood T-lymphocytes through the specific binding of complexed drug to the cell surface," Biochem J. 317 (Pt 2):565-70 (1996).

Wang et al., "Thermodynamic analysis of cyclosporin a binding to cyclophilin a in a lung tumor tissue lysate," Anal Chem. 76(15):4343-8 (2004).

Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).

International Search Report and Written Opinion for International Application No. PCT/US2016/012631, dated Mar. 16, 2016 (13 pages).

Kuhn et al., "Synthesis of Functional Ras Lipoproteins and Fluorescent Derivatives," J Am Chem Soc. 123(6):1023-35 (2001).

Quesniaux et al., "Cyclophilin binds to the region of cyclosporine involved in its immunosuppressive activity," Eur J Immunol. 17(9):1359-65 (1987).

Quesniaux et al., "Study of the conformation of cyclosporine in aqueous medium by means of monoclonal antibodies," Int J Pept Protein Res. 31(2):173-85 (1988).

* cited by examiner

FIG. 4
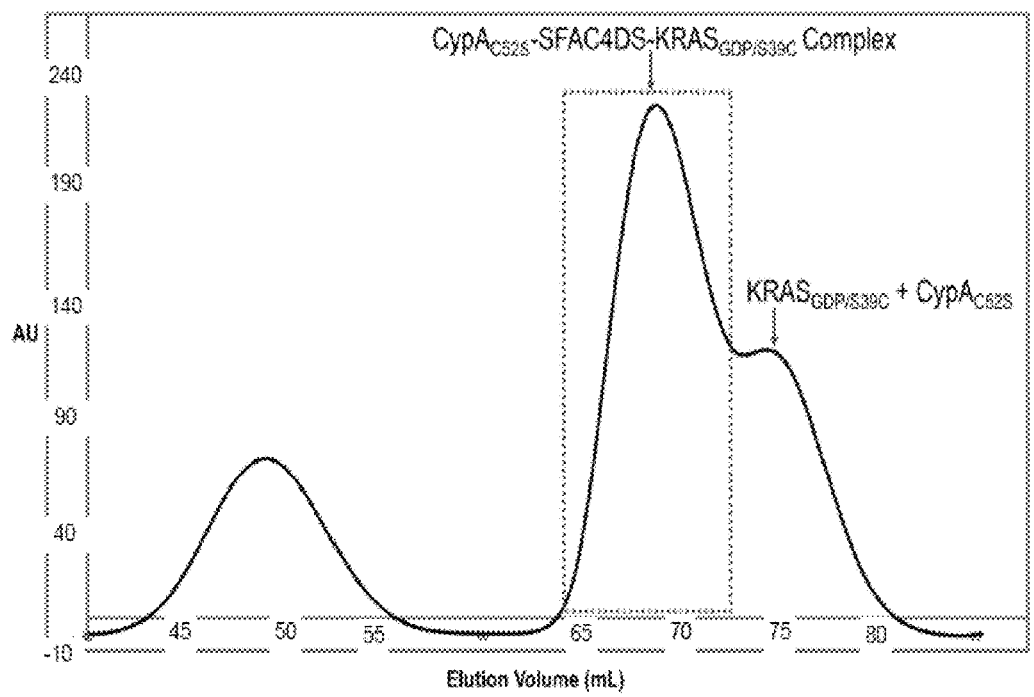
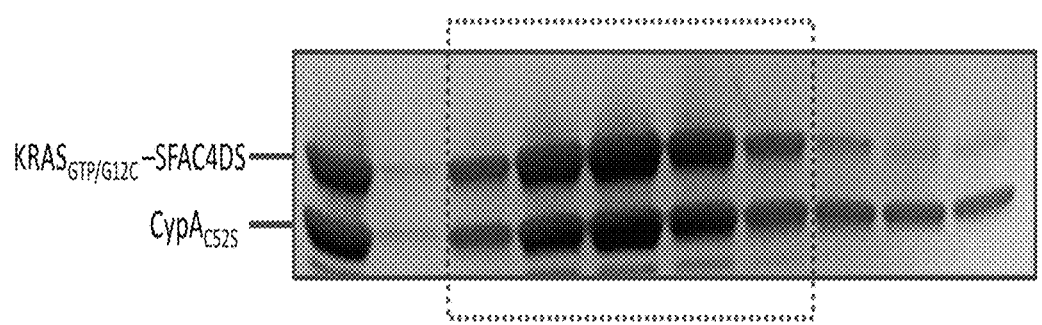

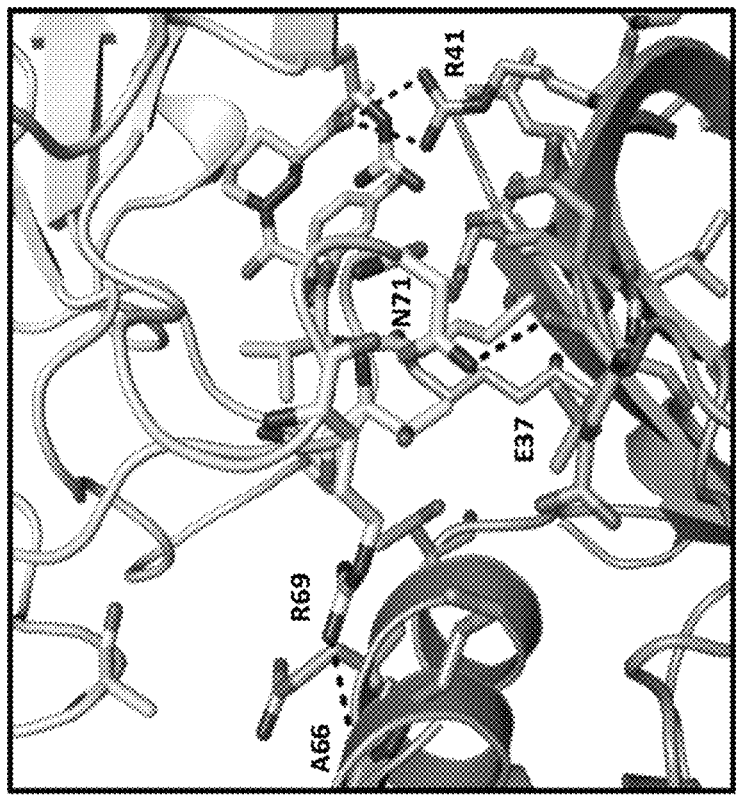
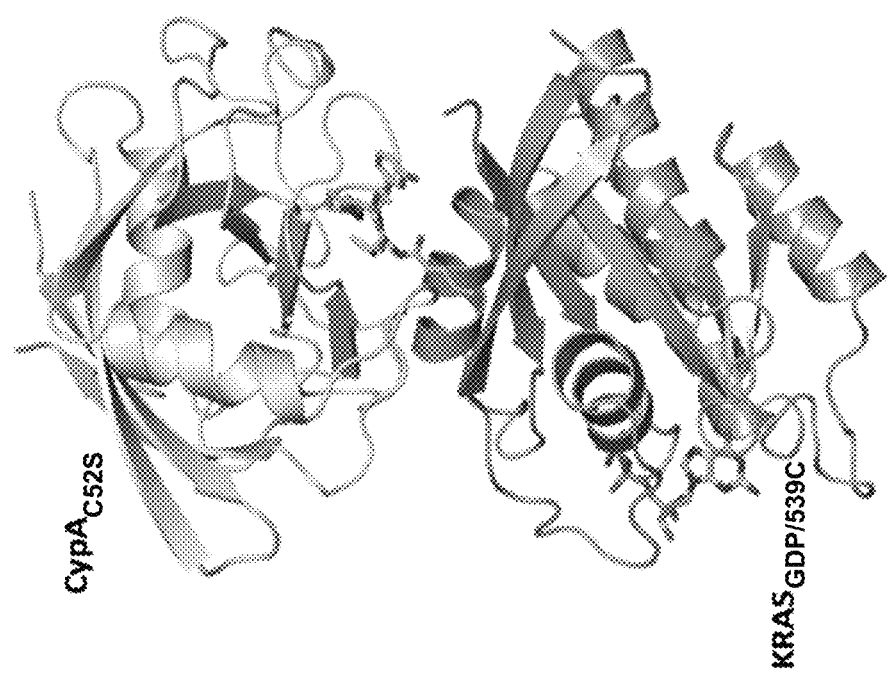
FIG. 8

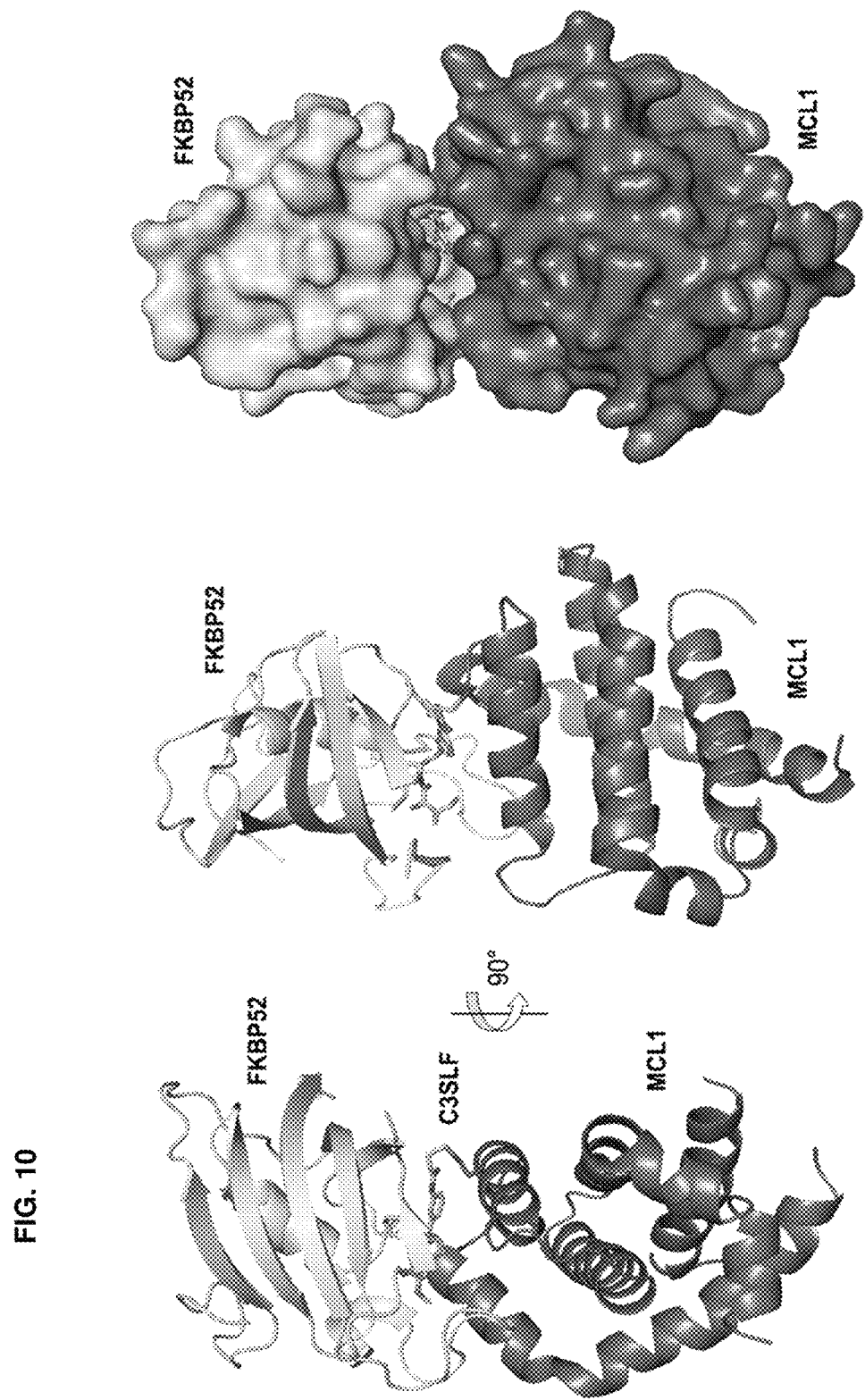

FIG. 13
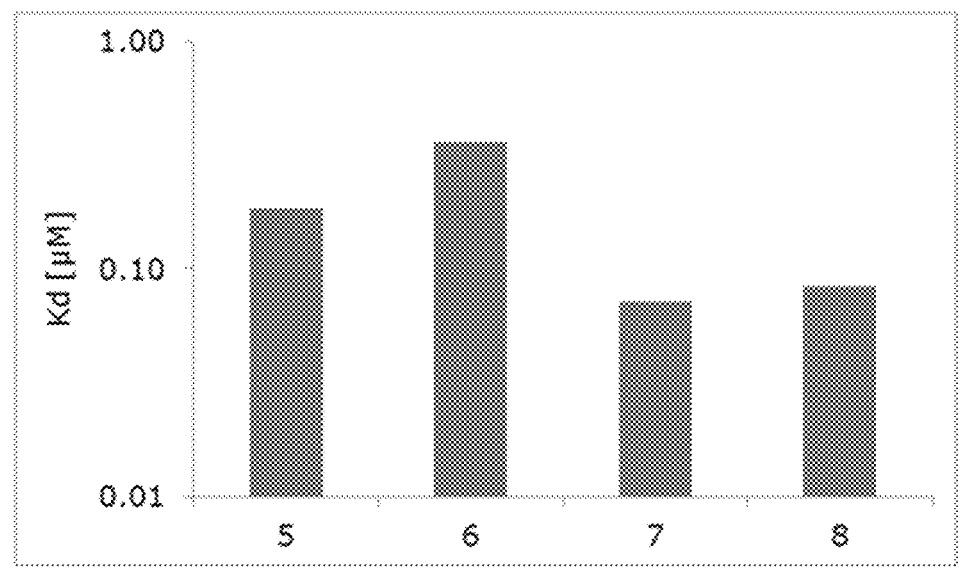
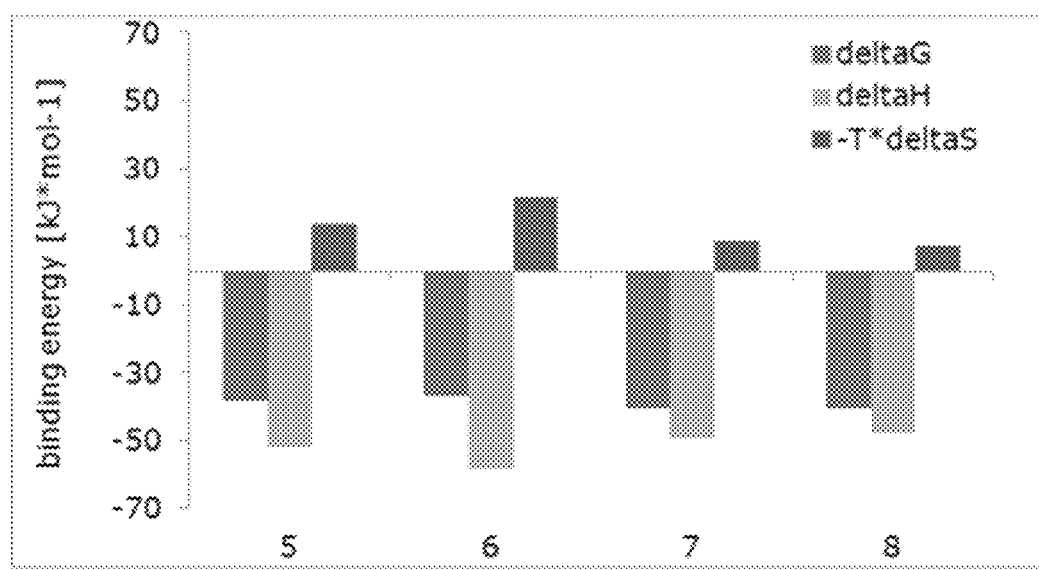

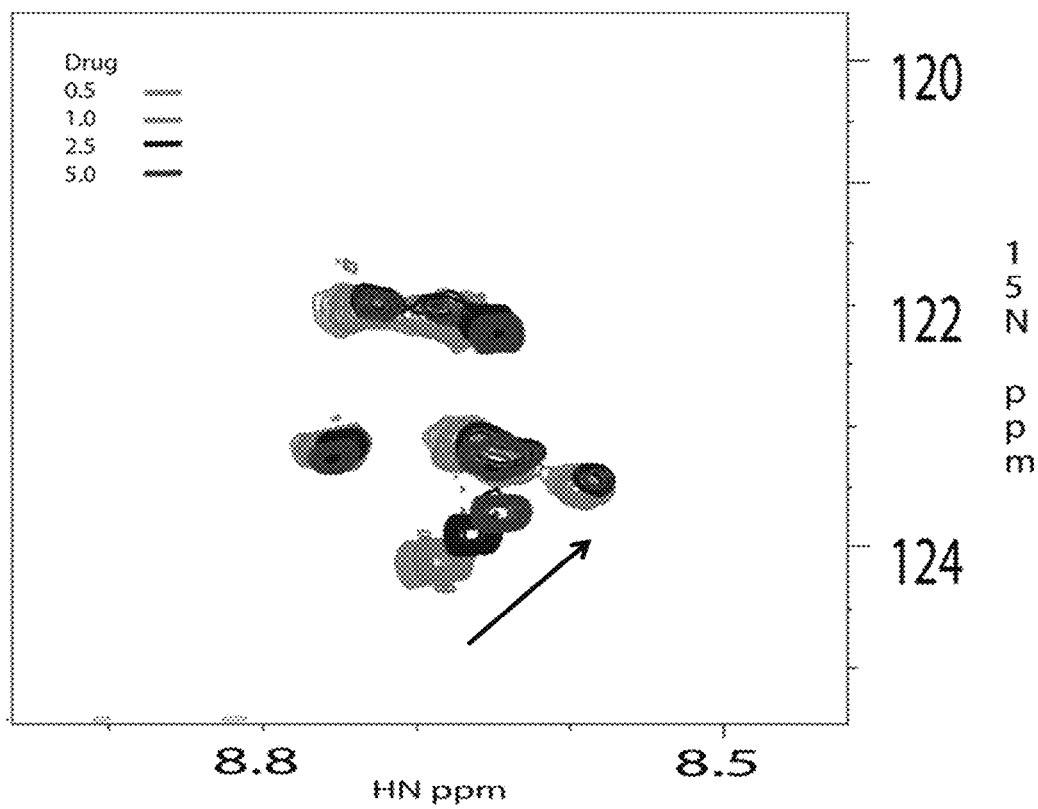

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Synthetic construct
```

```
<400> SEQUENCE: 1

Tyr Gln Asn Leu Leu Val Gly Arg Asn Arg Gly Glu Glu Ile Leu Asp
1               5                   10                  15
```

METHODS AND REAGENTS FOR ANALYZING PROTEIN-PROTEIN INTERFACES

REFERENCE TO A SEQUENCE LISTING

This application contains a Sequence Listing in computer readable form. The computer readable form is incorporated herein by reference.

BACKGROUND

The vast majority of small molecule drugs act by binding a functionally important pocket on a target protein, thereby modulating the activity of that protein. For example, the cholesterol-lowering drugs statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates hold that only about 10% of all human proteins are targetable by small molecules. The other 90% are currently considered refractory or intractable toward small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

SUMMARY

Small molecules are limited in their targeting ability because their interactions with the target are driven by adhesive forces, the strength of which is roughly proportional to contact surface area. Because of their small size, the only way for a small molecule to build up enough intermolecular contact surface area to effectively interact with a target protein is to be literally engulfed by that protein. Indeed, a large body of both experimental and computational data supports the view that only those proteins having a hydrophobic "pocket" on their surface are capable of binding small molecules. In those cases, binding is enabled by engulfment.

Nature has evolved a strategy that allows a small molecule to interact with target proteins at sites other than hydrophobic pockets. This strategy is exemplified by naturally occurring immunosuppressive drugs cyclosporine A, rapamycin, and FK506. The biological activity of these drugs involves the formation of a high-affinity complex of the small molecule with a small presenting protein. The composite surface of the small molecule and the presenting protein engages the target. Thus, for example, the binary complex formed between cyclosporin A and cyclophilin A targets calcineurin with high affinity and specificity, but neither cyclosporin A or cyclophilin A alone binds calcineurin with measurable affinity.

The present inventors have developed compounds and conjugates useful for identifying presenter protein and target protein pairs, and probing the interfaces between them for use in the development of small molecules capable of modulating these interactions.

Accordingly, the present disclosure provides methods and reagents useful for analyzing protein-protein interfaces such as interfaces between a presenter protein (e.g., a member of the FKBP family, a member of the cyclophilin family, or PIN1) and a target protein. Such analysis is useful in aiding the design of small molecules that are capable of binding simultaneously to both a presenter protein and a target protein, such that the resulting small molecule-presenter protein complexes can bind to and modulate the activity of the target protein. In some embodiments, the target and/or presenter proteins are intracellular proteins. In some embodiments, the target and/or presenter proteins are mammalian proteins.

In some aspect, the disclosure provides compounds that may be used as cross-linking substrates. These compounds may include a protein binding moiety capable of covalent or non-covalent binding to a protein (e.g., a target protein or a presenter protein) and at least one cross-linking group capable of a chemoselective reaction with an amino acid of a different protein than that which binds to the protein binding moiety. In some embodiments, the compounds include only one cross-linking group.

Accordingly, in an aspect, the disclosure provides a compound including a protein binding moiety (e.g., a presenter protein binding moiety or a target protein binding moiety) and a cross-linking group (e.g., a moiety capable of a chemoselective reaction with an amino acid of a different protein than that which binds to the protein binding moiety). The protein binding moiety is capable of binding (covalently or non-covalently) to a protein (e.g., a presenter protein or target protein, depending upon whether it is a presenter protein binding moiety or a target protein binding moiety), while the cross-linking group is capable of forming a covalent bond with a protein (e.g., a presenter protein, a target protein, or another compound that is capable of binding such other protein). In some embodiments, when the compound includes a presenter protein binding moiety, the compound does not include a target protein binding moiety. In some embodiments, when the compound includes a target protein binding moiety, the compound does not include a presenter protein binding moiety.

In some embodiments, the cross-linking group is a sulfhydryl-reactive cross-linking group (e.g., the cross-linking group includes a mixed disulfide, a maleimide, vinyl sulfone, vinyl ketone, or an alkyl halide), an amino-reactive cross-linking group, a carboxyl-reactive cross-linking group, a carbonyl-reactive cross-linking group, or a triazole-forming cross-linking group.

In some embodiments, the cross-linking group includes a mixed disulfide, e.g., the cross-linking group includes the structure of Formula I:

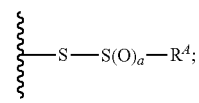

Formula I wherein the wavy line illustrates the point of attachment of the cross-linking group to the remainder of the compound; and a is 0, 1, or 2;

$R^A$ is optionally substituted $C_1$-$C_6$ alkyl, optionally substituted $C_1$-$C_6$ heteroalkyl, optionally substituted $C_6$-$C_{10}$ aryl, or optionally substituted $C_2$-$C_9$ heteroaryl.

In some embodiments, $R^A$ is optionally substituted $C_2$-$C_9$ heteroaryl (e.g., pyridyl). In some embodiments, the cross-linking group includes the structure:

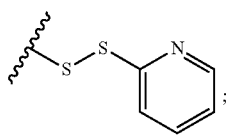 [SMILES: *SSc1ccccn1]

wherein the wavy line illustrates the point of attachment of the cross-linking group to the remainder of the compound.

In some embodiments, $R^A$ is optionally substituted $C_1$-$C_6$ alkyl (e.g., methyl). In some embodiments, the cross-linking group includes the structure:

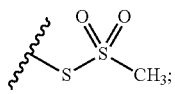

wherein the wavy line illustrates the point of attachment of the cross-linking group to the remainder of the compound.

In some embodiments, the cross-linking group includes a maleimide, e.g., the cross-linking group includes the structure:

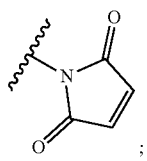

wherein the wavy line illustrates the point of attachment of the cross-linking group to the remainder of the compound.

In some embodiments, the cross-linking group includes a vinyl sulfone, e.g., the cross-linking group includes the structures:

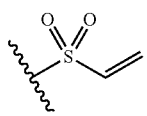 [SMILES: *S(=O)(=O)C=C]

wherein the wavy line illustrates the point of attachment of the cross-linking group to the remainder of the compound.

In some embodiments, the cross-linking group includes a vinyl ketone, e.g., the cross-linking group includes the structures:

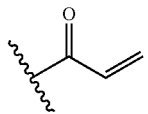

wherein the wavy line illustrates the point of attachment of the cross-linking group to the remainder of the compound.

In some embodiments, the cross-linking group includes an alkyl halide such as an alkyl chloride, e.g., the cross-linking group includes the structure:

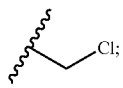

wherein the wavy line illustrates the point of attachment of the cross-linking group to the remainder of the compound.

In some embodiments of any of the foregoing compounds, the protein binding moiety portion is capable of non-covalent interaction with a protein. In some embodiments of any of the foregoing compounds, the protein binding moiety portion is capable of covalent interaction with a protein.

In some aspects, the disclosure provides a compound including a presenter protein binding moiety and a cross-linking group. In some embodiments, the protein binding moiety and the cross-linking group are attached through a linker.

In some aspects, the disclosure provides a compound having the structure:

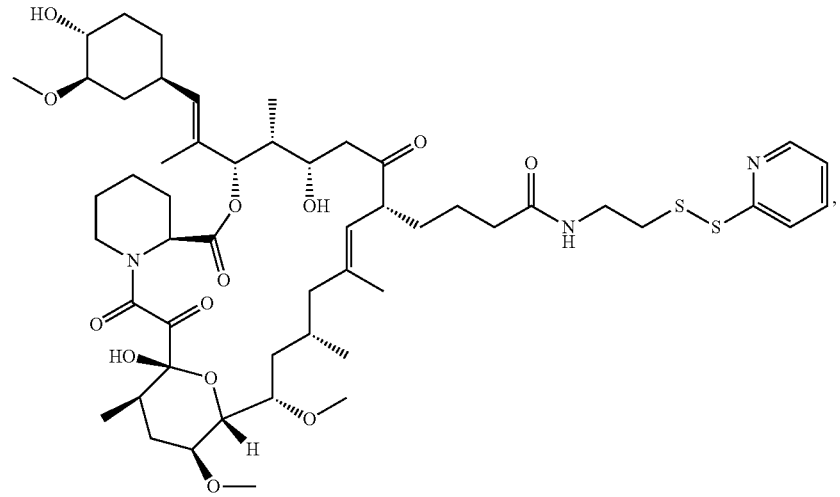

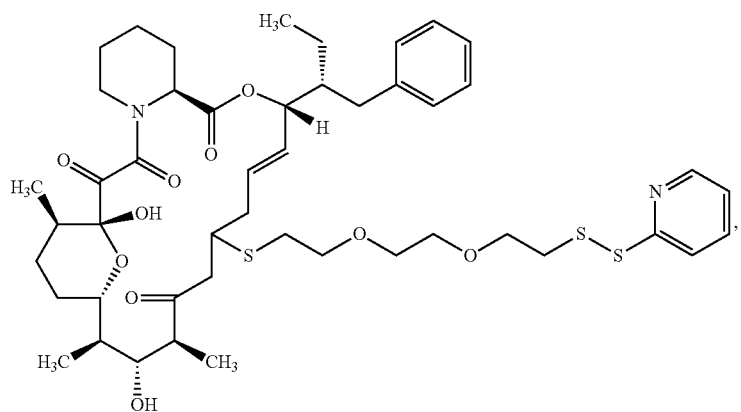
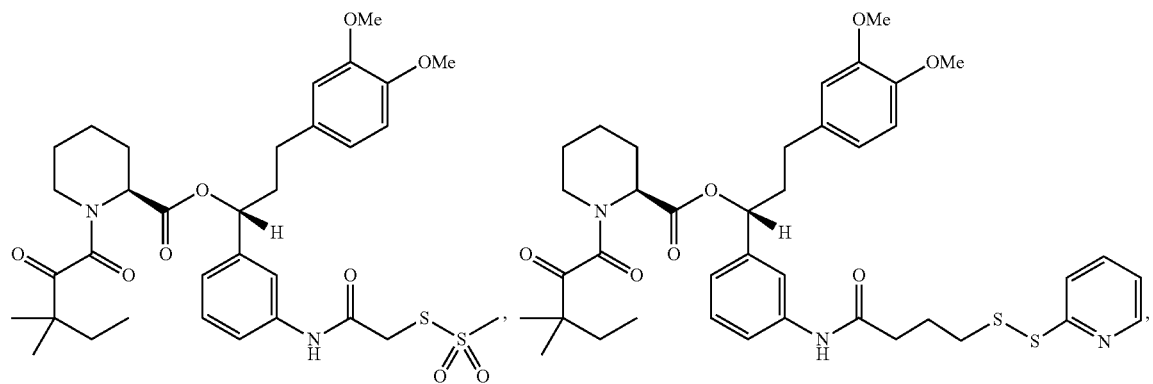
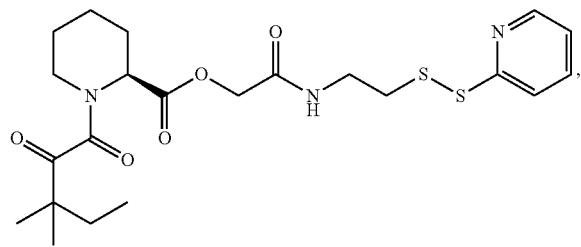
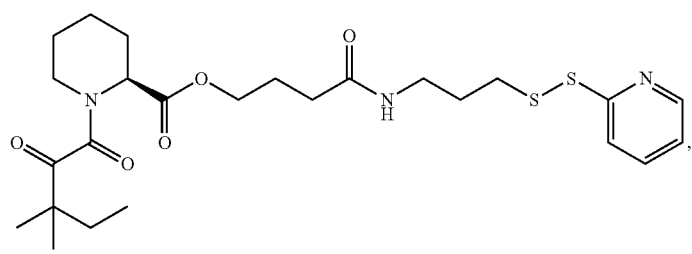

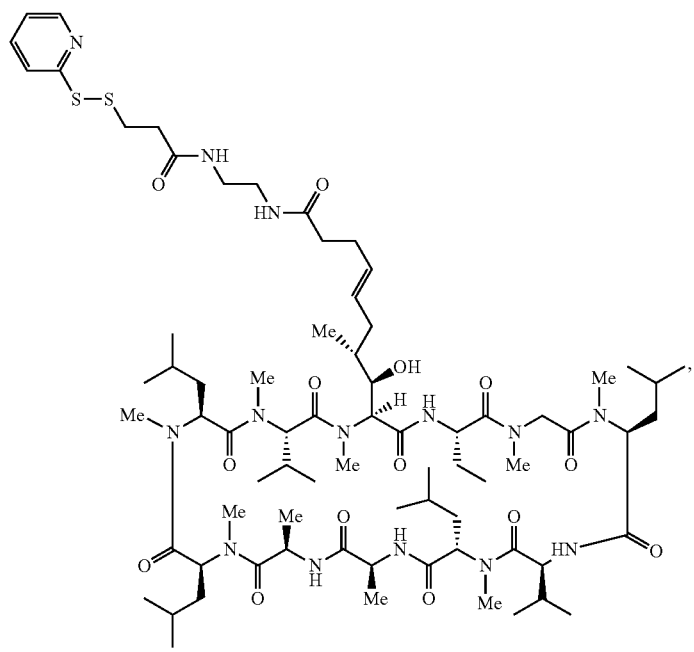
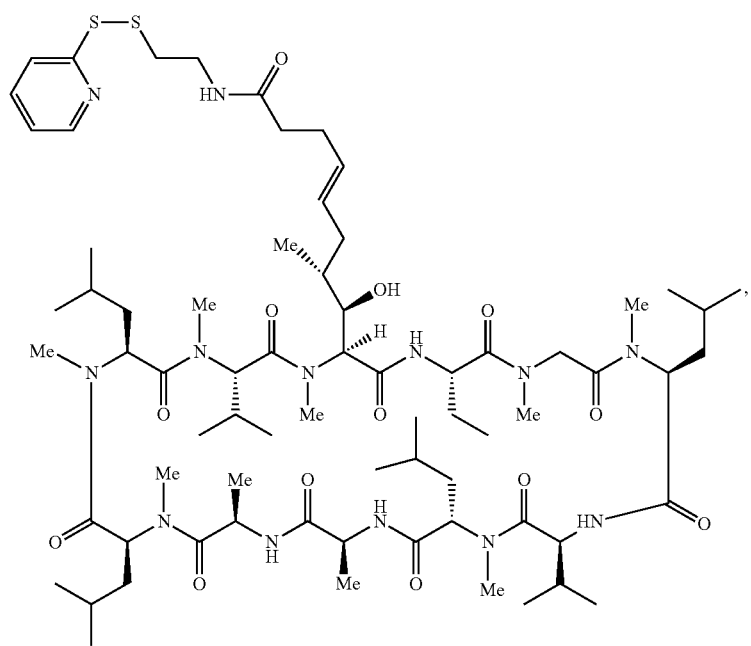

-continued
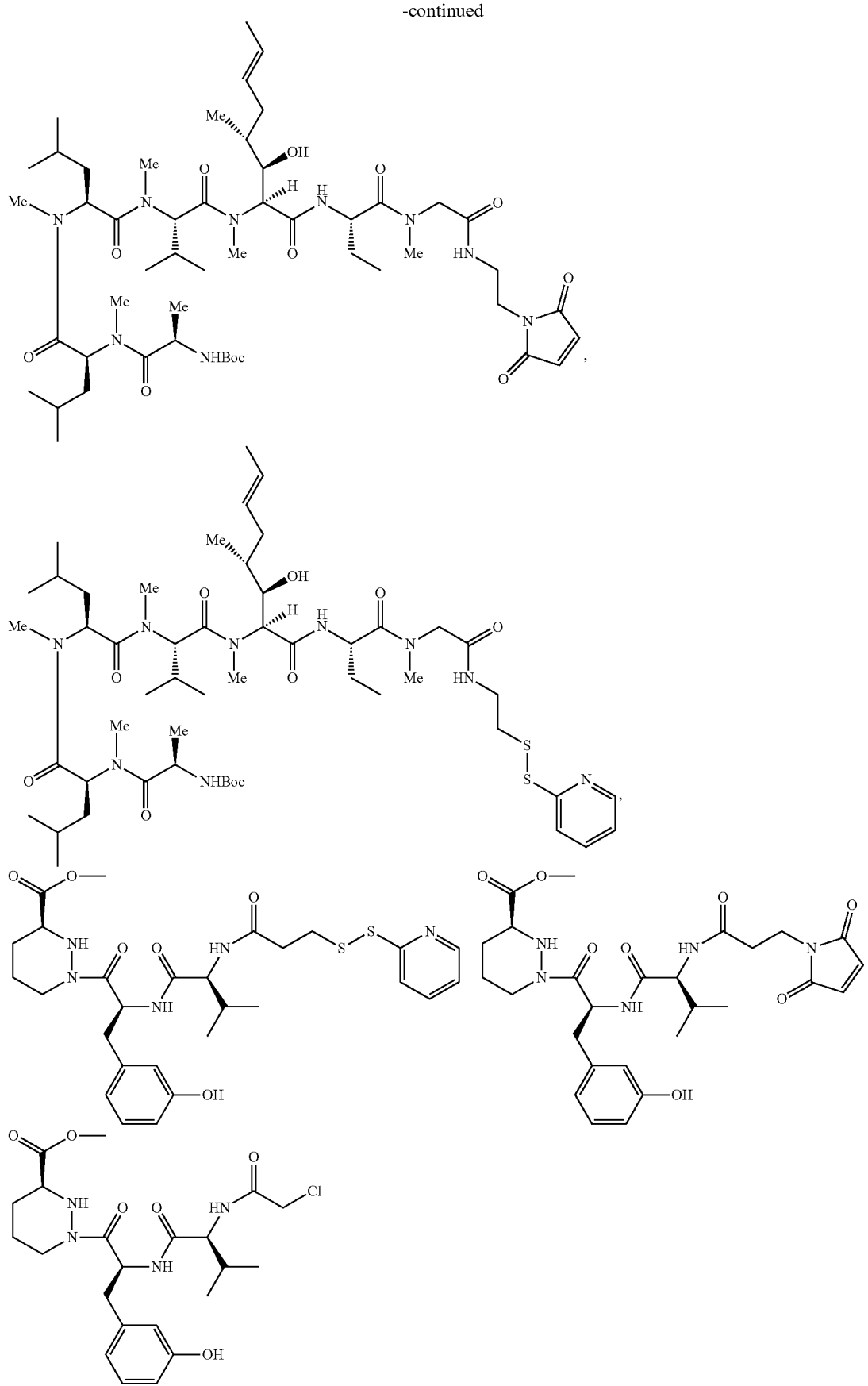

-continued
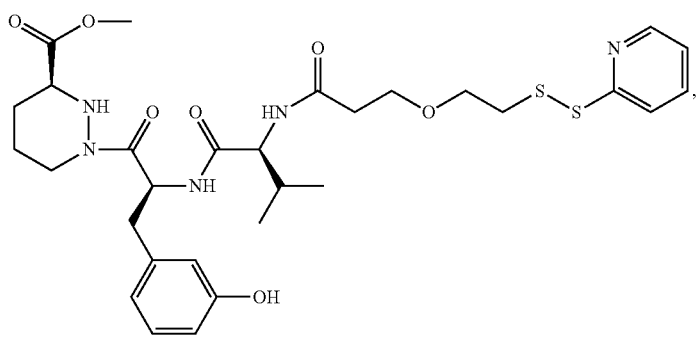
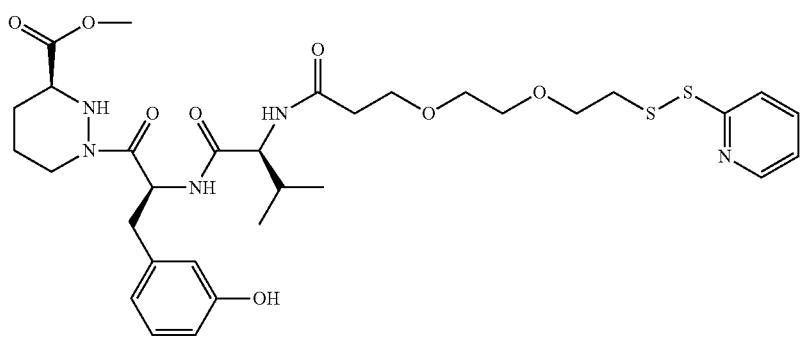
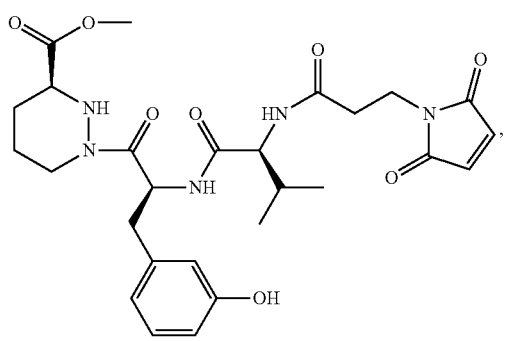
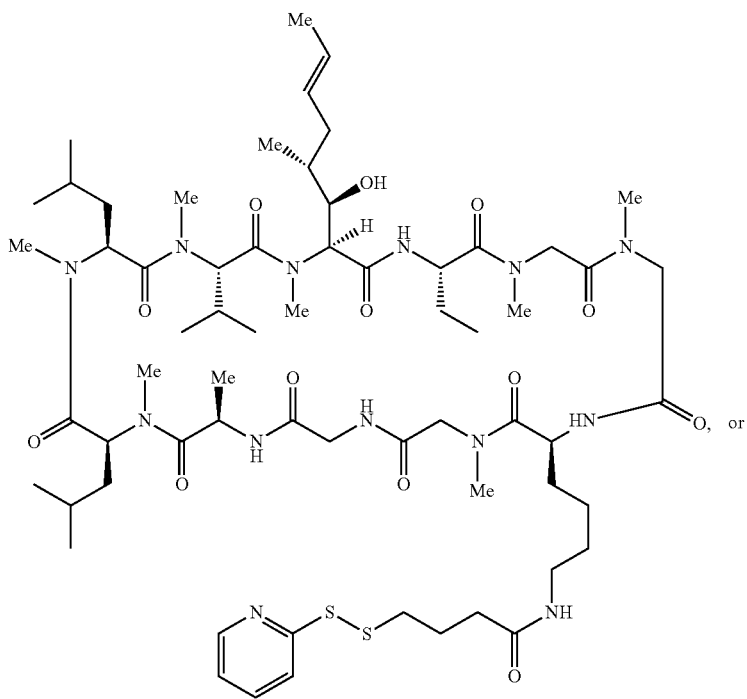
, or

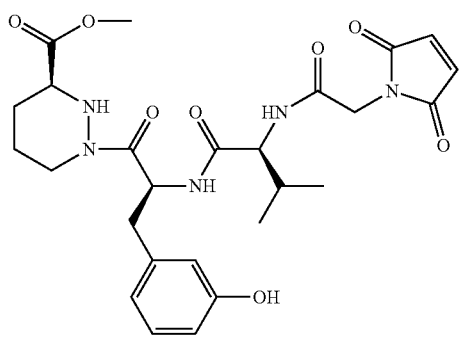 [SMILES: COC(=O)[C@@H]1CCCN(C(=O)[C@H](Cc2cccc(O)c2)NC(=O)[C@@H](NC(=O)CN2C(=O)C=CC2=O)C(C)C)N1]

-continued

In some aspects, the disclosure provides conjugates, methods for their synthesis, and uses thereof, including a presenter protein binding moiety capable of covalent or non-covalent binding to a presenter protein conjugated to a target protein through a linker.

Accordingly, in another aspect, the disclosure provides a conjugate including a presenter protein binding moiety conjugated to a target protein. In some embodiments, the presenter protein binding moiety portion of the conjugate is capable of non-covalent interaction with a presenter protein. In some embodiments, the presenter protein binding moiety portion of the conjugate is capable of covalent interaction with a presenter protein.

In some aspects, the disclosure provides a method of producing a conjugate including a presenter protein binding moiety conjugated to a target protein. This method includes reacting (a) a compound including a presenter protein binding moiety and a cross-linking group with (b) a target protein under conditions that permit production of the conjugate.

In some aspects, the disclosure provides a method of producing a conjugate including a presenter protein binding moiety conjugated to a target protein. This method includes providing (a) a compound including a presenter protein binding moiety and a cross-linking group; (b) a target protein; and (c) a presenter protein; and reacting the compound with the target protein under conditions that permit production of the conjugate.

In some aspects, the disclosure provides complexes, methods for their production, and uses thereof, including a presenter protein and a conjugate including a presenter protein binding moiety and a target protein.

Accordingly, in another aspect, the disclosure provides a complex including (i) a conjugate including a presenter protein binding moiety conjugated to a target protein and (ii) a presenter protein.

In some aspects, the disclosure provides a method of producing a complex including (i) a conjugate including a presenter protein binding moiety conjugated to a target protein and (ii) a presenter protein. This method includes combining a conjugate including a presenter protein binding moiety conjugated to a target protein and a presenter protein under conditions that permit production of the complex.

In some aspects, the disclosure provides a method of producing a complex including (i) a conjugate including a presenter protein binding moiety conjugated to a target protein and (ii) a presenter protein. This method includes providing (a) a compound including a presenter protein binding moiety and a cross-linking group; (b) a target protein; and (c) a presenter protein; and reacting the compound with the target protein under conditions that permit production of the complex.

In some embodiments of the foregoing methods, the presenter protein binds to the compound in the absence of the target protein. In some embodiments of the foregoing methods, the presenter protein does not substantially bind to the compound in the absence of the target protein. In some embodiments of the foregoing methods, the compound and the target protein do not substantially react in the absence of the presenter protein. In some embodiments of the foregoing methods, the compound and the target protein react in the absence of the presenter protein. In some embodiments of the foregoing methods, the conditions do not include a reducing reagent. In some embodiments of the foregoing methods, the conditions include an excess of presenter protein.

In some embodiments, detectable binding between the compound and the presenter protein is observed in the absence of the target protein. In some embodiments, however detectable binding between the compound and the presenter protein is not observed (e.g., the presenter protein does not substantially bind to the compound) in the absence of the target protein. In some embodiments, significant reaction between the cross-linking group and the target protein (e.g., significant conjugate formation) is not observed in the absence of the presenter protein. In some embodiments, however, significant reaction between the cross-linking group and the target protein may be observed even in the absence of the presenter protein. In some embodiments, rate and/or extent of such reaction (e.g., rate and/or amount of conjugate formation) may differ in a given assay when presenter protein is present as compared with when it is absent (e.g., the rate and/or amount of conjugate formation is 2-fold, 3-fold, 4-fold, 5-fold, 10-fold, or 100-fold greater in the presence of the presenter protein).

In some embodiments, conjugate production as described herein is performed under conditions that do not include (e.g., are substantially free of) a reducing reagent.

In some embodiments, the present invention provides a complex comprising (i) a presenter protein; (ii) a compound as described herein (e.g., compound whose structure includes a presenter protein binding moiety and a cross-linking group); and (iii) a target protein. In some embodiments, such complex is exposed to and/or maintained under conditions that permit reaction of the cross-linking moiety with the target protein, so that a cross-link therebetween is formed. In some embodiments, the cross-link is with a heteroatom in an amino acid (e.g., in an amino acid side chain) of the target protein. In some embodiments, the cross-link is with an —S— atom in a cysteine in the target protein. In some embodiments, the target protein is a variant of a natural target protein; in some such embodiments, the variant has an amino acid sequence that shows a high degree (e.g., 80%, 81%, 82%; 83%, 84%, 85%, 86%, 87%, 88%, 89%, 90%, 91%, 92%, 94%, 95%, 96%, 97%, 98%, 99% or higher) with the natural target protein but differs by substitution or addition of at least one amino acid susceptible to participation in a cross-link with the cross-linking group (e.g., whose amino acid side chain includes a heteroatom that can participate in such a cross-link).

In some aspects, the disclosure provides conjugates, methods for their synthesis, and uses thereof, including a target protein binding moiety capable of covalent or non-covalent binding to a target protein conjugated to a presenter protein through a linker.

Accordingly, in another aspect, the disclosure provides a conjugate including a target protein binding moiety conjugated to a presenter protein. In some embodiments, the target protein binding moiety portion of the conjugate is capable of non-covalent interaction with a target protein. In some embodiments, the target protein binding moiety portion of the conjugate is capable of non-covalent interaction with target protein. In some embodiments, the target protein binding moiety and the presenter protein are conjugated through a linker.

In some aspects, the disclosure provides a method of producing a conjugate including a target protein binding moiety conjugated to a presenter protein. This method includes reacting (a) a compound including a target protein binding moiety and a cross-linking group with (b) a presenter protein under conditions that permit production of the conjugate.

In some aspects, the disclosure provides a method of producing a conjugate including a target protein binding moiety conjugated to a presenter protein. This method includes providing (a) a compound including a target protein binding moiety and a cross-linking group; (b) a presenter protein; and (c) a target protein; and reacting the compound with the presenter protein under conditions that permit production of the conjugate.

In some embodiments, detectable binding between the compound and the target protein is observed absence the presenter protein. In some embodiments, however detectable binding between the compound and the target protein is not observed (e.g., the presenter protein does not substantially bind to the compound) in the absence of the presenter protein. In some embodiments, significant reaction between the cross-linking group and the presenter protein (e.g., significant conjugate formation) is not observed in the absence of the target protein. In some embodiments, however, significant reaction between the cross-linking group and the presenter protein may be observed even in the absence of the target protein. In some embodiments, the rate and/or extent of such reaction (e.g., the rate and/or amount of conjugate formation) may differ in a given assay when presenter protein is present as compared with when it is absent (e.g., the rate and/or amount of conjugate formation is 2-fold, 3-fold, 4-fold, 5-fold, 10-fold, 100-fold greater in the presence of the presenter protein).

In some embodiments, the target protein binds to the compound in the absence of the presenter protein. In some embodiments, the target protein does not substantially bind to the compound in the absence of the presenter protein. In some embodiments, the presenter protein does not substantially bind to the compound in the absence of the target protein. In some embodiments, reaction between the cross-linking group and the target protein (e.g., conjugate formation) is not observed in the absence of the presenter protein. In some embodiments, however, reaction between the cross-linking group and the target protein is observed even in the absence of the presenter protein. In some embodiments, conjugate production as described herein is performed under conditions that do not include (e.g., are substantially free of) a reducing agent.

In some embodiments, the present invention provides a complex comprising (i) a presenter protein; (ii) a compound as described herein (e.g., compound whose structure includes a presenter protein binding moiety and a cross-linking group); and (iii) a target protein. In some embodiments, such complex is exposed to and/or maintained under conditions that permit reaction of the cross-linking moiety with the target protein, so that a cross-link therebetween is formed. In some embodiments, the cross-link is with a heteroatom in an amino acid (e.g., in an amino acid side chain) of the target protein. In some embodiments, the cross-link is with an —S— atom in a cysteine in the target protein. In some embodiments, the target protein is a variant of a natural target protein; in some such embodiments, the variant has an amino acid sequence that shows a high degree (e.g., 80%, 81%, 82%; 83%, 84%, 85%, 86%, 87%, 88%, 89%, 90%, 91%, 92%, 94%, 95%, 96%, 97%, 98%, 99% or higher) with the natural target protein but differs by substitution or addition of at least one amino acid susceptible to participation in a cross-link with the cross-linking group (e.g., whose amino acid side chain includes a heteroatom that can participate in such a cross-link).

In some aspects, the disclosure provides complexes, methods for their production, and uses thereof, including a target protein and a conjugate including a target protein binding moiety conjugated to a presenter protein through a linker.

In some aspects, the disclosure provides a complex including (i) a conjugate including a target protein binding moiety conjugated to a presenter protein; (ii) a target protein; and (iii) a presenter protein. In some embodiments, such complex is exposed to and/or maintained under conditions that permit reaction of the cross-linking moiety with the presenter protein, so that a cross-link therebetween is formed. In some embodiments, the cross-link is with a heteroatom in an amino acid (e.g., in an amino acid side chain) of the presenter protein. In some embodiments, the cross-link is with an —S— atom in a cysteine in the presenter protein. In some embodiments, the presenter protein is a variant of a natural presenter protein; in some such embodiments, the variant has an amino acid sequence that shows a high degree (e.g., 80%, 81%, 82%; 83%, 84%, 85%, 86%, 87%, 88%, 89%, 90%, 91%, 92%, 94%, 95%, 96%, 97%, 98%, 99% or higher) with the natural presenter protein but differs by substitution or addition of at least one amino acid susceptible to participation in a cross-link with the cross-linking group (e.g., whose amino acid side chain includes a heteroatom that can participate in such a cross-link).

In some aspects, the disclosure provides a method of producing a complex including (i) a conjugate including a target protein binding moiety conjugated to a presenter protein and (ii) a target protein. This method includes combining a conjugate including a target protein binding moiety conjugated to a presenter protein and a target protein under conditions that permit production of the complex.

In some aspects, the invention features a method of producing a complex including (i) a conjugate as described herein (e.g., a conjugate including a target protein binding moiety and a presenter protein) and (ii) a target protein. In some such embodiments, a provided method includes combining the conjugate and target protein under conditions that permit production of the complex. Alternatively or additionally, in some embodiments, such a methods includes, for example, (i) combining (a) a compound (e.g., a compound whose structure includes a target protein binding moiety and a cross-linking group); (b) a target protein; and (c) a presenter protein with one another; and (ii) exposing the combination to and/or maintaining the combination under conditions that permit production of the complex. In some such embodiments, the conditions permit reaction of the cross-linking group with the presenter protein so that a conjugate is produced.

In some aspects, the disclosure provides a method of producing a complex including (i) a conjugate including a target protein binding moiety conjugated to a presenter protein and (ii) a target protein. This method includes providing (a) a compound including a target protein binding moiety and a cross-linking group; (b) a presenter protein; and (c) a target protein; and reacting the compound with the presenter protein under conditions that permit production of the complex.

In some such embodiments, the conditions are such that the compound, presenter protein, and/or target protein are characterized in that detectable binding between the compound and the target protein is observed in the absence of the presenter protein. In some embodiments, however, detectable binding between the compound and the target protein is not observed (e.g., the target protein does not substantially bind to the compound) under the conditions in the absence of the presenter protein. In some embodiments, significant reaction between the cross-linking group and the presenter protein is not observed in the absence of the target protein under the conditions. In some embodiments, however, significant reaction between the cross-linking group and the presenter protein may be observed even in the absence of the target protein under the conditions. In some embodiments, the conditions do not include a reducing reagent. In some embodiments, the conditions include an excess of presenter protein.

In some embodiments, the target protein binds to the compound in the absence of the presenter protein. In some embodiments, the target protein does not substantially bind to the compound in the absence of the presenter protein. In some embodiments, the compound and the presenter protein do not substantially react in the absence of the target protein. In some embodiments, the compound and the presenter protein react in the absence of the target protein. In some embodiments, the conditions do not include a reducing reagent. In some embodiments, the conditions include an excess of target protein.

In some aspects, the disclosure provides compounds including a presenter protein binding moiety capable on non-covalent interaction with a presenter protein and a target protein binding moiety capable of covalent or non-covalent interaction with a target protein. In some embodiments, the presenter protein binding moiety and the target protein binding moiety are attached via a linker.

Accordingly, in some aspects, the disclosure provides a compound having the structure of Formula VII:

A-L-B                    Formula VII wherein A includes the structure of Formula VIII:

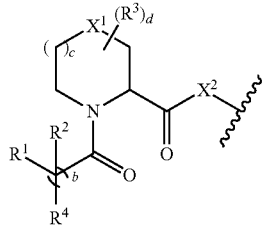

Formula VIII wherein b and c are independently 0, 1, or 2;
d is 0, 1, 2, 3, 4, 5, 6, or 7;
$X^1$ and $X^2$ are each, independently, absent, $CH_2$, O, S, SO, $SO_2$, or $NR^{13}$;
each $R^1$ and $R^2$ are independently hydrogen, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heterocyclyl (e.g., optionally substituted $C_2$-$C_9$ heteroaryl), optionally substituted $C_2$-$C_9$ heterocyclyl $C_1$-$C_6$ alkyl (e.g., optionally substituted $C_2$-$C_9$ heteroaryl $C_1$-$C_6$ alkyl), or $R^1$ and $R^2$ combine with the carbon atom to which they are bound to form C=O or $R^1$ and $R^2$ combine to form an optionally substituted $C_3$-$C_{10}$ carbocyclyl or optionally substituted $C_2$-$C_9$ heterocyclyl;
each $R^3$ is, independently, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heterocyclyl (e.g., optionally substituted $C_2$-$C_9$ heteroaryl), or optionally substituted $C_2$-$C_9$ heterocyclyl $C_1$-$C_6$ alkyl (e.g., optionally substituted $C_2$-$C_9$ heteroaryl $C_1$-$C_6$ alkyl) or two $R^8$ combine to form an optionally substituted $C_3$-$C_{10}$ carbocyclyl, optionally substituted $C_6$-$C_{10}$ aryl, optionally substituted $C_2$-$C_9$ heterocyclyl, e.g., optionally substituted $C_2$-$C_9$ heteroaryl;
$R^4$ is optionally substituted $C_1$-$C_6$ alkyl;
L is an optional linker; and
B is a target protein binding moiety.

In some embodiments of a compound of Formula VII, the target protein binding moiety, B, is capable of non-covalent interaction with a target protein. In some embodiments of a compound of Formula VII, the target protein binding moiety, B, is capable of covalent interaction with a target protein. In some embodiments of a compound of Formula VII, the linker, L, is present. In some embodiments of a compound of Formula VII, the linker, L, is absent.

In some aspects, the disclosure provides ternary complexes, methods for their production, and uses thereof, including a presenter protein, a target protein, and a compound including a presenter protein binding moiety and a target protein binding moiety.

Accordingly, in another aspect, the disclosure provides a complex including (i) a compound of Formula VII; (ii) a target protein; and (iii) a presenter protein.

In some embodiments, the compounds, conjugates, and complexes of the present invention may be useful for the identification of conjugates including a presenter protein binding moiety and a target protein that are capable of forming complexes with presenter proteins.

In some aspects, the invention features a method of identifying and/or characterizing a conjugate as described herein (e.g., in which a compound whose structure includes a presenter protein binding moiety and a cross-linking group, is conjugated to a target protein) that is capable of forming a complex with a presenter protein. In some embodiments, such a method includes steps of: (a) providing (i) such a conjugate (e.g., in which a compound whose structure includes a presenter protein binding moiety and a cross-linking group, conjugated to a target protein) and (ii) a presenter protein; (b) combining the conjugate and the presenter protein under conditions suitable to permit complex formation if the conjugate is capable of forming a complex with the presenter protein; and (c) determining whether a complex comprising the conjugate and the presenter protein is formed, wherein formation of the complex indicates that the conjugate is one that is capable of forming a complex with a presenter protein.

Accordingly, in some aspects, the disclosure provides a method of identifying and/or characterizing a conjugate that is capable of forming a complex with a presenter protein. This method includes the steps of: (a) providing (i) a conjugate including a presenter protein binding moiety conjugated to a target protein and (ii) a presenter protein; (b) combining the conjugate and the presenter protein under conditions suitable to permit complex formation if the conjugate is capable of forming a complex with the presenter protein; and (c) determining whether a complex comprising the conjugate and the presenter protein is formed, wherein formation of the complex indicates that the conjugate is one that is capable of forming a complex with a presenter protein.

In some embodiments, the compounds, conjugates, and complexes of the present invention may be useful for the identification of target proteins capable of forming covalent bonds to compounds in the presence of a presenter protein.

Accordingly, in another aspect, the disclosure provides a method of identifying and/or characterizing a target protein capable of reacting with a compound in the presence of a presenter protein, wherein the compound includes a presenter protein binding moiety and a cross-linking moiety. This method includes the steps of: (a) providing (i) a compound including a presenter protein binding moiety and a cross-linking moiety; (ii) a target protein; and (iii) a presenter protein; (b) combining the compound, the target protein, and the presenter protein under conditions suitable for to permit complex formation if the conjugate is capable of forming a complex with the presenter protein; and (c) determining whether the target protein and the compound react during formation of the complex to form a conjugate, wherein if the target protein and the compound form a conjugate, the target protein is identified as capable of reacting with the compound in the presence of a presenter protein.

In some embodiments, the compounds, conjugates, and complexes of the invention may be useful for the identification of target proteins capable of forming complexes with presenter proteins.

Accordingly, in another aspect, the disclosure provides a method of identifying and/or characterizing a target protein which binds to a presenter protein. This method includes the steps of: (a) providing (i) a conjugate including a presenter protein binding moiety conjugated to a target protein and (ii) a presenter protein; (b) combining the conjugate and the presenter protein under conditions suitable to permit complex formation if the conjugate is capable of forming a complex with the presenter protein; and (c) determining whether the target protein binds to the presenter protein in the complex, wherein if the target protein binds to the presenter protein, the target protein is identified as binding to the presenter protein.

In some aspects, the disclosure provides a method of identifying and/or characterizing a target protein which binds to a presenter protein. This method includes the steps of: (a) providing (i) a compound including a presenter protein binding moiety and a cross-linking moiety; (ii) a target protein; and (iii) a presenter protein; (b) combining the compound, the target protein, and the presenter protein under conditions suitable for to permit complex formation if the conjugate is capable of forming a complex with the presenter protein; and (c) determining whether the target protein binds to the presenter protein in the complex, wherein if the target protein binds to the presenter protein, the target protein is identified as a target protein that binds to a presenter protein.

In some aspects, the disclosure provides a method of identifying and/or characterizing a target protein capable of forming a complex with a presenter protein. This method includes the steps of: (a) providing (i) a compound of Formula VII; (ii) a target protein; and (iii) a presenter protein; (b) combining the compound, the target protein, and the presenter protein under conditions suitable to permit complex formation if the conjugate is capable of forming a complex with the presenter protein; and (c) determining if the compound, the target protein, and the presenter protein form a complex, wherein if the compound, the target protein, and the presenter protein form a complex, the target protein is identified as a target protein capable of forming a complex with a presenter protein.

In some aspects, the disclosure provides a method of identifying and/or characterizing a target protein which binds to a presenter protein. This method includes the steps of: (a) providing (i) a compound of Formula VII; (ii) a target protein; and (iii) a presenter protein; (b) combining the compound, the target protein, and the presenter protein under conditions suitable for to permit complex formation if the compound is capable of forming a complex with the presenter protein; and (c) determining whether the target protein binds to the presenter protein in the complex, wherein if the target protein binds to the presenter protein, the target protein is identified as a target protein that binds to a presenter protein.

In some aspects, the disclosure provides a method of identifying a target protein capable of forming a complex with a presenter protein by (a) providing (i) one or more target proteins, (ii) any of the foregoing compounds; and (iii) a presenter protein that includes a tag (e.g., an affinity tag); (b) combining the one or more target proteins, the compound, and the presenter protein under conditions suitable to permit complex formation if one or more of the target proteins is capable of forming a complex with the presenter protein; and (c) determining whether one or more target proteins form a complex with the compound and the presenter protein; wherein target proteins that form a complex with the presenter protein are identified as a target protein capable of forming a complex with a presenter protein.

In some embodiments, the determining step comprises utilizing the tag of said presenter protein to selectively isolate target proteins which have formed a complex with the presenter protein (e.g., by use in a pull down experiment). In some embodiments, the complex includes a target protein, a presenter protein, and a compound of the invention. In some embodiments, the complex includes a conjugate including a target protein and a presenter protein binding moiety (e.g., a conjugate formed by reaction between a cross-linking group of a compound of the invention and a reactive amino acid of a target protein) and a presenter protein. In some embodiments, the method further comprises (d) identifying the target protein (e.g., determining the structure of the target protein) in a complex formed between one or more target proteins, the compound, and the presenter protein. In some embodiments, the identifying of the structure of the target protein comprises performing mass spectrometry on the complex. In some embodiments, determination of whether the target protein and presenter protein form a complex and/or target protein binds to the presenter protein in the complex may be carried out using pull down experiments wherein either the target protein or the presenter protein is labeled (e.g., wherein a complex may be selectively pulled down in the presence of target proteins and/or presenter proteins which are not in a complex).

In some aspects, the disclosure provides a method of identifying a target protein capable of forming a complex with a presenter protein, by (a) providing (i) two or more target proteins; (ii) any of the foregoing compounds; and (iii) a presenter protein including an affinity tag; (b) combining the two or more target proteins, the compound, and the presenter protein under conditions suitable to permit complex formation if said target protein is capable of forming a complex with the presenter protein; (c) selectively isolating one or more complexes of a target protein, the compound, and the presenter protein formed in step (b); and (d) identifying the target protein (e.g., determining the structure of the target protein) in the one or more complexes isolated in step (c) by mass spectrometry; thereby identifying a target protein capable of forming a complex with a presenter protein.

In some embodiments, the determining step comprises utilizing the tag of said presenter protein to selectively isolate target proteins which have formed a complex with the presenter protein (e.g., by use in a pull down experiment). In some embodiments, the complex includes a target protein, a presenter protein, and a compound of the invention. In some embodiments, the complex includes a conjugate including a target protein and a presenter protein binding moiety (e.g., a conjugate formed by reaction between a cross-linking group of a compound of the invention and a reactive amino acid of a target protein) and a presenter protein. In some embodiments, determination of whether the target protein and presenter protein form a complex and/or target protein binds to the presenter protein in the complex may be carried out using pull down experiments wherein either the target protein or the presenter protein is labeled (e.g., wherein a complex may be selectively pulled down in the presence of target proteins and/or presenter proteins which are not in a complex).

In some embodiments, the compounds, conjugates, and complexes of the present invention may be useful to identify locations on target proteins to attach presenter protein binding moieties which result in conjugates capable of forming complexes with presenter proteins.

Accordingly, in another aspect, the disclosure provides a method of identifying and/or characterizing a location on a target protein to form a conjugate with a presenter protein binding moiety, which conjugate is capable of forming a complex with a presenter protein. This method includes the steps of: (a) providing (i) a conjugate including a presenter protein binding moiety conjugated to a target protein at a location and (ii) a presenter protein; (b) combining the conjugate and the presenter protein; (c) determining if the conjugate and the presenter protein form a complex; and (d) optionally repeating steps (a) to (c) with the presenter protein binding moiety conjugated at different locations on the target protein until a conjugate and the presenter protein form a complex, wherein a location on a target protein to form a conjugate with a presenter protein binding moiety, which conjugate is capable of forming a complex with a presenter protein is identified if the conjugate and the presenter protein form a complex. In some embodiments, the presenter protein is a variant of a naturally occurring target protein.

In some aspects, the disclosure provides a method of identifying and/or characterizing a location on a target protein to form a conjugate with a presenter protein binding moiety, which conjugate is capable of forming a complex with a presenter protein. This method includes the steps of: (a) providing (i) a compound including a presenter protein binding moiety and a cross-linking group; (ii) a target protein; and (iii) a presenter protein; (b) combining the compound with the target protein in the presence of the presenter protein under conditions that permit the formation of a conjugate including a presenter protein binding moiety conjugated to a target protein at a location; (c) determining if the conjugate and the presenter protein form a complex; and (d) optionally repeating steps (a) to (c) wherein the presenter protein binding moiety is conjugated at different locations on the target protein until a conjugate and the presenter protein form a complex; wherein a location on a target protein to form a conjugate with a presenter protein binding moiety, which conjugate is capable of forming a complex with a presenter protein is identified if the conjugate and the presenter protein form a complex, thereby identifying a location on a target protein to form a conjugate capable of forming a complex with a presenter protein. In some embodiments, the target protein is a variant of a naturally occurring target protein.

In some embodiments, the compounds, conjugates, and complexes of the present invention may be useful for identifying compounds capable of forming covalent bonds to target proteins in the presence of presenter proteins. In some embodiments, the compounds identified selectively form covalent bonds with target proteins in the presence of presenter proteins.

Accordingly, in another aspect, the disclosure provides a method of identifying and/or characterizing a compound capable of covalently binding to a target protein in the presence of a presenter protein. This method includes the steps of: (a) providing a sample including (i) a compound including a presenter protein binding moiety and a cross-linking group; (ii) a target protein; and (iii) a presenter protein; and (b) determining if the compound and the target protein form a covalent bond via the cross-linking group in said compound in the sample, wherein a compound is identified as covalently binding to a target protein in the presence of a presenter protein if the compound and the target protein react in the sample.

In some aspects, the disclosure provides a method of identifying and/or characterizing a compound capable of selective and covalent binding to a target protein in the presence of a presenter protein. This method includes the steps of: (a) providing a first sample including (i) a compound including a presenter protein binding moiety and a cross-linking group; (ii) a target protein; and (iii) a presenter protein and a second sample including (i) the same compound including a presenter protein binding moiety and a cross-linking group as in the first sample and (ii) the same target protein as in the first sample; and (b) determining the extent to which the compound and the target protein react in the first sample compared to the second sample, wherein a compound is identified as selectively covalently binding to a target protein in the presence of a presenter protein if the compound and the target protein reacts in the first sample more than in the second sample.

In some embodiments, a compound is identified as selectively covalently binding to a target protein in the presence of a presenter protein if the compound and the target protein reacts in the first sample at least 5-fold more than in the second sample. In some embodiments, a compound is identified as selectively covalently binding to a target protein in the presence of a presenter protein if the compound and the target protein reacts in the first sample, but does not substantially react in the second sample.

In some embodiments, the compounds, conjugates, and complexes of the present invention may be useful in identifying conjugates including a target protein and a presenter protein binding moiety capable of forming complexes with presenter proteins.

Accordingly, in another aspect, the disclosure provides a method of identifying and/or characterizing a conjugate capable of forming a complex with a presenter protein. This method includes the steps of: (a) providing (i) a conjugate including a presenter protein binding moiety conjugated to a target protein and (ii) a presenter protein; and (b) combining the conjugate and the presenter protein under conditions suitable for forming a complex; (c) determining if the conjugate and the presenter protein form a complex, wherein a conjugate is identified as capable of forming a complex with a presenter protein if the conjugate and the presenter protein form a complex, thereby identifying a conjugate capable of forming a complex with a presenter protein.

In some embodiments, binding between a conjugate and a protein may be determined by a method that includes a ternary time-resolved flourescence energy transfer assay, a ternary amplified luminescent proximity homogeneous assay, a isothermal titration calorimetry, surface plasmon resonance, or nuclear magnetic resonance.

In some embodiments, the compounds, conjugates, and complexes of the present invention may be useful for the determining the structure of protein-protein interfaces between presenter proteins and target proteins.

Accordingly, in another aspect, the disclosure provides a method of determining the structure of and/or assessing one or more structural features of an interface in a complex including a presenter protein and a target protein. This method includes the steps of: (a) providing (i) a conjugate including a presenter protein binding moiety conjugated to a target protein and (ii) a presenter protein; (b) contacting the conjugate with a presenter protein to form a complex (e.g., in a vial); and (c) determining the crystal structure of the complex, wherein the structure of the interface includes at least the portion of the crystal structure between the presenter protein and the target protein, thereby determining the structure of an interface in a complex including a presenter protein and a target protein.

In some aspects, the disclosure provides a method of determining the structure of and/or assessing one or more structural features of an interface in a complex including a presenter protein and a target protein. This method includes the steps of: (a) providing (i) a compound including a presenter protein binding moiety and a cross-linking moiety; (ii) a target protein; and (iii) a presenter protein; (b) combining the compound, the target protein, and the presenter protein under conditions suitable for forming a conjugate between the compound and target protein and for the formation of a complex between said conjugate and said presenter protein (e.g., in a vial); and (c) determining the crystal structure of the complex, wherein the structure of the interface includes at least the portion of the crystal structure between the presenter protein and the target protein, thereby determining the structure of an interface in a complex including a presenter protein and a target protein.

In some aspects, the disclosure provides a method of determining the structure of and/or assessing one or more structural features of an interface in a complex including a presenter protein and a target protein. This method includes the steps of: (a) providing (i) a compound of Formula VII; (ii) a target protein; and (iii) a presenter protein; (b) forming a complex including the compound, the target protein, and the presenter protein (e.g., in a vial); and (c) determining the crystal structure of the complex, wherein the structure of the interface includes at least the portion of the crystal structure between the presenter protein and the target protein, thereby determining the structure of an interface in a complex including a presenter protein and a target protein.

In some aspects, the disclosure provides a method of determining the structure of and/or assessing one or more structural features of a protein-protein interface in a complex including a presenter protein and a target protein. This method includes the steps of: (a) providing a crystal of any of the foregoing complexes; and (b) determining the structure of the crystal, wherein the structure of the interface includes at least the portion of the crystal structure between the presenter protein and the target protein, thereby determining the structure of a protein-protein interface in a complex including a presenter protein and a target protein.

In some aspects, the disclosure provides a method of identifying and/or characterizing compounds capable of modulating the biological activity of a target protein. This method includes the steps of: (a) providing the structure of a protein-protein interface in a complex including a presenter protein and a target protein (e.g., a structure determined by any of the foregoing methods); and (b) determining the structure of compounds capable of binding at the interface, thereby identifying compounds capable of modulating the biological activity of a target protein. In some embodiments, the structure of compounds capable of binding at the interface is determined using computational methods. In some embodiments, the structure of compounds capable of binding at the interface is determined by screening of compounds including a presenter protein binding moiety described herein for complex formation in the presence of a target protein and a presenter protein.

In some aspects, the disclosure provides a method of obtaining X-ray crystal coordinates for a complex. This method includes the steps of: (a) providing (i) a conjugate including a presenter protein binding moiety conjugated to a target protein and (ii) a presenter protein; (b) combining the conjugate and the presenter protein under conditions suitable for to permit complex formation if the conjugate is capable of forming a complex with the presenter protein; and (c) determining the crystal structure of the complex, thereby obtaining X-ray crystal coordinates for the complex.

In some aspects, the disclosure provides a method of obtaining X-ray crystal coordinates for a complex. This method includes the steps of: (a) providing (i) a compound including a presenter protein binding moiety and a cross-linking moiety; (ii) a target protein; and (iii) a presenter protein; (b) combining the compound, the target protein, and the presenter protein under conditions suitable for to permit complex formation if the compound is capable of forming a complex with the presenter protein; and (c) determining the crystal structure of the complex, thereby obtaining X-ray crystal coordinates for the complex.

In some aspects, the disclosure provides a method of obtaining X-ray crystal coordinates for a complex. This method includes the steps of: (a) providing (i) a compound of the invention; (ii) a target protein; and (iii) a presenter protein; (b) combining the compound, the target protein, and the presenter protein under conditions suitable for to permit complex formation if the compound is capable of forming a complex with the presenter protein; and (c) determining the crystal structure of the complex, thereby obtaining X-ray crystal coordinates for the complex.

In some aspects, the disclosure provides a method of determining the residues on a target protein that participate in binding with a presenter protein. This method includes the steps of: (a) providing X-ray crystal coordinates of a complex obtained by a method of the invention; (b) identifying the residues of the target protein which include an atom within 4 Å of an atom on the presenter protein; thereby determining the residues on a target protein that participate in binding with a presenter protein. In some aspects, the disclosure provides a method of determining biochemical and/or biophysical properties of any of the presenter protein/target protein complexes described herein. This method includes the steps of: (a) providing X-ray crystal coordinates of a complex described herein obtained by a method described herein; (b) calculating a biochemical and/or biophysical property of the complex; thereby determining biochemical and/or biophysical properties of a presenter protein/target protein complex.

In some embodiments, the biochemical and/or biophysical properties include the free energy of binding of a complex, the $K_d$ of a complex, the $K_i$ of a complex, the $K_{inact}$ of a complex, and/or the $K_i/K_{inact}$ of a complex. In some embodiments, the biochemical and/or biophysical properties are determined by isothermal titration calorimetry, surface plasmon resonance, and/or mass spectrometry.

In some embodiments, the interface in a complex including a presenter protein and a target protein is or comprises a binding pocket.

In some aspects, the disclosure provides compositions including any of the foregoing compounds, a target protein, and a presenter protein in solution.

In some aspects, the disclosure provides a pharmaceutical composition including any of the compounds, conjugates, or complexes of the invention and a pharmaceutically acceptable excipient. In some embodiments, the pharmaceutical composition is in unit dosage form.

In some aspects, the disclosure provides a method of modulating a target protein (e.g., a eukaryotic target protein such as a mammalian target protein or a fungal target proteins or a prokaryotic target protein such as a bacterial target protein). In some embodiments, such a method includes steps of contacting the target protein with a modulating (e.g., positive or negative modulation) amount of any of the compounds (e.g., in the presence of a presenter protein), conjugates including a target protein binding moiety, or compositions of the invention.

In some aspects, the disclosure provides a method of modulating (e.g., positively or negatively modulating) a target protein (e.g., a eukaryotic target protein such as a mammalian target protein or a fungal target proteins or a prokaryotic target protein such as a bacterial target protein). In some embodiments, such a method includes steps of contacting a cell expressing the target protein and a presenter protein with an effective amount of a compound or composition of the invention under conditions wherein the compound can form a complex with the presenter protein and the resulting complex can bind to the target protein, thereby modulating (e.g., positively or negatively modulating) the target protein.

In some aspects, the disclosure provides a method of modulating (e.g., positively or negatively modulating) a target protein (e.g., a eukaryotic target protein such as a mammalian target protein or a fungal target proteins or a prokaryotic target protein such as a bacterial target protein). In some embodiments, such a method includes steps of contacting the target protein with conjugate of the invention including a target protein binding moiety, thereby modulating the target protein.

In some aspects, the disclosure provides a method of inhibiting prolyl isomerase activity. In some embodiments, such a method includes contacting a cell expressing the prolyl isomerase with a compound or composition of the invention under conditions that permit the formation of a complex between the compound and the prolyl isomerase, thereby inhibiting the prolyl isomerase activity.

In some aspects, the disclosure provides a method of forming a presenter protein/compound complex in a cell. In some embodiments, such a method includes steps of contacting a cell expressing the presenter protein with a compound or composition of the invention under conditions that permit the formation of a complex between the compound and the presenter protein.

In some embodiments of any of the foregoing compounds, conjugates, complexes, compositions, or methods, the presenter protein binding moiety is capable of binding a protein encoded by any one of the genes of Table 1. In some embodiments of any of the foregoing compounds, conjugates, complexes, compositions, or methods, the presenter protein binding moiety is a prolyl isomerase binding moiety. In some embodiments of any of the foregoing compounds, conjugates, complexes, compositions, or methods, the presenter protein binding moiety is a FKBP binding moiety (e.g., the presenter protein binding moiety is capable of binding FKBP12, FKBP12.6, FKBP13, FKBP25, FKBP51, or FKBP52), a cyclophilin binding moiety (e.g., the presenter protein binding moiety is capable of binding PP1A, CYPB, CYPC, CYP40, CYPE, CYPD, NKTR, SRCyp, CYPH, CWC27, CYPL1, CYP60, CYPJ, PPIL4, PPIL6, RANBP2, or PPWD1), or a PIN1 binding moiety. In some embodiments of any of the foregoing methods, the presenter protein is known to bind to the presenter protein binding moiety.

In some embodiments of any of the foregoing compounds, conjugates, complexes, compositions, or methods, the presenter protein binding moiety is a FKBP binding moiety (e.g., a selective FKBP binding moiety or a non-selective FKBP binding moiety). In some embodiments of any of the foregoing compounds, conjugates, complexes, compositions, or methods, the FKBP binding moiety includes the structure of Formula IIa or IIb:

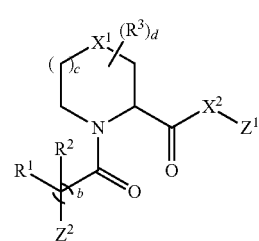

Formula IIa

-continued

Formula IIb

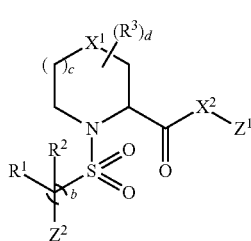

wherein $Z^1$ and $Z^2$ are each, independently, optionally substituted $C_1$-$C_6$ alkyl, optionally substituted $C_1$-$C_6$ heteroalkyl, or $Z^1$ and $Z^2$ combine to form, with the atoms to which they are attached, an optionally substituted 10 to 40 member macrocycle; and wherein at least one of $Z^1$ or $Z^2$ includes a point of attachment to the cross-linking group;

b and c are independently 0, 1, or 2;

d is 0, 1, 2, 3, 4, 5, 6, or 7;

$X^1$ and $X^2$ are each, independently, absent, $CH_2$, O, S, SO, $SO_2$, or $NR^4$;

each $R^1$ and $R^2$ are independently hydrogen, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heterocyclyl (e.g., optionally substituted $C_2$-$C_9$ heteroaryl), optionally substituted $C_2$-$C_9$ heterocyclyl $C_1$-$C_6$ alkyl (e.g., optionally substituted $C_2$-$C_9$ heteroaryl $C_1$-$C_6$ alkyl), or $R^1$ and $R^2$ combine with the carbon atom to which they are bound to form C=O or $R^1$ and $R^2$ combine to form an optionally substituted $C_3$-$C_{10}$ carbocyclyl or optionally substituted $C_2$-$C_9$ heterocyclyl;

each $R^3$ is, independently, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heterocyclyl (e.g., optionally substituted $C_2$-$C_9$ heteroaryl), or optionally substituted $C_2$-$C_9$ heterocyclyl $C_1$-$C_6$ alkyl (e.g., optionally substituted $C_2$-$C_9$ heteroaryl $C_1$-$C_6$ alkyl) or two $R^8$ combine to form an optionally substituted $C_3$-$C_{10}$ carbocyclyl, optionally substituted $C_6$-$C_{10}$ aryl, e.g., optionally substituted $C_2$-$C_9$ heteroaryl; and each $R^4$ is, independently, hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl.

In some embodiments of any of the foregoing compounds, conjugates, complexes, compositions, or methods, the presenter protein binding moiety includes the structure:

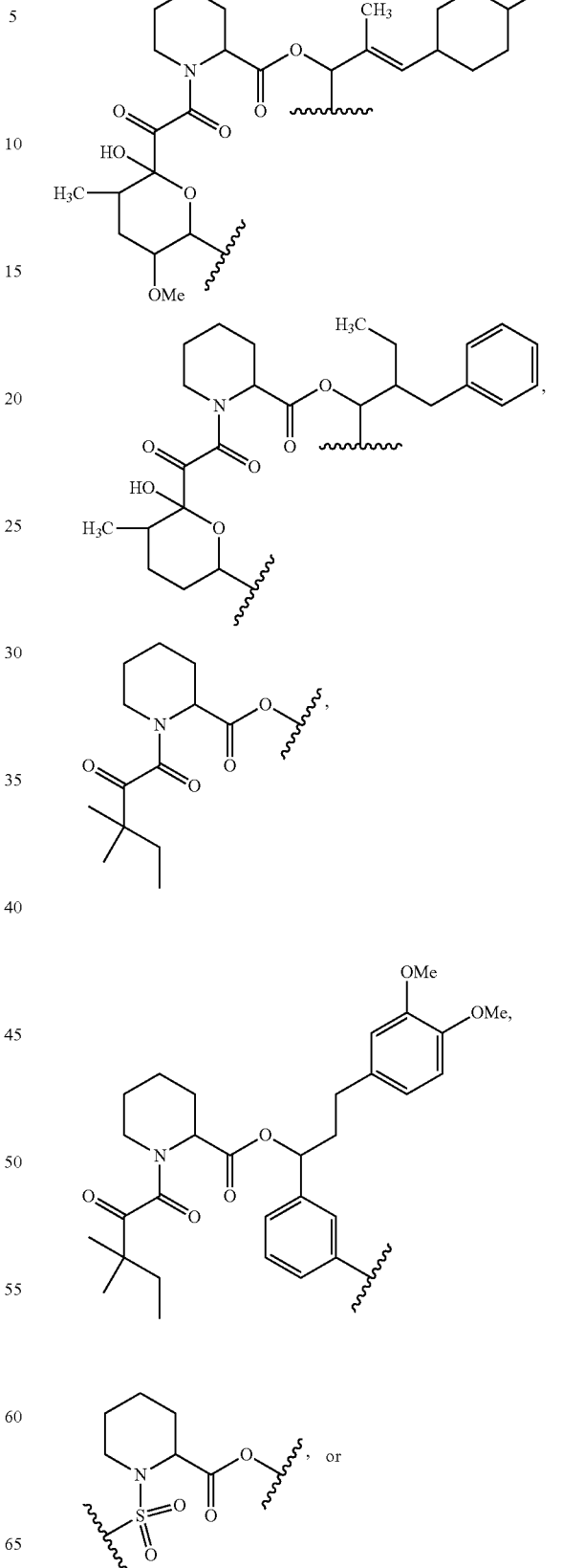

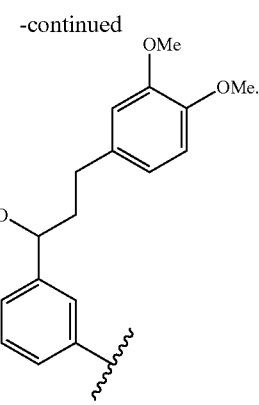

In some embodiments of any of the foregoing compounds, conjugates, complexes, compositions, or methods, the presenter protein binding moiety is a cyclophilin binding moiety (e.g., a selective cyclophilin binding moiety or a non-selective cyclophilin binding moiety). In some embodiments of any of the foregoing compounds, conjugates, complexes, compositions, or methods, the cyclophilin binding moiety includes the structure of Formula III or IV:

Formula III

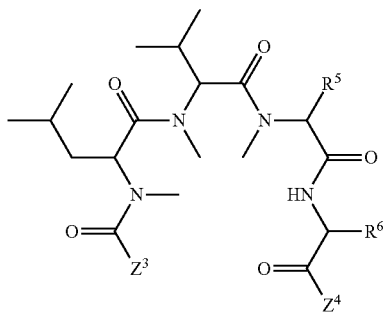

Formula IV

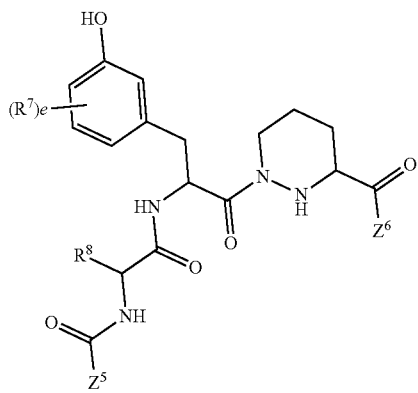

wherein $Z^3$, $Z^4$, $Z^5$, and $Z^6$ are each, independently, hydroxyl, optionally substituted $C_1$-$C_6$ alkyl, optionally substituted $C_1$-$C_6$ heteroalkyl, or $Z^3$ and $Z^4$ or $Z^5$ and $Z^6$ combine to form, with the atoms to which they are attached, an optionally substituted 10 to 40 member macrocycle;

at least one of $Z^3$, $Z^4$, $Z^5$, $Z^6$, or $R^5$ includes a point of attachment to the cross-linking group;

e is 0, 1, 2, 3, or 4;

$R^5$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^6$ is optionally substituted $C_1$-$C_6$ alkyl;

each $R^7$ is, independently, hydroxyl, cyano, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heterocyclyl (e.g., optionally substituted $C_2$-$C_9$ heteroaryl), or optionally substituted $C_2$-$C_9$ heterocyclyl $C_1$-$C_6$ alkyl (e.g., optionally substituted $C_2$-$C_9$ heteroaryl $C_1$-$C_6$ alkyl); and $R^8$ is hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl.

In some embodiments of any of the foregoing compounds, conjugates, complexes, compositions, or methods, the presenter protein binding moiety includes the structure:

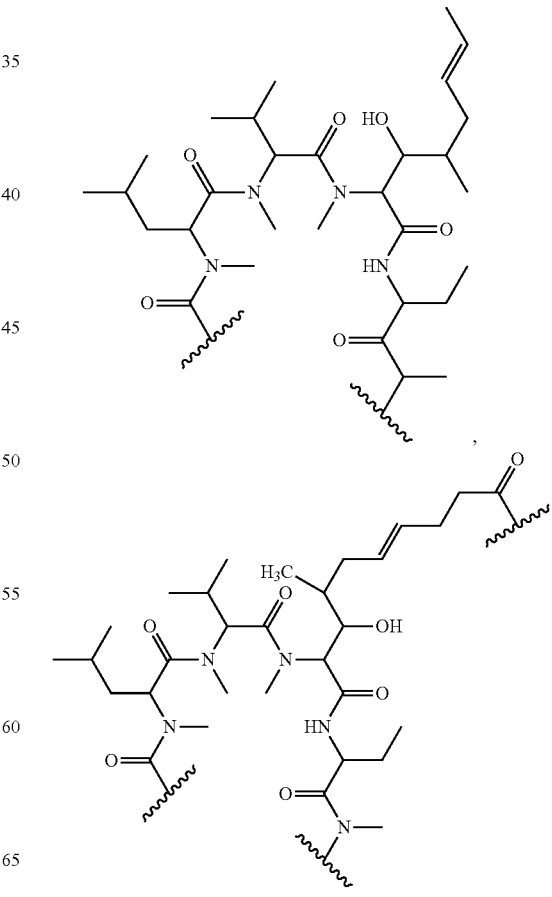

, or

-continued

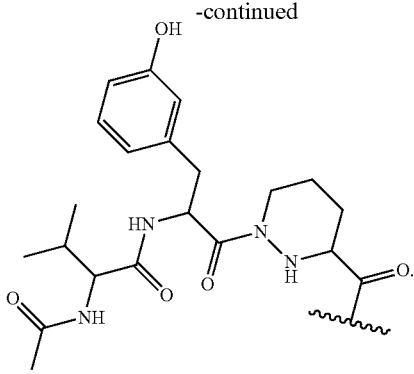

In some embodiments of any of the foregoing compounds, conjugates, complexes, compositions, or methods, the target protein is a GTPase, GTPase activating protein, Guanine nucleotide-exchange factor, a heat shock protein, an ion channel, a coiled-coil protein, a kinase, a phosphatase, a ubiquitin ligase, a transcription factor, a chromatin modifier/remodeler, or a protein with classical protein-protein interaction domains and motifs. In some embodiments of any of the foregoing compounds, conjugates, complexes, compositions, or methods, the target protein includes an undruggable surface. In some embodiments of any of the foregoing compounds, conjugates, complexes, compositions, or methods, the target protein does not have a traditional binding pocket.

In some embodiments of any of the foregoing compounds, conjugates, complexes, compositions, or methods, the amino acid sequence of the target protein has been modified to substitute at least one native amino acid with a reactive amino acid (e.g., a natural amino acid such as a cysteine, lysine, tyrosine, aspartic acid, glutamic acid, or serine, or a non-natural amino acid). In some embodiments of any of the foregoing compounds, conjugates, complexes, compositions, or methods, the amino acid sequence of the target protein has been modified to substitute at least one native reactive amino acid (e.g., a cysteine, lysine, tyrosine, aspartic acid, glutamic acid, or serine) with a non-reactive amino acid (e.g., a natural amino acid such as a serine, valine, alanine, isoleucine, threonine, tyrosine, aspartic acid, glutamic acid, or leucine, or a non-natural amino acid). In some embodiments of any of the foregoing compounds, conjugates, complexes, compositions, or methods, the at least one native reactive amino acid is a solvent exposed amino acid. In some embodiments of any of the foregoing compounds, conjugates, complexes, compositions, or methods, the amino acid sequence of the target protein is modified to substitute all reactive amino acids with a non-reactive amino acid. In some embodiments of any of the foregoing compounds, conjugates, complexes, compositions, or methods, the substitution is a conservative substitution. In some embodiments of any of the foregoing compounds, conjugates, complexes, compositions, or methods, the target protein includes only one solvent exposed reactive amino acid.

In some embodiments of any of the foregoing compounds, conjugates, complexes, compositions, or methods, the presenter protein is a protein encoded by any one of the genes of Table 1. In some embodiments of any of the foregoing compounds, conjugates, complexes, compositions, or methods, the presenter protein is a prolyl isomerase. In some embodiments of any of the foregoing compounds, conjugates, complexes, compositions, or methods, the prolyl isomerase is a member of the FKBP family (e.g., FKBP12, FKBP12.6, FKBP13, FKBP25, FKBP51, or FKBP52), a member of the cyclophilin family (e.g., PP1A, CYPB, CYPC, CYP40, CYPE, CYPD, NKTR, SRCyp, CYPH, CWC27, CYPL1, CYP60, CYPJ, PPIL4, PPIL6, RANBP2, or PPWD1), or PIN1.

In some embodiments of any of the foregoing compounds, conjugates, complexes, compositions, or methods, the amino acid sequence of the presenter protein has been modified to substitute at least one native amino acid with a reactive amino acid (e.g., a natural amino acid such as a cysteine, lysine, tyrosine, aspartic acid, glutamic acid, or serine, or a non-natural amino acid). In some embodiments of any of the foregoing compounds, conjugates, complexes, compositions, or methods, the amino acid sequence of the presenter protein has been modified to substitute at least one native reactive amino acid (e.g., a cysteine, lysine, tyrosine, aspartic acid, glutamic acid, or serine) with a non-reactive amino acid (e.g., a natural amino acid such as a serine, valine, alanine, isoleucine, threonine, tyrosine, aspartic acid, glutamic acid, or leucine, or a non-natural amino acid). In some embodiments of any of the foregoing compounds, conjugates, complexes, compositions, or methods, the at least one native reactive amino acid is a solvent exposed amino acid. In some embodiments of any of the foregoing compounds, conjugates, complexes, compositions, or methods, the amino acid sequence of the presenter protein is modified to substitute all reactive amino acids with a non-reactive amino acid. In some embodiments of any of the foregoing compounds, conjugates, complexes, compositions, or methods, the substitution is a conservative substitution.

In some embodiments of any of the foregoing compounds, conjugates, complexes, compositions, or methods, the linker is 1 to 20 atoms in length. In some embodiments of any of the foregoing compounds, conjugates, complexes, compositions, or methods, the linker is 1.5 to 30 angstroms in length.

In some embodiments of any of the foregoing compounds, conjugates, complexes, compositions, or methods, the linker has the structure of Formula V:

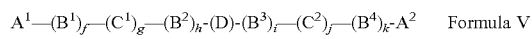

$A^1-(B^1)_f-(C^1)_g-(B^2)_h-(D)-(B^3)_i-(C^2)_j-(B^4)_k-A^2$   Formula V wherein $A^1$ is a bond between the linker and protein binding moiety; $A^2$ is a bond between the cross-linking group and the linker; $B^1$, $B^2$, $B^3$, and $B^4$ each, independently, is selected from optionally substituted $C_1$-$C_2$ alkyl, optionally substituted $C_1$-$C_3$ heteroalkyl, O, S, and $NR^N$; $R^N$ is hydrogen, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; $C^1$ and $C^2$ are each, independently, selected from carbonyl, thiocarbonyl, sulphonyl, or phosphoryl; f, g, h, i, j, and k are each, independently, 0 or 1; and D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$-$(C^1)_g$-$(B^2)_h$— to —$(B^3)_i$-$(C^2)_j$-$(B^4)_k$-$A^2$.

In some embodiments of any of the foregoing compounds, conjugates, complexes, compositions, or methods, the linker includes the structure of Formula VI:

Formula VI

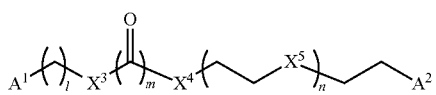

wherein $A^1$ is a bond between the linker and protein binding moiety;

$A^2$ is a bond between the cross-linking group and the linker;

l is 0, 1, 2, or 3;

m is 0 or 1;

n is 0, 1, or 2; and $X^3$, $X^4$, and $X^5$ are each, independently, absent, O, S, —C≡C—, $CR^9R^{10}$ or $NR^{11}$; and each $R^9$, $R^{10}$, and $R^{11}$ are, independently, hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl. In some embodiments, each $R^9$, $R^{10}$, and $R^{11}$ are, independently, hydrogen, unsubstituted $C_1$-$C_6$ alkyl, unsubstituted $C_2$-$C_6$ alkenyl, unsubstituted $C_2$-$C_6$ alkynyl, unsubstituted aryl, $C_3$-$C_7$ carbocyclyl, unsubstituted $C_6$-$C_{10}$ aryl $C_1$-$C_6$ alkyl, and unsubstituted $C_3$-$C_7$ carbocyclyl $C_1$-$C_6$ alkyl.

In some embodiments of any of the foregoing compounds, conjugates, complexes, compositions, or methods, the linker includes the structure:

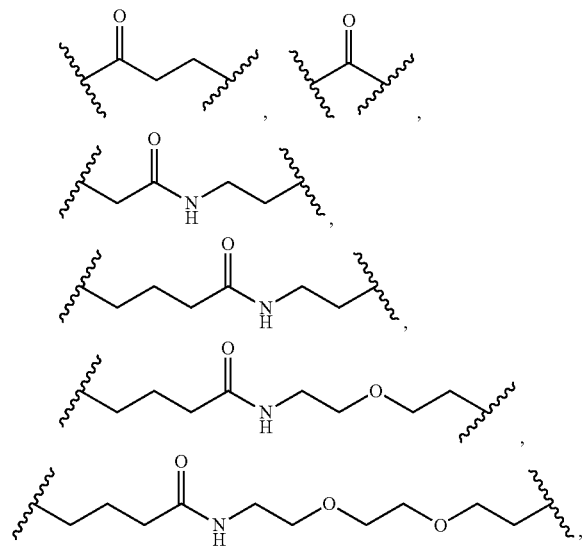

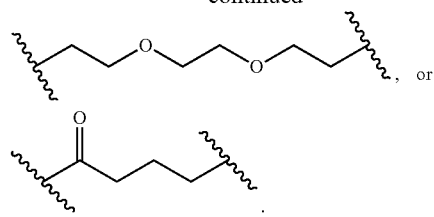

Chemical Terms

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion, e.g., the interconversion illustrated in the scheme below:

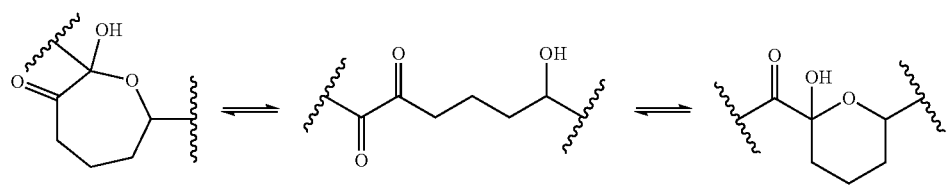 [SMILES: *C1CCCC(=O)C(*)(O)O1 ; *C(=O)C(=O)CCCC(*)O ; *C(=O)C1(O)CCCC(*)O1]

Those skilled in the art will appreciate that, in some embodiments, isotopes of compounds described herein may be prepared and/or utilized in accordance with the present invention. "Isotopes" refers to atoms having the same atomic number but different mass numbers resulting from a different number of neutrons in the nuclei. For example, isotopes of hydrogen include tritium and deuterium. In some embodiments, an isotopic substitution (e.g., substitution of hydrogen with deuterium) may alter the physicochemical properties of the molecules, such as metabolism and/or the rate of racemization of a chiral center.

As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

In some embodiments, compounds described and/or depicted herein may be provided and/or utilized in salt form.

In certain embodiments, compounds described and/or depicted herein may be provided and/or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

The term "alkyl," as used herein, refers to saturated hydrocarbon groups containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., $-NH_2$) or a substituted amino (i.e., $-N(R^{N1})_2$, where $R^{N1}$ is as defined for amino); (4) $C_{6-10}$ aryl-$C_{1-6}$ alkoxy; (5) azido; (6) halo; (7) ($C_{2-9}$ heterocyclyl) oxy; (8) hydroxyl, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) $-CO_2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of $-(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) $-C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) $-SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxyl; (17) $-SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) $-C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of $-(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) $-NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of $-(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) $-NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of $-(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of $-NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl;

(21) amidine; and (22) silyl groups such as trimethylsilyl, t-butyldimethylsilyl, and tri-isopropylsilyl. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents $-N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., $-NH_2$) or a substituted amino (i.e., $-N(R^{N1})_2$). In a preferred embodiment, amino is $-NH_2$ or $-NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{6-10}$ aryl.

The term "amino acid," as described herein, refers to a molecule having a side chain, an amino group, and an acid group (e.g., a carboxy group of $-CO_2H$ or a sulfo group of $-SO_3H$), wherein the amino acid is attached to the parent molecular group by the side chain, amino group, or acid group (e.g., the side chain). As used herein, the term "amino acid" in its broadest sense, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide. In some embodiments, the amino acid is attached to the parent molecular group by a carbonyl group, where the side chain or amino group is attached to the carbonyl group. In some embodiments, the amino acid is an α-amino acid. In certain embodiments, the amino acid is a β-amino acid. In some embodiments, the amino acid is a γ-amino acid. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., $-NH_2$) or a substituted amino (i.e., $-N(R^{N1})_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxyl; (9) nitro; (10) oxo (e.g., carboxyaldehyde or acyl); (11) $C_{1-7}$ spirocyclyl; (12) thioalkoxy; (13) thiol; (14) $-CO_2R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of $-(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h)

amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; (15) —C(O)NR$^{B'}$R$^{C'}$, where each of R$^{B'}$ and R$^{C'}$ is, independently, selected from the group consisting of (a) hydrogen, (b) C$_{1-6}$ alkyl, (c) C$_{6-10}$ aryl, and (d) C$_{1-6}$ alk-C$_{6-10}$ aryl; (16) —SO$_2$R$^{D'}$, where R$^{D'}$ is selected from the group consisting of (a) C$_{1-6}$ alkyl, (b) C$_{6-10}$ aryl, (c) C$_{1-6}$ alk-C$_{6-10}$ aryl, and (d) hydroxyl; (17) —SO$_2$NR$^{E'}$R$^{F'}$, where each of R$^{E'}$ and R$^{F'}$ is, independently, selected from the group consisting of (a) hydrogen, (b) C$_{1-6}$ alkyl, (c) C$_{6-10}$ aryl and (d) C$_{1-6}$ alk-C$_{6-10}$ aryl; (18) —C(O)R$^{G'}$, where R$^{G'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alk-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; (19) —NR$^{H'}$C(O)R$^{I'}$, wherein R$^{H'}$ is selected from the group consisting of (a1) hydrogen and (b1) C$_{1-6}$ alkyl, and R$^{I'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alk-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; (20) —NR$^{J'}$C(O)OR$^{K'}$, wherein R$^{J'}$ is selected from the group consisting of (a1) hydrogen and (b1) C$_{1-6}$ alkyl, and R$^{K'}$ is selected from the group consisting of (a2) C$_{1-20}$ alkyl (e.g., C$_{1-6}$ alkyl), (b2) C$_{2-20}$ alkenyl (e.g., C$_{2-6}$ alkenyl), (c2) C$_{6-10}$ aryl, (d2) hydrogen, (e2) C$_{1-6}$ alk-C$_{6-10}$ aryl, (f2) amino-C$_{1-20}$ alkyl, (g2) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each R$^{N1}$ is, independently, hydrogen or optionally substituted C$_{1-6}$ alkyl; and (21) amidine. In some embodiments, each of these groups can be further substituted as described herein.

The term "N-alkylated amino acids" as used herein, refers to amino acids containing an optionally substituted C$_1$ to C$_6$ alkyl on the nitrogen of the amino acid that forms the peptidic bond. N-alkylated amino acids include, but are not limited to, N-methyl amino acids, such as N-methyl-alanine, N-methyl-threonine, N-methyl-phenylalanine, N-methyl-aspartic acid, N-methyl-valine, N-methyl-leucine, N-methyl-glycine, N-methyl-isoleucine, N($\alpha$)-methyl-lysine, N($\alpha$)-methyl-asparagine, and N($\alpha$)-methyl-glutamine.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) C$_{1-7}$ acyl (e.g., carboxyaldehyde); (2) C$_{1-20}$ alkyl (e.g., C$_{1-6}$ alkyl, C$_{1-6}$ alkoxy-C$_{1-6}$ alkyl, C$_{1-6}$ alkylsulfinyl-C$_{1-6}$ alkyl, amino-C$_{1-6}$ alkyl, azido-C$_{1-6}$ alkyl, (carboxyaldehyde)-C$_{1-6}$ alkyl, halo-C$_{1-6}$ alkyl (e.g., perfluoroalkyl), hydroxy-C$_{1-6}$ alkyl, nitro-C$_{1-6}$ alkyl, or C$_{1-6}$ thioalkoxy-C$_{1-6}$ alkyl); (3) C$_{1-20}$ alkoxy (e.g., C$_{1-6}$ alkoxy, such as perfluoroalkoxy); (4) C$_{1-6}$ alkylsulfinyl; (5) C$_{6-10}$ aryl; (6) amino; (7) C$_{1-6}$ alk-C$_{6-10}$ aryl; (8) azido; (9) C$_{3-8}$ cycloalkyl; (10) C$_{1-6}$ alk-C$_{3-8}$ cycloalkyl; (11) halo; (12) C$_{1-12}$ heterocyclyl (e.g., C$_{1-12}$ heteroaryl); (13) (C$_{1-12}$ heterocyclyl)oxy; (14) hydroxyl; (15) nitro; (16) C$_{1-20}$ thioalkoxy (e.g., C$_{1-6}$ thioalkoxy); (17) —(CH$_2$)$_q$CO$_2$R$^{A'}$, where q is an integer from zero to four, and R$^{A'}$ is selected from the group consisting of (a) C$_{1-6}$ alkyl, (b) C$_{6-10}$ aryl, (c) hydrogen, and (d) C$_{1-6}$ alk-C$_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) C$_{1-6}$ alkyl, (c) C$_{6-10}$ aryl, and (d) C$_{1-6}$ alk-C$_{6-10}$ aryl; (19) —(CH$_2$)$_q$SO$_2$R$^{D'}$, where q is an integer from zero to four and where R$^{D'}$ is selected from the group consisting of (a) alkyl, (b) C$_{6-10}$ aryl, and (c) alk-C$_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) C$_{1-6}$ alkyl, (c) C$_{6-10}$ aryl, and (d) C$_{1-6}$ alk-C$_{6-10}$ aryl; (21) thiol; (22) C$_{6-10}$ aryloxy; (23) C$_{3-8}$ cycloalkoxy; (24) C$_{6-10}$ aryl-C$_{1-6}$ alkoxy; (25) C$_{1-6}$ alk-C$_{1-12}$ heterocyclyl (e.g., C$_{1-6}$ alk-C$_{1-12}$ heteroaryl); (26) C$_{2-20}$ alkenyl; and (27) C$_{2-20}$ alkynyl. In some embodiments, each of these groups can be further substituted as described herein. For example, the alkylene group of a C$_1$-alkaryl or a C$_1$-alkheterocyclyl can be further substituted with an oxo group to afford the respective aryloyl and (heterocyclyl)oyl substituent group.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as C$_{1-6}$ alk-C$_{6-10}$ aryl, C$_{1-10}$ alk-C$_{6-10}$ aryl, or C$_{1-20}$ alk-C$_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a C$_{1-6}$ alkylene, unless otherwise noted, and the attached chemical structure is as defined herein.

The term "azido" represents an —N$_3$ group, which can also be represented as —N=N=N.

The terms "carbocyclic" and "carbocyclyl," as used herein, refer to an optionally substituted C$_{3-12}$ monocyclic, bicyclic, or tricyclic non-aromatic ring structure in which the rings are formed by carbon atoms. Carbocyclic structures include cycloalkyl, cycloalkenyl, and cycloalkynyl groups.

The "carbocyclylalkyl" group, which as used herein, represents a carbocyclic group, as defined herein, attached to the parent molecular group through an alkylene group, as defined herein. Exemplary unsubstituted carbocyclylalkyl groups are from 7 to 30 carbons (e.g., from 7 to 16 or from 7 to 20 carbons, such as $C_{1-6}$ alk-$C_{6-10}$ carbocyclyl, $C_{1-10}$ alk-$C_{6-10}$ carbocyclyl, or $C_{1-20}$ alk-$C_{6-10}$ carbocyclyl). In some embodiments, the alkylene and the carbocyclyl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "carbonyl," as used herein, represents a C(O) group, which can also be represented as C=O.

The term "carboxy," as used herein, means —$CO_2H$.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxyl; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "cycloalkylalkyl" group, which as used herein, represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6-, or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

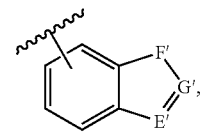

where

E' is selected from the group consisting of —N— and —CH—; F' is selected from the group consisting of —N═CH—, —NH—CH$_2$—, —NH—C(O)—, —NH—, —CH═N—, —CH$_2$—NH—, —C(O)—NH—, —CH═CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxyl; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "hydrocarbon," as used herein, represents a group consisting only of carbon and hydrogen atoms.

The term "hydroxyl," as used herein, represents an —OH group. In some embodiments, the hydroxyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such as methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxycarbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methylphenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The prefix "perfluoro," as used herein, represents anyl group, as defined herein, where each hydrogen radical bound to the alkyl group has been replaced by a fluoride radical. For example, perfluoroalkyl groups are exemplified by trifluoromethyl, pentafluoroethyl, and the like.

The term "protected hydroxyl," as used herein, refers to an oxygen atom bound to an O-protecting group.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein. represents an —SH group.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As is known in the art, "affinity" is a measure of the tightness with which a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

It will be understood that the term "binding" as used herein, typically refers to association (e.g., non-covalent or covalent) between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

The affinity of a molecule X for its partner Y can generally be represented by the dissociation constant ($K_D$). Affinity can be measured by common methods known in the art, including those described herein. Specific illustrative and exemplary embodiments for measuring binding affinity are described below. The term "$K_D$," as used herein, is intended to refer to the dissociation equilibrium constant of a particular compound-protein or complex-protein interaction. Typically, the compounds of the invention bind to presenter proteins with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower, e.g., when determined by surface plasmon resonance (SPR) technology using the presenter protein as the analyte and the compound as the ligand. The presenter protein/compound complexes of the invention bind to target proteins (e.g., a eukaryotic target protein such as a mammalian target protein or a fungal target protein or a prokaryotic target protein such as a bacterial target protein) with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower, e.g., when determined by surface plasmon resonance (SPR) technology using the target protein as the analyte and the complex as the ligand.

As used herein, the term "cross-linking group" refers to a group comprising a reactive functional group capable of chemically attaching to specific functional groups (e.g., primary amines, sulfhydryls) on proteins or other molecules. A "moiety capable of a chemoselective reaction with an amino acid," as used herein refers to a moiety comprising a reactive functional group capable of chemically attaching to a functional group of a natural or non-natural amino acid (e.g., primary and secondary amines, sulfhydryls, alcohols, carboxyl groups, carbonyls, or triazole forming functional groups such as azides or alkynes). Examples of cross-linking groups include sulfhydryl-reactive cross-linking groups (e.g., groups comprising maleimides, haloacetyls, pyridyldisulfides, thiosulfonates, or vinylsulfones), amine-reactive cross-linking groups (e.g., groups comprising esters such as NHS esters, imidoesters, and pentafluorophenyl esters, or hydroxymethylphosphine), carboxyl-reactive cross-linking groups (e.g., groups comprising primary or secondary amines, alcohols, or thiols), carbonyl-reactive cross-linking groups (e.g., groups comprising hydrazides or alkoxyamines), and triazole-forming cross-linking groups (e.g., groups comprising azides or alkynes).

As used herein, the term "complex" refers to a group of two or more compounds and/or proteins which are bound together through a binding interaction (e.g., a non-covalent interaction, such as a hydrophobic effect interaction, an electrostatic interaction, a van der Waals interaction, or π-effect interaction). Examples of complexes are "presenter protein/conjugate complex" and "target protein/conjugate complex" which include a conjugate of the invention bound to a presenter protein or a target protein.

As used herein, the term "conjugate" refers to a compound formed by the joining (e.g., via a covalent bond forming reaction) of two or more chemical compounds (e.g., a compound including a cross-linking group and a protein such as a target protein or a presenter protein).

As used herein, an atom that "participates in binding" is within 4 Å of the entity to which they bind or connects to an atom that is with 4 Å of the entity to which they bind.

The term "presenter protein" refers to a protein that binds to a small molecule to form a complex that binds to and modulates the activity of a target protein (e.g., a eukaryotic target protein such as a mammalian target protein or a fungal target protein or a prokaryotic target protein such as a bacterial target protein). In some embodiments, the presenter protein is a relatively abundant protein (e.g., the presenter protein is sufficiently abundant that participation in a tripartite complex does not substantially impact the biological role of the presenter protein in a cell and/or viability or other attributes of the cell). In certain embodiments, the presenter protein is a protein that has chaperone activity within a cell. In some embodiments, the presenter protein is a protein that has multiple natural interaction partners within a cell. In certain embodiments, the presenter protein is one which is known to bind a small molecule to form a binary complex that is known to or suspected of binding to and modulating the biological activity of a target protein.

The term "presenter protein binding moiety" refers to a group of atoms and the moieties attached thereto (e.g., atoms within 20 atoms such as, atoms within 15 atoms, atoms within 10, atoms within 5 atoms) that participate in binding to a presenter protein such that the compound specifically binds to said presenter protein, for example, with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM) or inhibits the peptidyl-prolyl isomerase activity of the presenter protein, for example, with an $IC_{50}$ of less than 1 µM (e.g., less than 0.5 µM, less than 0.1 µM, less than 0.05 µM, less than 0.01 µM). It will be understood that the presenter protein binding moiety does not necessarily encompass the entirety of atoms in the compound that interact with the presenter protein. It will also be understood that one or more atoms of the presenter protein binding moiety may be within the target protein binding moiety (e.g., eukaryotic target protein binding moiety such as mammalian target protein binding moiety or fungal target protein binding moiety or prokaryotic target protein binding moiety such as a bacterial target protein binding moiety).

As used herein, "FKBP binding moiety" refers to a presenter protein binding moiety that is selective for presenter proteins in the FKBP family of proteins (e.g., FKBP12, FKBP12.6, FKBPP13, FKBP25, FKBP51, or FKBP52). A "selective FKBP binding moiety," as used herein, refers to a binding moiety that is specific for one or more (e.g., two, three, four, five) members of the FKBP family over all other members of the FKBP family. A "non-selective FKBP binding moiety," as used herein, refers to a binding moiety that has comparable affinity (within 2-fold, within 3-fold, within 4-fold, within 5-fold, within 10-fold) for all members of the FKBP family.

The term "protein binding moiety" refers to a group of atoms and the moieties attached thereto (e.g., atoms within 20 atoms such as, atoms within 15 atoms, atoms within 10, atoms within 5 atoms) that participate in binding to a protein (e.g., a presenter protein or a target protein) such that the compound specifically binds to said protein, for example, with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM) or inhibits the peptidyl-prolyl isomerase activity of the presenter protein, for example, with an $IC_{50}$ of less than 1 µM (e.g., less than 0.5 µM, less than 0.1 µM, less than 0.05 µM, less than 0.01 µM). It will be understood that the protein binding moiety does not necessarily encompass the entirety of atoms in the compound that interact with the protein.

As used herein, the term "react" refers to a process in which atoms of the same or different elements rearrange themselves to form a new substance. For example, the formation of a covalent bond between two atoms such as the reaction between a reactive amino acid on a protein and a cross-linking group to form a covalent bond. A reaction may be measured by any method known in the art, for example, formation of a reaction product can be determined by LC-MS or NMR.

As used herein, the term "reactive amino acid" refers to a natural or non-natural amino acid comprising a functional group (e.g., a nucleophilic functional group) capable of chemically attaching to specific functional groups (e.g., a cross-linking group). Examples of reactive amino acids include cysteine, lysine, serine, and amino acids having azides on the side chain. "Non-reactive amino acids" refers to natural or non-natural amino acids that do not contain a functional group capable of chemically attaching to specific functional groups. Examples of non-reactive amino acids include valine, alanine, isoleucine, threonine, and leucine.

The term "reference" is often used herein to describe a standard or control compound, individual, population, sample, sequence or value against which a compound, individual, population, sample, sequence or value of interest is compared. In some embodiments, a reference compound, individual, population, sample, sequence or value is tested and/or determined substantially simultaneously with the testing or determination of the compound, individual, population, sample, sequence or value of interest. In some embodiments, a reference compound, individual, population, sample, sequence or value is a historical reference, optionally embodied in a tangible medium. Typically, as would be understood by those skilled in the art, a reference compound, individual, population, sample, sequence or value is determined or characterized under conditions comparable to those utilized to determine or characterize the compound, individual, population, sample, sequence or value of interest.

As used herein, the term "solvent exposed amino acid" refers to an amino acid that is accessible to the solvent surrounding the protein. In some embodiments, a solvent exposed amino acid is an amino acid that when substituted does not substantially change the three-dimensional structure of the protein.

As used herein, the terms "specific binding" or "specific for" or "specific to" refer to an interaction between a binding agent and a target entity. As will be understood by those of ordinary skill, an interaction is considered to be "specific" if it is favored in the presence of alternative interactions, for example, binding with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM). In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent.

The term "specific" when used with reference to a compound having an activity, is understood by those skilled in the art to mean that the compound discriminates between potential target entities or states. For example, in some embodiments, a compound is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, speicifcity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "does not substantially bind" to a particular protein as used herein can be exhibited, for example, by a molecule or portion of a molecule having a $K_D$ for the target of $10^{-4}$ M or greater, alternatively $10^{-5}$ M or greater, alternatively $10^{-6}$ M or greater, alternatively $10^{-7}$ M or greater, alternatively $10^{-8}$ M or greater, alternatively $10^{-9}$ M or greater, alternatively $10^{-10}$ M or greater, alternatively $10^{-11}$ M or greater, alternatively $10^{-12}$ M or greater, or a $K_D$ in the range of $10^{-4}$ M to $10^{-12}$ M or $10^{-6}$ M to $10^{-10}$ M or $10^{-7}$ M to $10^{-9}$ M.

The term "target protein" refers to any protein that participates in a biological pathway associated with a disease, disorder or condition. In some embodiments, the target protein is not mTOR or calcineurin. In some embodiments, the target protein is capable of forming a tripartite complex with a presenter protein and a small molecule. In some embodiments, a target protein is a naturally-occurring protein; in some such embodiments, a target protein is naturally found in certain mammalian cells (e.g., a mammalian target protein), fungal cells (e.g., a fungal target protein), bacterial cells (e.g., a bacterial target protein) or plant cells (e.g., a plant target protein). In some embodiments, a target protein is characterized by natural interaction with one or more natural presenter protein/natural small molecule complexes. In some embodiments, a target protein is characterized by natural interactions with a plurality of different natural presenter protein/natural small molecule complexes; in some such embodiments some or all of the complexes utilize the same presenter protein (and different small molecules). In some embodiments, a target protein does not substantially bind to a complex of cyclosporin, rapamycin, or FK506 and a presenter protein (e.g., FKBP). Target proteins can be naturally occurring, e.g., wild type. Alternatively, the target protein can vary from the wild type protein but still retain biological function, e.g., as an allelic variant, a splice mutant or a biologically active fragment. Exemplary mammalian target proteins are GTPases, GTPase activating protein, Guanine nucleotide-exchange factor, heat shock proteins, ion channels, coiled-coil proteins, kinases, phosphatases, ubiquitin ligases, transcription factors, chromatin modifier/remodelers, proteins with classical protein-protein interaction domains and motifs, or any other proteins that participate in a biological pathway associated with a disease, disorder or condition.

In some embodiments, the target protein is a modified target protein. A modified target protein can include an amino acid insertion, deletion, or substitution, either conservative or non-conservative (e.g., D-amino acids, desamino acids) in the protein sequence (e.g., where such changes do not substantially alter the biological activity of the polypeptide). In particular, the addition of one or more cysteine residues to the amino or carboxy terminus of any of the polypeptides of the invention can facilitate conjugation of these proteins by, e.g., disulfide bonding. In some embodiments, one or more reactive amino acid residues (e.g., cysteines) are removed to decrease the number of possible conjugation sites on the protein. Amino acid substitutions can be conservative (i.e., wherein a residue is replaced by another of the same general type or group) or non-conservative (i.e., wherein a residue is replaced by an amino acid of another type). In addition, a naturally occurring amino acid can be substituted for a non-naturally occurring amino acid (i.e., non-naturally occurring conservative amino acid substitution or a non-naturally occurring non-conservative amino acid substitution).

The term "target protein binding moiety" refers to a group of ring atoms and the moieties attached thereto (e.g., atoms within 20 atoms such as, atoms within 15 atoms, atoms within 10 atoms, within 5 atoms) that participate in binding to a target protein (e.g., a eukaryotic target protein such as a mammalian target protein or a fungal target protein or a prokaryotic target protein such as a bacterial target protein) when the compound is in a complex with a presenter protein. It will be understood that the target protein binding moiety does not necessarily encompass the entirety of atoms in the compound that interact with the target protein. It will also be understood that one or more atoms of the presenter protein binding moiety may also be present in the target protein binding moiety.

The term "traditional binding pocket" refers to cavities or pockets on a protein structure with physiochemical and/or geometric properties comparable to proteins whose activity has been modulated by one or more small molecules. In some embodiments, a traditional binding pocket is a well-defined pocket with a volume greater than 1000 $Å^3$. Those of ordinary skill in the art are familiar with the concept of a traditional binding pocket and, moreover are aware of its relationship to "druggability". In certain embodiments, a protein is considered to not have a traditional binding pocket if it is undruggable, as defined herein.

The term "undruggable target" refers to proteins that are not members of a protein family which is known to be targeted by drugs and/or does not possess a binding site that is suitable for high-affinity binding to a small molecule. Methods for determining whether a target protein is undruggable are known in the art. For example, whether a target protein is undruggable may be determined using an structure-based algorithim, such as those used by the program DOGSITESCORER® (Universitat Hamburg, Hamburg, Germany) that assesses druggability based on parameters computed for binding pockets on a protein including volume, surface area, lipophilic surface area, depth, and/or hydrophobic ratio.

BRIEF DESCRIPTION OF THE DRAWINGS

FIG. 3A) SEC purification profile. Dashed blue lines indicate the peak corresponding to elution of the $KRAS_{GTP/S39C}$ lite/C2-Holt/FKBP12 ternary complex; FIG. 3B) SDS-PAGE analysis of SEC elution peaks. Dashed blue lines correspond with the fractions collected for the $KRAS_{GTP/S39C}$ lite/C2-Holt/FKBP12 elution peak.

FIG. 4 is an image illustrating SEC profile and SDS-PAGE analysis of the elution peaks confirm the formation of $KRAS_{GDP/S39C}$ lite/SFAC4DS/CypA$_{C52S}$ complex.

FIG. 7A) Ribbon representation showing FKBP12, $KRAS_{GTP/S39C}$ and the ligand. Fo-Fc electron density at 3 σ shown is shown for the ligand in the close-up view. FIG. 7B) Surface representation of the complex with atoms within 4 Å proximity to either ligand or partner protein colored in red.

FIG. 8 is an image illustrating the crystal structure of CypA$_{C52S}$-SFAC4DS-$KRAS_{GDP/S39C}$.

FIG. 9A illustrates that the crystal contains two complex molecules of FKBP12-C3SLF-PTP1B$_{S187C}$ in the asymmetric unit. FIG. 9B illustrates that the buried surface area of PTP1B$_{S187C}$ is 427 Å$^2$ and the buried surface area of C3-SLF is 615 Å$^2$.

FIG. 10 is an image illustrating the crystal structure of MCL1$_{S245C}$/C3SLF/FKBP52.

FIG. 13 is an image illustrating ITC measurements for the binding of FKBP12-Compound 1 and FKBP12-Compound 2 binary complexes to CEP250.

FIGS. 17A-17C are images illustrating the 2D 1H-15N TROSY-HSQC spectrum of KRAS$_{G12C\text{-}GTP}$ (FIG. 17A), the addition of a stoichiometric amount of CYPA (FIG. 17B), and KRAS and CYPA alone (FIG. 17C).

DETAILED DESCRIPTION OF CERTAIN EMBODIMENTS

Figure 1:
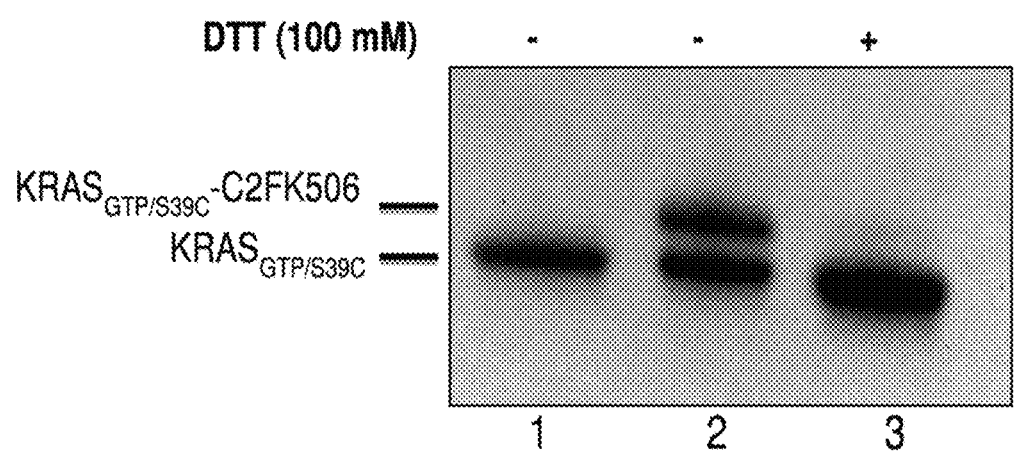
FIG. 1 is an image illustrating SDS-PAGE analysis of $KRAS_{GTP/S39C}$ lite/C2-FK506 conjugates. Lane 1: $KRAS_{GTP/S39C}$ lite; Lane 2: $KRAS_{GTP/S39C}$ lite/C2-FK506 reaction mixture; Lane 3: $KRAS_{GTP/S39C}$ lite/C2-FK506 reaction mixture+100 mM DTT.

Small molecules are limited in their targeting ability because their interactions with the target are driven by adhesive forces, the strength of which is roughly proportional to contact surface area. Because of their small size, the only way for a small molecule to build up enough intermolecular contact surface area to effectively interact with a target protein is to be literally engulfed by that protein. Indeed, a large body of both experimental and computational data supports the view that only those proteins having a hydrophobic "pocket" on their surface are capable of binding small molecules. In those cases, binding is enabled by engulfment.

Nature has evolved a strategy that allows a small molecule to interact with target proteins at sites other than hydrophobic pockets. This strategy is exemplified by naturally occurring immunosuppressive drugs cyclosporine A, rapamycin, and FK506. The biological activity of these drugs involves the formation of a high-affinity complex of the small molecule with a small presenting protein. The composite surface of the small molecule and the presenting protein engages the target. Thus, for example, the binary complex formed between cyclosporin A and cyclophilin A targets calcineurin with high affinity and specificity, but neither cyclosporin A or cyclophilin A alone binds calcineurin with measurable affinity.

Many important therapeutic targets exert their function by complexation with other proteins. The protein/protein interaction surfaces in many of these systems contain an inner core of hydrophobic side chains surrounded by a wide ring of polar residues. The hydrophobic residues contribute nearly all of the energetically favorable contacts, and hence this cluster has been designated as a "hotspot" for engagement in protein-protein interactions. Importantly, in the aforementioned complexes of naturally occurring small molecules with small presenting proteins, the small molecule provides a cluster of hydrophobic functionality akin to a hotspot, and the protein provides the ring of mostly polar residues. In other words, presented small molecule systems mimic the surface architecture employed widely in natural protein/protein interaction systems.

Nature has demonstrated the ability to reprogram the target specificity of presented small molecules—portable hotspots-through evolutionary diversification. In the best characterized example, the complex formed between FK506 binding protein (FKBP) and FK506 targets calcineurin. However, FKBP can also form a complex with the related molecule rapamycin, and that complex interacts with a completely different target, TorC1. To date, no methodology has been developed to reprogram the binding and modulating ability of presenter protein/ligand interfaces so that they can interact with and modulate other target proteins that have previously been considered undruggable.

In addition, it is well established that some drug candidates fail because they modulate the activity of both the intended target and other non-intended proteins as well. The problem is particularly daunting when the drug binding site of the target protein is similar to binding sites in non-target proteins. The insulin like growth factor receptor (IGF-1R), whose ATP binding pocket is structurally similar to the binding pocket of the non-target insulin receptor (IR), is one such example. Small molecule development candidates that were designed to target IGF-1R typically have the unacceptable side effect of also modulating the insulin receptor. However, structural dissimilarities do exist between these two proteins in the regions surrounding the ATP binding pocket. Despite such knowledge, no methodology exists to date to take advantage of those differences and develop drugs that are specific to IGF-1R over IR.

The present disclosure provides methods and reagents useful for analyzing protein-protein interfaces such as the interface between a presenter protein (e.g., a member of the FKBP family, a member of the cyclophilin family, or PIN1) and a target protein. In some embodiments, the target and/or presenter proteins are intracellular proteins. In some embodiments, the target and/or presenter proteins are mammalian proteins. In some embodiments, these methods and reagents may be useful for identifying target proteins amenable to inhibition or activation by forming a complex with a presenter protein and a small molecule. In some embodiments, these methods and reagents may be useful in identifying compounds capable of inhibiting or activating target proteins by forming a complex with a presenter protein and the target protein.

Compounds and Conjugates

The disclosure provides compounds including a protein binding moiety (e.g., a presenter protein binding moiety or target protein binding moiety) and a cross-linking group. The invention also features conjugates including a protein binding moiety conjugated to a protein, e.g., a presenter protein binding moiety conjugated to a target protein or a target protein binding moiety conjugated to a presenter protein.

The invention also features compounds of Formula VII:

A-L-B    Formula VII wherein A comprises the structure of Formula VIII:

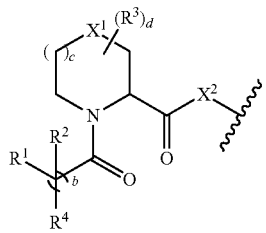

Formula VIII

In some embodiments, the compound of the invention is:

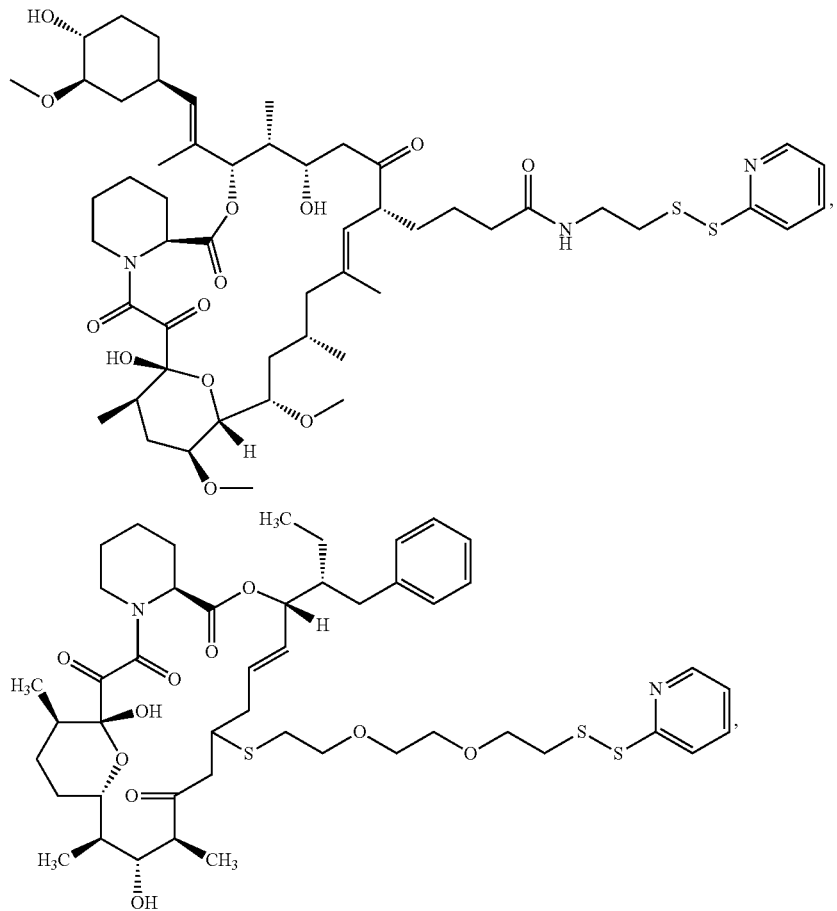

57 58
-continued
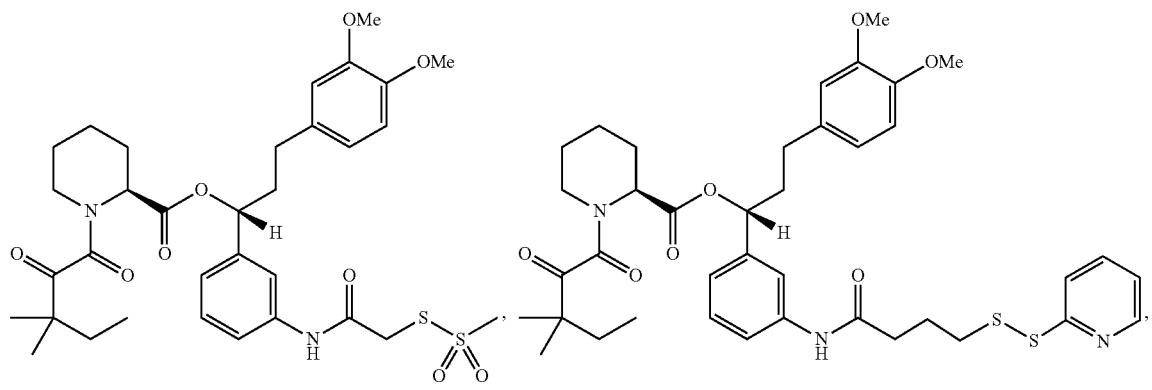
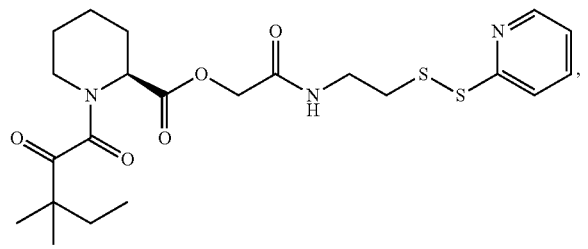
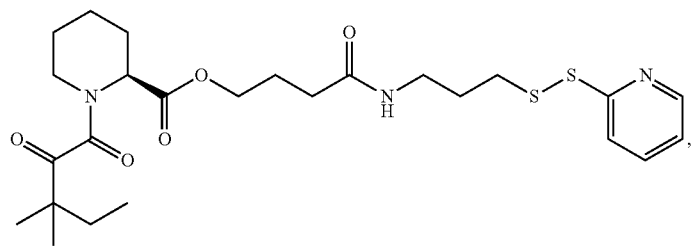
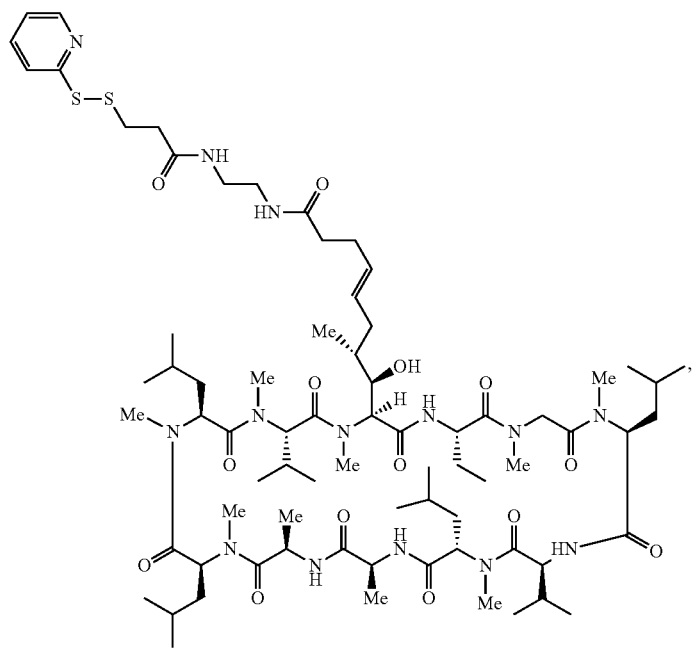

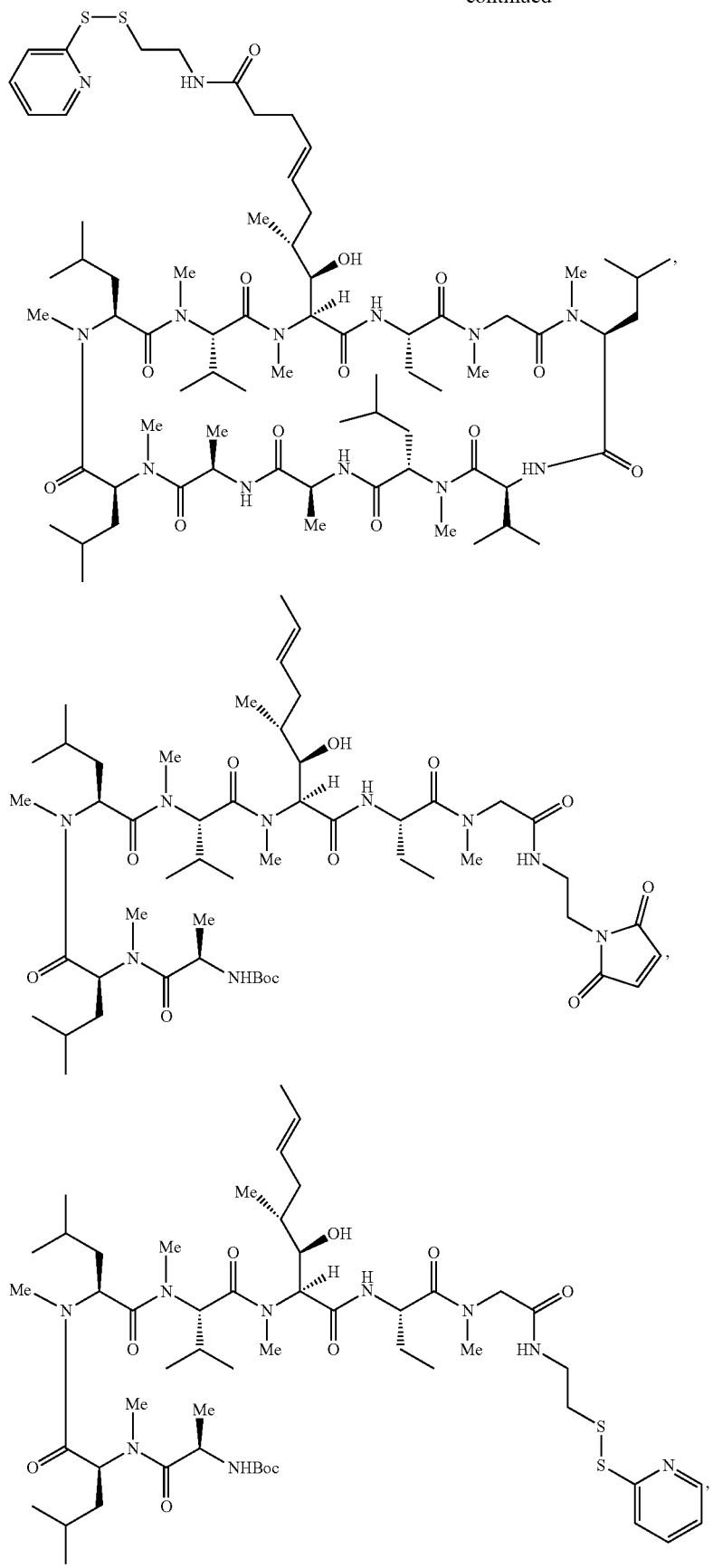

61
62
-continued
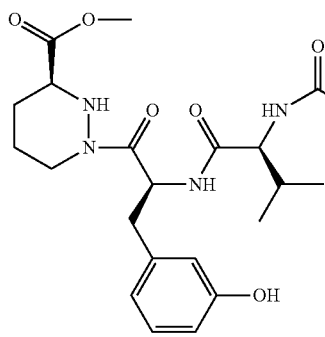
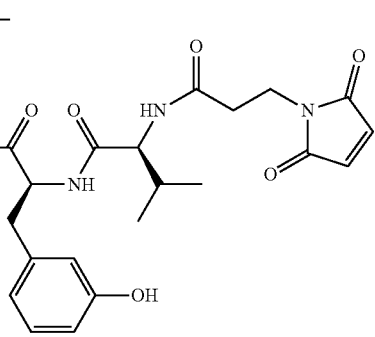
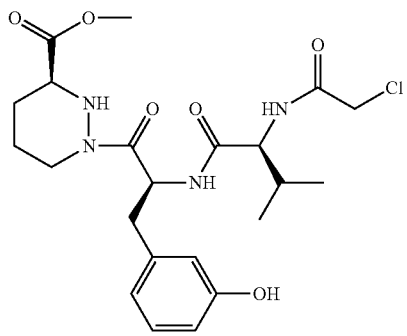
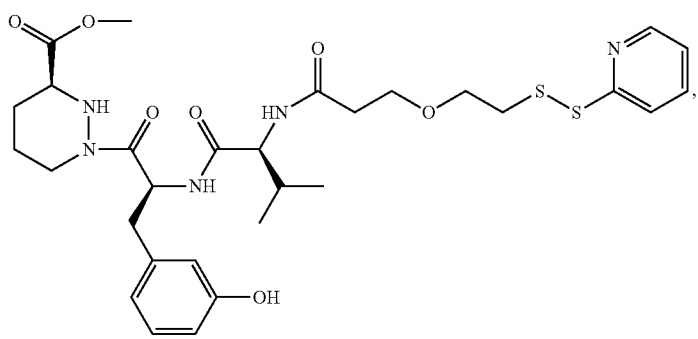
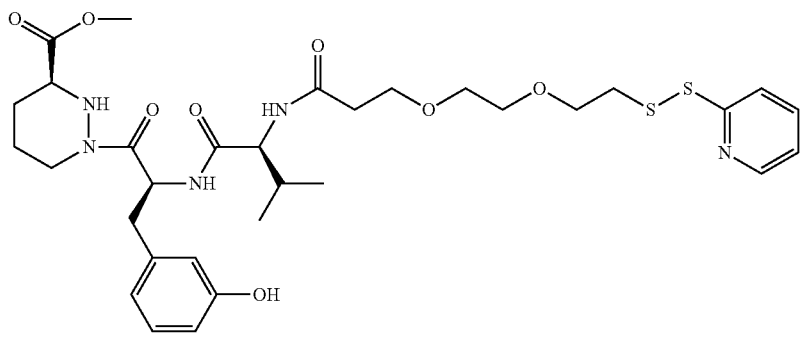
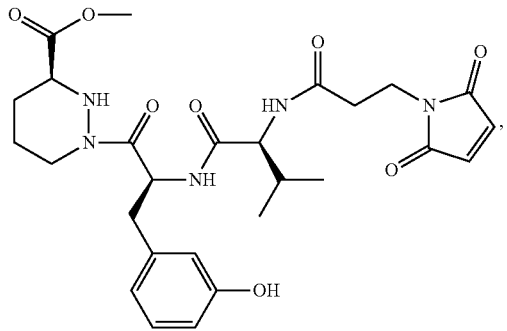

-continued

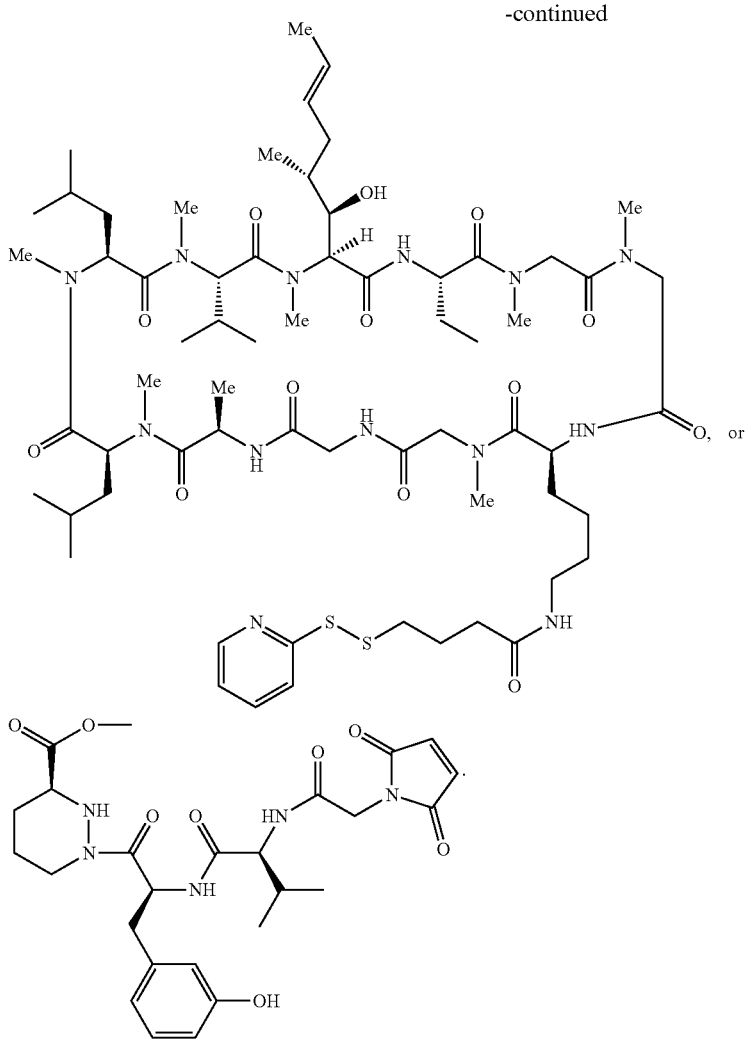

Cross-linking Groups

In some embodiments, compounds of the invention include a cross-linking group. A cross-linking group refers to a group comprising a reactive functional group capable of chemically attaching to specific functional groups (e.g., primary amines, sulfhydryls) on proteins or other molecules. Examples of cross-linking groups include sulfhydryl-reactive cross-linking groups (e.g., groups comprising maleimides, haloacetyls, pyridyldisulfides, thiosulfonates, or vinylsulfones), amine-reactive cross-linking groups (e.g., groups comprising esters such as NHS esters, imidoesters, and pentafluorophenyl esters, or hydroxymethylphosphine), carboxyl-reactive cross-linking groups (e.g., groups comprising primary or secondary amines, alcohols, or thiols), carbonyl-reactive cross-linking groups (e.g., groups comprising hydrazides or alkoxyamines), and triazole-forming cross-linking groups (e.g., groups comprising azides or alkynes).

Exemplary cross-linking groups include 2'-pyridyldisulfide, 4'-pyridyldisulfide iodoacetyl, maleimide, thioesters, alkyldisulfides, alkylamine disulfides, nitrobenzoic acid disulfide, anhydrides, NHS esters, aldehydes, alkyl chlorides, alkynes, and azides.

Presenter Protein Binding Moieties

In some embodiments, compounds of the invention include a presenter protein binding moiety. In some embodiments, a presenter protein binding moiety includes a group of atoms (e.g., 5 to 20 atoms, 5 to 10 atoms, 10 to 20 atoms) and may include any moieties attached thereto (e.g., atoms within 20 atoms, atoms within 15 atoms, atoms within 10 atoms, atoms within 5 atoms) that participate in binding to a presenter protein such that a provided compound specifically binds to said presenter protein, for example, with a $K_D$ of less than 10 μM (e.g., less than 5 μM, less than 1 μM, less than 500 nM, less than 200 nM, less than 100 nM, less than 75 nM, less than 50 nM, less than 25 nM, less than 10 nM) or inhibits the peptidyl-prolyl isomerase activity of the presenter protein, for example, with an $IC_{50}$ of less than 1 μM (e.g., less than 0.5 μM, less than 0.1 μM, less than 0.05 μM, less than 0.01 μM). In some embodiments, the presenter protein binding moiety does not encompass the entirety of atoms in a provided compound that interact with the presenter protein. In certain embodiments, one or more atoms of the presenter protein binding moiety do not interact with the presenter protein.

In some embodiments, a presenter protein binding moiety includes a N-acyl proline moiety, a N-acyl-pipecolic acid moiety, a N-acyl 3-morpholino-carboxylic acid moiety, and/or a N-acyl piperzic acid moiety (e.g., with acylation on either nitrogen atom. In certain embodiments, a presenter protein binding moiety includes a N-acyl-pipecolic acid moiety. In some embodiments, a presenter protein binding moiety includes a N-acyl proline moiety. In certain embodiments, a presenter protein binding moiety includes a N-acyl 3-morpholino-carboxylic acid moiety. In some embodiments, a presenter protein binding moiety includes a N-acyl piperzic acid moiety.

In some embodiments, at least one atom of a presenter protein binding moiety participates in binding with one or more (e.g., two, three, four, five, six, seven, eight, nine, ten, eleven, twelve, thirteen, fourteen, or fifteen) of Tyr 27, Phe 37, Asp 38, Arg 41, Phe 47, Gln 54, Glu 55, Val 56, Ile 57, Trp 60, Ala 82, Try 83, His 88, Ile 92, and/or Phe 100 of FKBP12. In some embodiments, at least one at of a presenter protein binding moiety participates in binding with at least one (e.g., two, three, or four) of Arg 41, Gln 54, Glu 55, and/or Ala 82 of FKBP12.

In some embodiments, a presenter protein binding moiety has a structure according to Formula II-IV:

In some embodiments, a presenter protein binding moiety includes or consists of the structure:

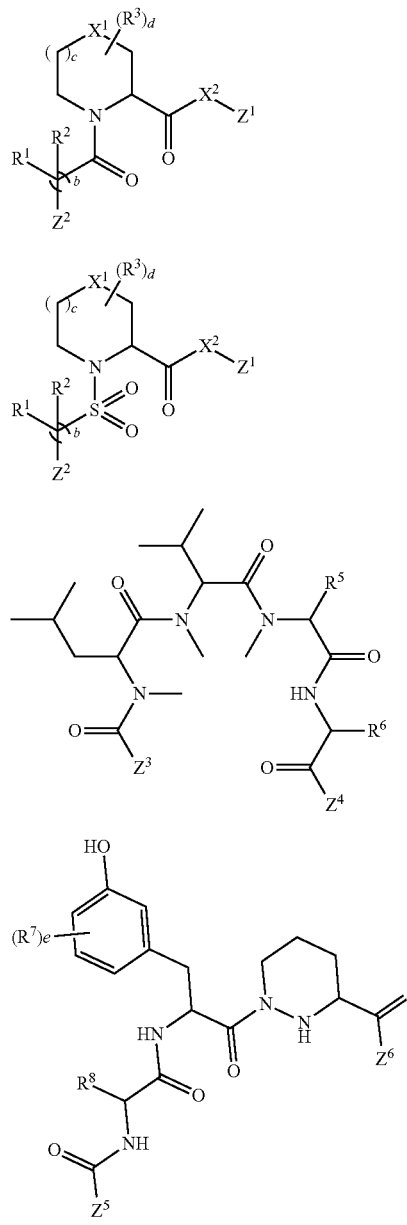

Formula IIa

Formula IIb

Formula III

Formula IV

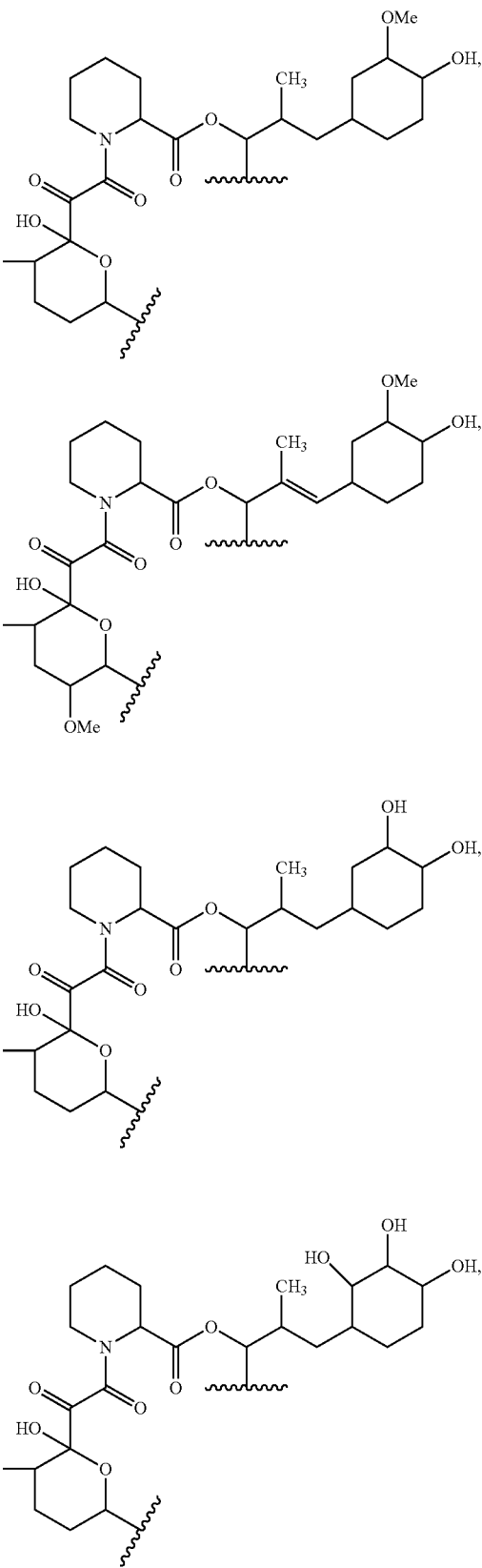

67
-continued
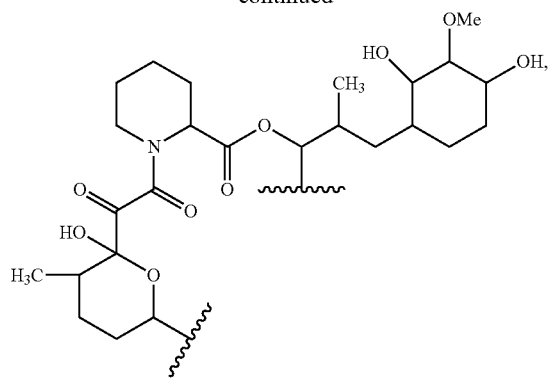
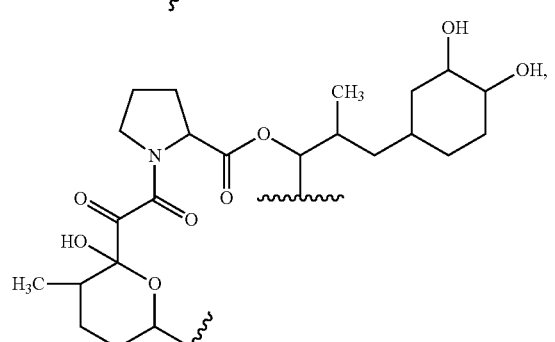
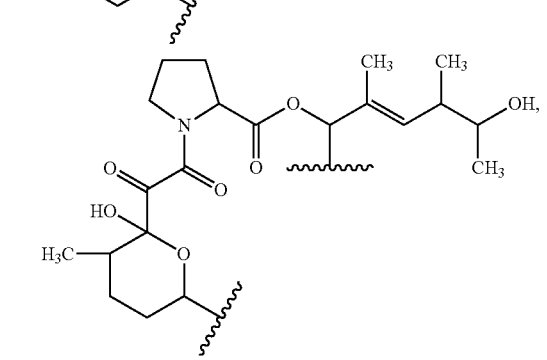
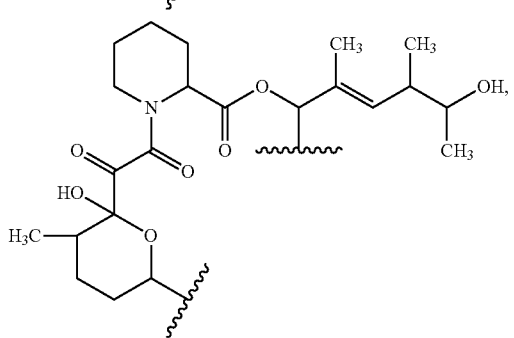
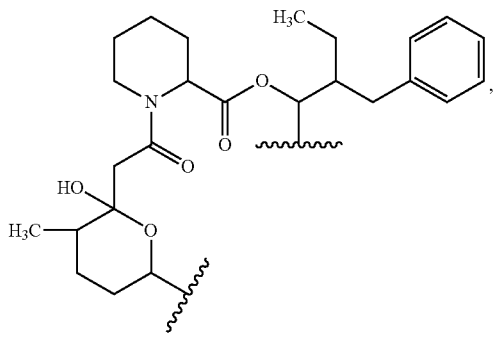
68
-continued
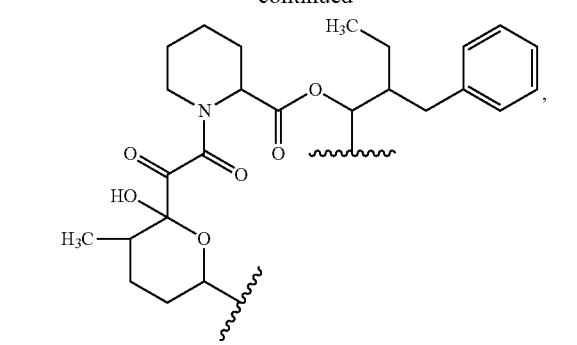
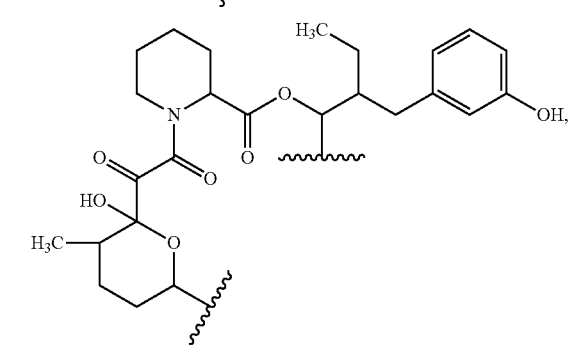
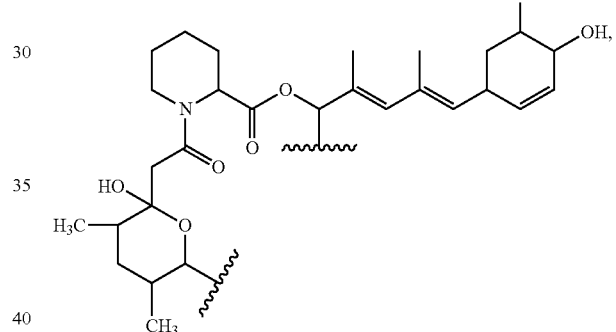
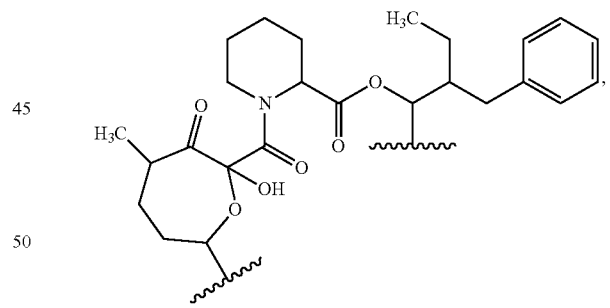
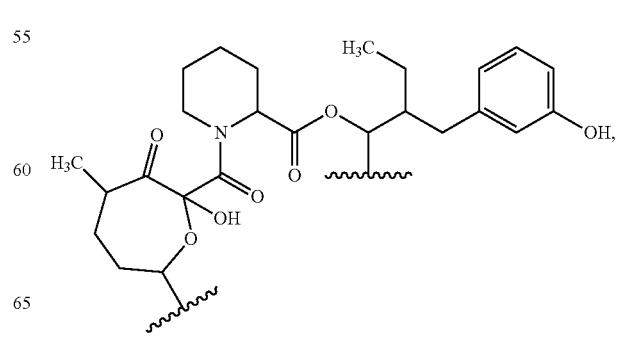

69
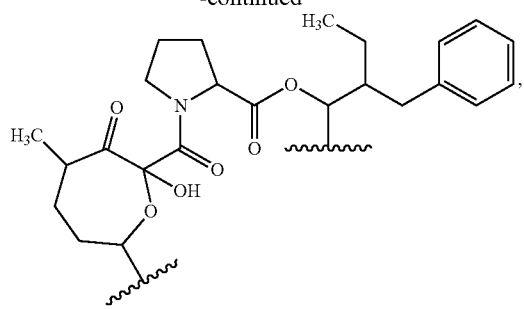
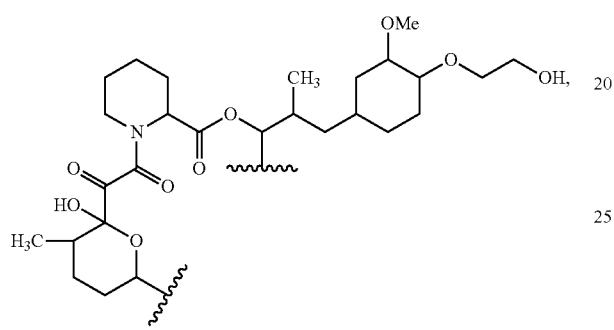
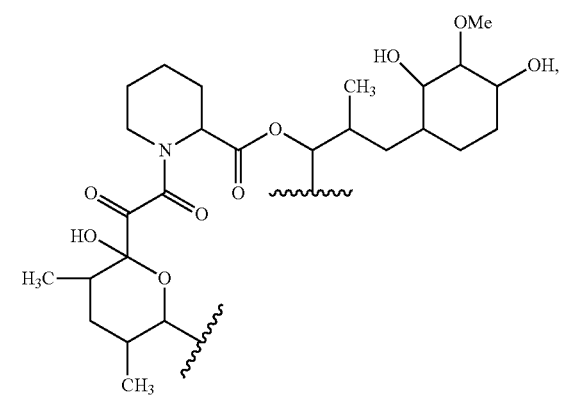
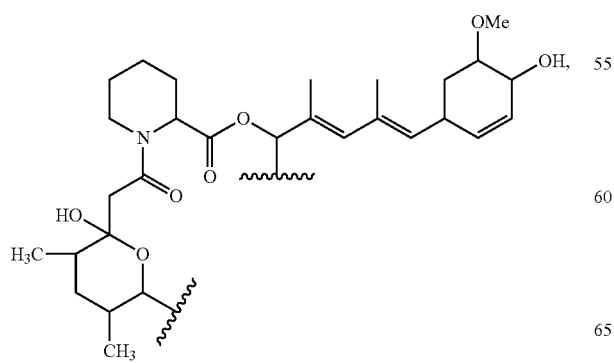
70
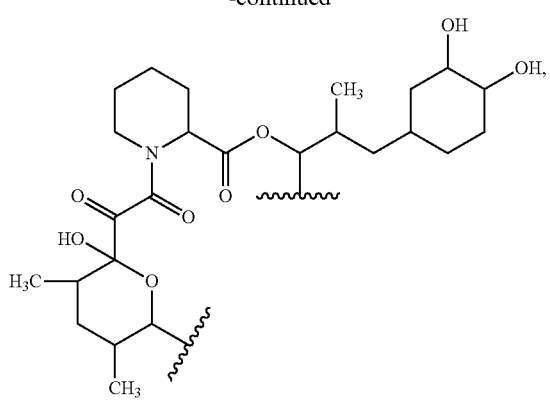
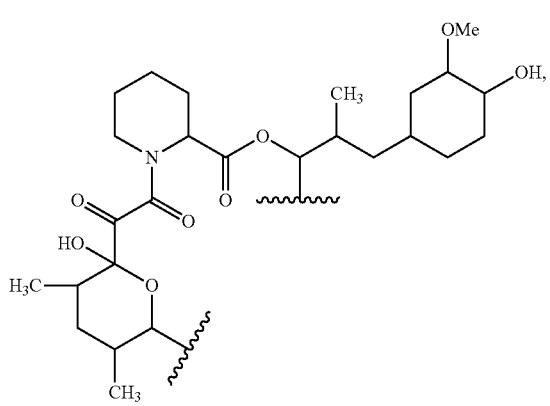
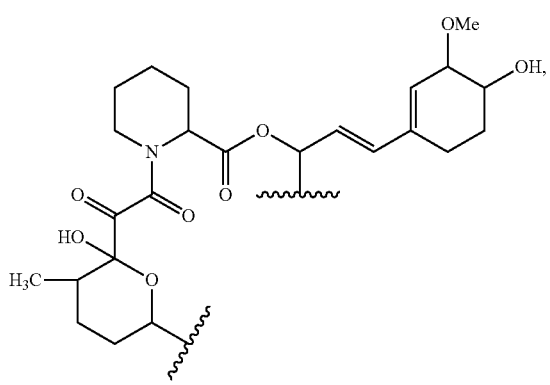
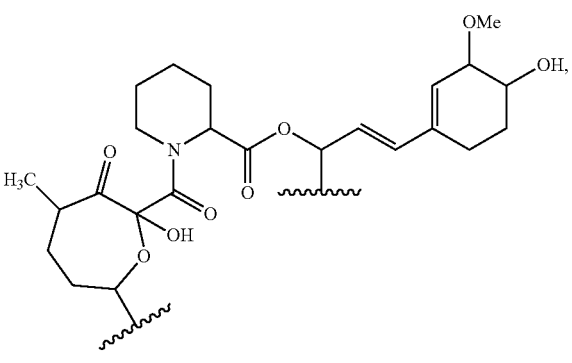

71
-continued
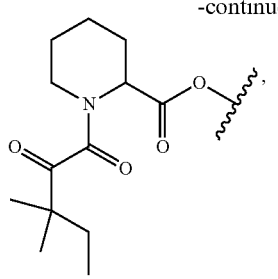
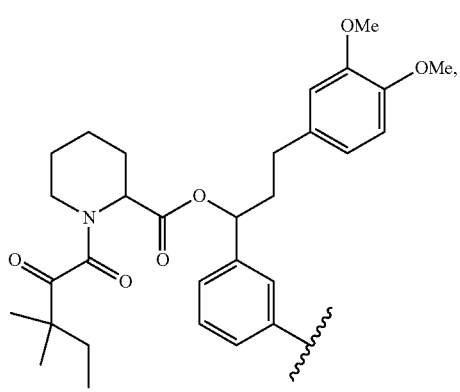
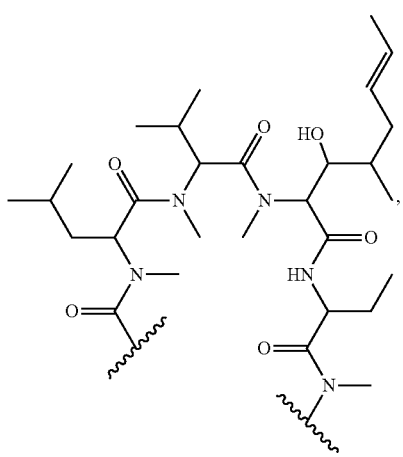
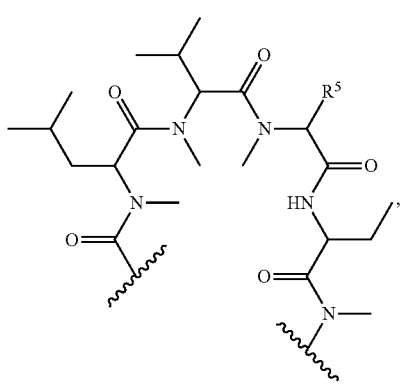
72
-continued
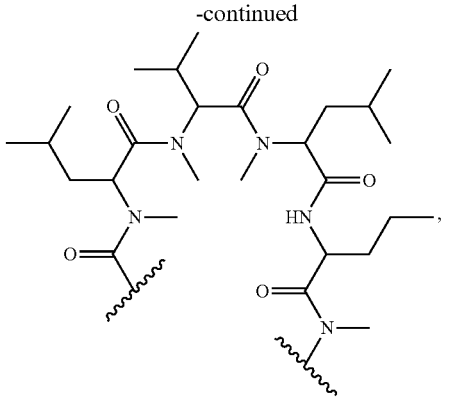
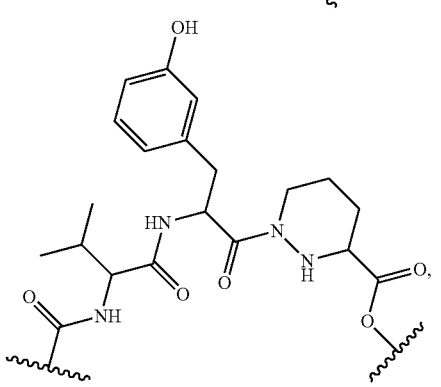
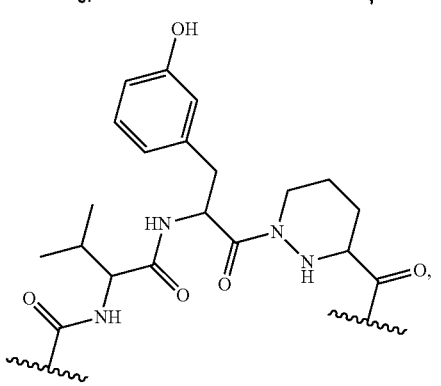
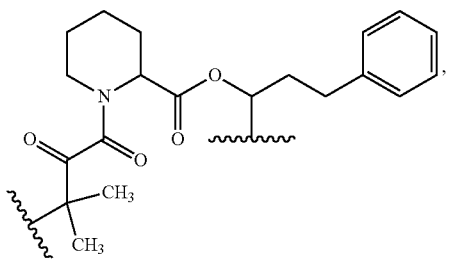
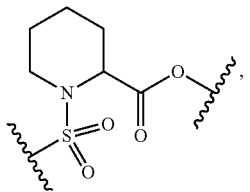

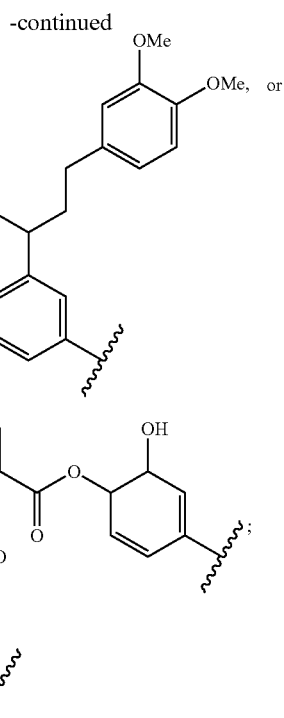

or a stereoisomer thereof.

A presenter protein can bind to an atom in a presenter protein binding moiety. Alternatively or additionally, a presenter protein can bind to two or more atoms in a presenter protein binding moiety. In another alternative, a presenter protein bind can to a substituent attached to one or more atoms in a presenter protein binding moiety. Furthermore, in some embodiments, a presenter protein can bind to an atom in a presenter protein binding moiety and to a substituent attached to one or more atoms in a presenter protein binding moiety. In some embodiments, a presenter protein binds to a group that mimics a natural ligand of a presenter protein and wherein the group that mimics a natural ligand of a presenter protein is attached to a presenter protein binding moiety. In some embodiments, a presenter protein binds to a presenter protein and affinity of a presenter protein for a presenter protein in the binary complex is increased relative to the affinity of a presenter protein for a presenter protein in the absence of the complex. Binding in such examples is typically through, but not limited to non-covalent interactions of a presenter protein to a presenter protein binding moiety.

Target Protein Binding Moieties

In some embodiments, compounds of the invention include a target protein binding moiety (e.g., a eukaryotic target protein binding moiety such as a mammalian target protein binding moiety or a fungal target protein binding moiety or a prokaryotic target protein binding moiety such as a bacterial target protein binding moiety). In some embodiments, the target protein binding moiety includes a group of atoms (e.g., 5 to 20 atoms, 5 to 10 atoms, 10 to 20 atoms) and may include any moieties attached thereto (e.g., atoms within 20 atoms, atoms within 15 atoms, atoms within 10 atoms, atoms within 5 atoms) that specifically bind to a target protein. In some embodiments, a target protein binding moiety comprises a plurality of the atoms in the compound that interact with the target protein. In certain embodiments, one or more atoms of a target protein binding moiety do not interact with the target protein.

A target protein can bind to an atom in a target protein binding moiety. Alternatively or additionally, a target protein can bind to two or more atoms in a target protein binding moiety. In another alternative, a target protein bind can to a substituent attached to one or more atoms in a target protein binding moiety. In another alternative, a target protein can bind to an atom in a target protein binding moiety and to a substituent attached to one or more atoms in a target protein binding moiety. In another alternative, a target protein binds to a group that mimics a natural ligand of a target protein and wherein the group that mimics a natural ligand of a target protein is attached to a target protein binding moiety. In yet another alternative, a target protein binds to a presenter protein and the affinity of a target protein for a presenter protein in the binary complex is increased relative to the affinity of a target protein for a presenter protein in the absence of the complex. Binding in these examples is typically through, but not limited to non-covalent interactions of a target protein to a target protein binding moiety.

Linkers

The compounds of the invention include a linker (e.g., moiety linker joining a protein binding moiety (e.g., a presenter protein binding moiety or a target protein binding moiety) to a cross-linking group or a linker joining a protein binding moiety to a protein (e.g., a presenter protein or target protein). The linker component of the invention is, at its simplest, a bond, but may also provide a linear, cyclic, or branched molecular skeleton having pendant groups covalently linking two moieties.

In some embodiments, at least one atom of a linker participates in binding to the presenter protein and/or the target protein. In certain embodiments, at least one atom of a linker does not participate in binding to the presenter protein and/or the target protein.

Thus, a linker, when included in a compound and/or conjugate as described herein, achieves linking of two (or more) moieties by covalent means, involving bond formation with one or more functional groups located on either moiety. Examples of chemically reactive functional groups which may be employed for this purpose include, without limitation, amino, hydroxyl, sulfhydryl, carboxyl, carbonyl, carbohydrate groups, vicinal diols, thioethers, 2-aminoalcohols, 2-aminothiols, guanidinyl, imidazolyl, and phenolic groups.

In some embodiments, such covalent linking of two (or more) moieties may be effected using a linker that contains reactive moieties capable of reaction with such functional groups present in either moiety. For example, an amine group of a moiety may react with a carboxyl group of the linker, or an activated derivative thereof, resulting in the formation of an amide linking the two.

Examples of moieties capable of reaction with sulfhydryl groups include α-haloacetyl compounds of the type $XCH_2CO—$ (where X=Br, Cl, or I), which show particular reactivity for sulfhydryl groups, but which can also be used to modify imidazolyl, thioether, phenol, and amino groups as described by Gurd, *Methods Enzymol.* 11:532 (1967). N-Maleimide derivatives are also considered selective towards sulfhydryl groups, but may additionally be useful in coupling to amino groups under certain conditions. Reagents such as 2-iminothiolane (Traut et al., *Biochemistry* 12:3266 (1973)), which introduce a thiol group through conversion of an amino group, may be considered as sulfhydryl reagents if linking occurs through the formation of disulfide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type $XCH_2CO-$ (where X=Br, Cl, or I), for example, as described by Wong *Biochemistry* 24:5337 (1979);

(ii) N-maleimide derivatives, which may react with amino groups either through a Michael type reaction or through acylation by addition to the ring carbonyl group, for example, as described by Smyth et al., *J. Am. Chem. Soc.* 82:4600 (1960) and *Biochem. J.* 91:589 (1964);

(iii) aryl halides such as reactive nitrohaloaromatic compounds;

(iv) alkyl halides, as described, for example, by McKenzie et al., *J. Protein Chem.* 7:581 (1988);

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sufhydryl, and hydroxyl groups;

(viii) aziridines based on s-triazine compounds detailed above, e.g., as described by Ross, *J. Adv. Cancer Res.* 2:1 (1954), which react with nucleophiles such as amino groups by ring opening;

(ix) squaric acid diethyl esters as described by Tietze, *Chem. Ber.* 124:1215 (1991); and (x) α-haloalkyl ethers, which are more reactive alkylating agents than normal alkyl halides because of the activation caused by the ether oxygen atom, as described by Benneche et al., *Eur. J. Med. Chem.* 28:463 (1993).

Representative amino-reactive acylating agents include:

(i) isocyanates and isothiocyanates, particularly aromatic derivatives, which form stable urea and thiourea derivatives respectively;

(ii) sulfonyl chlorides, which have been described by Herzig et al., *Biopolymers* 2:349 (1964);

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation, for example, as described by M. Bodansky, *Principles of Peptide Synthesis*, Springer-Verlag, 1984;

(vii) acylazides, e.g., wherein the azide group is generated from a preformed hydrazide derivative using sodium nitrite, as described by Wetz et al., *Anal. Biochem.* 58:347 (1974);

(viii) imidoesters, which form stable amidines on reaction with amino groups, for example, as described by Hunter and Ludwig, *J. Am. Chem. Soc.* 84:3491 (1962); and (ix) haloheteroaryl groups such as halopyridine or halopyrimidine.

Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96 (1990).

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169 (1947). Carboxyl modifying reagents such as carbodiimides, which react through O-acylurea formation followed by amide bond formation, may also be employed.

It will be appreciated that functional groups in either moiety may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of one moiety with a reactive chemical group of the other without introducing additional linking material may, if desired, be used in accordance with the invention.

More commonly, however, the linker includes two or more reactive moieties, as described above, connected by a spacer element. The presence of such a spacer permits bifunctional linkers to react with specific functional groups within either moiety, resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between the two moieties.

Spacer elements in the linker typically consist of linear or branched chains and may include a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_2$-$C_{100}$ polyethylene glycol, or $C_{1-10}$ heteroalkyl.

In some instances, the linker is described by Formula V.

Examples of homobifunctional linkers useful in the preparation of conjugates of the invention include, without limitation, diamines and diols selected from ethylenediamine, propylenediamine and hexamethylenediamine, ethylene glycol, diethylene glycol, propylene glycol, 1,4-butanediol, 1,6-hexanediol, cyclohexanediol, and polycaprolactone diol.

In some embodiments, the linker is a bond or a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxyl, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and wherein any two atoms in the chain may be taken together with the substituents bound thereto to form a ring, wherein the ring may be further substituted and/or fused to one or more optionally substituted carbocyclic, heterocyclic, aryl, or heteroaryl rings.

In some embodiments, a linker has the structure of Formula XIX:

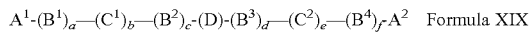  Formula XIX where $A^1$ is a bond between the linker and presenter protein binding moiety; $A^2$ is a bond between the mammalian target interacting moiety and the linker; $B^1$, $B^2$, $B^3$, and $B^4$ each, independently, is selected from optionally substituted $C_1$-$C_2$ alkyl, optionally substituted $C_1$-$C_3$ heteroalkyl, O, S, and $NR^N$; $R^N$ is hydrogen, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; $C^1$ and $C^2$ are each, independently, selected from carbonyl, thiocarbonyl, sulphonyl, or phosphoryl; a, b, c, d, e, and f are each, independently, 0 or 1; and D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_a$—$(C^1)_b$—$(B^2)_c$— to —$(B^3)_d$—$(C^2)_e$—$(B^4)_f$-$A^2$.

Proteins

Presenter Proteins

Presenter proteins can bind a small molecule to form a complex, which can bind to and modulate the activity of a target protein (e.g., a eukaryotic target protein such as a mammalian target protein or a fungal target protein or a prokaryotic target protein such as a bacterial target protein). In some embodiments, the presenter protein is a mammalian presenter protein (e.g., a human presenter protein). In some embodiments, the presenter protein is a fungal presenter protein. In certain embodiments, the presenter protein is a bacterial presenter protein. In some embodiments, the presenter protein is a plant presenter protein. In some embodiments, the presenter protein is a relatively abundant protein (e.g., the presenter protein is sufficiently abundant that participation in a tripartite complex does not materially negatively impact the biological role of the presenter protein in a cell and/or viability or other attributes of the cell). In some embodiments, the presenter protein is more abundant than the target protein. In certain embodiments, the presenter protein is a protein that has chaperone activity within a cell. In some embodiments, the presenter protein has multiple natural interaction partners within a cell. In certain embodiments, the presenter protein is one which is known to bind a small molecule to form a binary complex that is known to or suspected of binding to and modulating the biological activity of a target protein. Immunophilins are a class of presenter proteins which are known to have these functions and include FKBPs and cyclophilins. In some embodiments, a reference presenter protein exhibits peptidyl prolyl isomerase activity; in some embodiments, a presenter protein shows comparable activity to the reference presenter protein. In certain embodiments, the presenter protein is a member of the FKBP family (e.g., FKBP12, FKBP12.6, FKBP13, FKBP19, FKBP22, FKBP23, FKBP25, FKBP36, FKBP38, FKBP51, FKBP52, FKBP60, FKBP65, and FKBP133), a member of the cyclophilin family (e.g., PP1A, CYPB, CYPC, CYP40, CYPE, CYPD, NKTR, SRCyp, CYPH, CWC27, CYPL1, CYP60, CYPJ, PPIL4, PPIL6, RANBP2, PPWD1, PPIAL4A, PPIAL4B, PPIAL4C, PPIAL4D, or PPIAL4G), or PIN1. The "FKBP family" is a family of proteins that have prolyl isomerase activity and function as protein folding chaperones for proteins containing proline residues. Genes that encode proteins in this family include AIP, AIPL1, FKBP1A, FKBP1B, FKBP2, FKBP3, FKBP4, FKBP5, FKBP6, FKBP7, FKBP8, FKBP9, FKBP9L, FKBP10, FKBP11, FKBP14, FKBP15, and LOC541473.

The "cyclophilin family" is a family of proteins that bind to cyclosporine. Genes that encode proteins in this family include PPIA, PPIB, PPIC, PPID, PPIE, PPIF, PPIG, PPIH, SDCCAG-10, PPIL1, PPIL2, PPIL3, PPIL4, P270, PPWD1, and COAS-2. Exemplary cyclophilins include PP1A, CYPB, CYPC, CYP40, CYPE, CYPD, NKTR, SRCyp, CYPH, CWC27, CYPL1, CYP60, CYPJ, PPIL4, PPIL6, RANBP2, PPWD1, PPIAL4A, PPIAL4B, PPIAL4C, PPIAL4D, and PPIAL4G.

In some embodiments, a presenter protein is a chaperone protein such as GRP78/BiP, GRP94, GRP170, calnexin, calreticulin, HSP47, ERp29, Protein disulfide isomerase (PDI), and ERp57.

In some embodiments, a presenter protein is an allelic variant or splice variant of a FKBP or cyclophilin disclosed herein.

In some embodiments, a presenter protein is a polypeptide whose amino acid sequence i) shows significant identity with that of a reference presenter protein; ii) includes a portion that shows significant identity with a corresponding portion of a reference presenter protein; and/or iii) includes at least one characteristic sequence found in presenter protein. In many embodiments, identity is considered "significant" for the purposes of defining an presenter protein if it is above 80%, 81%, 82%, 83%, 84%, 85%, 86%, 87%, 89%, 90%, 91%, 92%, 93%, 94%, 95%, 96%, 97%, 98%, 99%, or higher. In some embodiments, the portion showing significant identity has a length of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 300, 350, 450, 500, 550, 600 amino acids or more.

Representative presenter proteins are encoded by the genes or homologs thereof listed in Table 1; in some embodiments, a reference presenter protein is encoded by a gene set forth in Table 1. Also, those of ordinary skill in the art, referring to Table 1, can readily identify sequences that are characteristic of presenter proteins generally, and/or of particular subsets of presenter proteins.

TABLE 1

Genes that Encode Selected Presenter Proteins

| Gene Name | Uniprot Accession Number |
|---|---|
| AIP | O00170 |
| AIPL1 | Q9NZN9 |
| FKBP1A | P62942 |
| FKBP1B | P68106 |
| FKBP2 | P26885 |
| FKBP3 | Q00688 |
| FKBP4 | Q02790 |
| FKBP5 | Q13451 |
| FKBP6 | O75344 |
| FKBP7 | Q9Y680 |
| FKBP8 | Q14318 |
| FKBP9 | O95302 |
| FKBP9L | Q75LS8 |
| FKBP10 | Q96AY3 |
| FKBP11 | Q9NYL4 |
| FKBP14 | Q9NWM8 |

TABLE 1-continued

Genes that Encode Selected Presenter Proteins

| Gene Name | Uniprot Accession Number |
|---|---|
| FKBP15 | Q5T1M5 |
| LOC541473 | — |
| PPIA | Q567Q0 |
| PPIB | P23284 |
| PPIC | P45877 |
| PPID | Q08752 |
| PPIE | Q9UNP9 |
| PPIG | Q13427 |
| PPIH | O43447 |
| PPIL1 | Q9Y3C6 |
| PPIL2 | Q13356 |
| PPIL3 | Q9H2H8 |
| PPIL4 | Q8WUA2 |
| PPIL5 | Q32Q17 |
| PPIL6 | Q8IXY8 |
| PPWD1 | Q96BP3 |

Target Proteins

A target protein (e.g., a eukaryotic target protein such as a mammalian target protein or a fungal target protein or a prokaryotic target protein such as a bacterial target protein) is a protein which mediates a disease condition or a symptom of a disease condition. As such, a desirable therapeutic effect can be achieved by modulating (inhibiting or increasing) its activity. Target proteins useful in the complexes and methods of the invention include those which do not naturally associate with a presenter protein, e.g., those which have an affinity for a presenter protein in the absence of a binary complex with a compound of the invention of greater than 1 µM, preferably greater than 5 µM, and more preferably greater than 10 µM. Alternatively, target proteins which do not naturally associate with a presenter protein are those which have an affinity for a compound of the invention in the absence of a binary complex greater than 1 µM, preferably greater than 5 µM, and more preferably greater than 10 µM. In another alternative, target proteins which do not naturally associate with a presenter protein are those which have an affinity for a binary complex of cyclosporine, rapamycin, or FK506 and a presenter protein (e.g., FKBP) of greater than 1 µM, preferably greater than 5 µM, and more preferably greater than 10 µM. In yet another alternative, target proteins that do not naturally associate with a presenter protein are those which are other than calcineurin or mTOR. The selection of suitable target proteins for the complexes and methods of the invention may depend on the presenter protein. For example, target proteins that have low affinity for a cyclophilin may have high affinity for an FKBP and would not be used together with the latter.

Target proteins can be naturally occurring, e.g., wild type. Alternatively, a target protein can vary from the wild type protein but still retain biological function, e.g., as an allelic variant, a splice mutant or a biologically active fragment.

In some embodiments, a target protein is a transmembrane protein. In some embodiments, a target protein has a coiled coil structure. In certain embodiments, a target protein is one protein of a dimeric complex.

In some embodiments, a target protein of the invention includes one or more surface sites (e.g., a flat surface site) characterized in that, in the absence of forming a presenter protein/compound complex, small molecules typically demonstrate low or undetectable binding to the site(s). In some embodiments, a target protein includes one or more surface sites (e.g., a flat surface site) to which, in the absence of forming a presenter protein/compound complex, a particular small molecule (e.g., the compound) shows low or undetectable binding (e.g., binding at least 2, 3, 4, 5, 6, 7, 8, 9, 10, 20, 30, 40, 50, 100 fold or more lower than that observed with a presenter protein/compound complex involving the same compound). In some embodiments, a target protein has a surface characterized by one or more sites (and, in some embodiments, an entire surface) that lack(s) any traditional binding pocket, for example, a cavity or pocket on the protein structure with physiochemical and/or geometric properties comparable to proteins whose activity has been modulated by one or more small molecules. In certain embodiments, a target protein has a traditional binding pocket and a site for a protein-protein interaction. In some embodiments, a target protein is an undruggable target, for example, a target protein is not a member of a protein family which is known to be targeted by drugs and/or does not possess a binding site that is expected (e.g., according to art-accepted understanding, as discussed herein) to be suitable for binding to a small molecule. In some embodiments, the protein includes at least one reactive cysteine.

In some embodiments, the target protein is a GTPase such as DIRAS1, DIRAS2, DIRAS3, ERAS, GEM, HRAS, KRAS, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, RRAS2, RHOA, RHOB, RHOBTB1, RHOBTB2, RHOBTB3, RHOC, RHOD, RHOF, RHOG, RHOH, RHOJ, RHOQ, RHOU, RHOV, RND1, RND2, RND3, RAC1, RAC2, RAC3, CDC42, RAB1A, RAB1B, RAB2, RAB3A, RAB3B, RAB3C, RAB3D, RAB4A, RAB4B, RAB5A, RAB5B, RAB5C, RAB6A, RAB6B, RAB6C, RAB7A, RAB7B, RAB7L1, RAB8A, RAB8B, RAB9, RAB9B, RABL2A, RABL2B, RABL4, RAB10, RAB11A, RAB11B, RAB12, RAB13, RAB14, RAB15, RAB17, RAB18, RAB19, RAB20, RAB21, RAB22A, RAB23, RAB24, RAB25, RAB26, RAB27A, RAB27B, RAB28, RAB2B, RAB30, RAB31, RAB32, RAB33A, RAB33B, RAB34, RAB35, RAB36, RAB37, RAB38, RAB39, RAB39B, RAB40A, RAB40AL, RAB40B, RAB40C, RAB41, RAB42, RAB43, RAP1A, RAP1B, RAP2A, RAP2B, RAP2C, ARF1, ARF3, ARF4, ARF5, ARF6, ARL1, ARL2, ARL3, ARL4, ARL5, ARL5C, ARL6, ARL7, ARL8, ARL9, ARL10A, ARL10B, ARL10C, ARL11, ARL13A, ARL13B, ARL14, ARL15, ARL16, ARL17, TRIM23, ARL4D, ARFRP1, ARL13B, RAN, RHEB, RHEBL1, RRAD, GEM, REM, REM2, RIT1, RIT2, RHOT1, or RHOT2. In some embodiments, the target protein is a GTPase activating protein such as NF1, IQGAP1, PLEXIN-B1, RASAL1, RASAL2, ARHGAP5, ARHGAP8, ARHGAP12, ARHGAP22, ARHGAP25, BCR, DLC1, DLC2, DLC3, GRAF, RALBP1, RAP1GAP, SIPA1, TSC2, AGAP2, ASAP1, or ASAP3. In some embodiments, the target protein is a Guanine nucleotide-exchange factor such as CNRASGEF, RASGEF1A, RASGRF2, RASGRP1, RASGRP4, SOS1, RALGDS, RGL1, RGL2, RGR, ARHGEF10, ASEF/ARHGEF4, ASEF2, DBS, ECT2, GEF-H1, LARG, NET1, OBSCURIN, P-REX1, P-REX2, PDZ-RHOGEF, TEM4, TIAM1, TRIO, VAV1, VAV2, VAV3, DOCK1, DOCK2, DOCK3, DOCK4, DOCK8, DOCK10, C3G, BIG2/ARFGEF2, EFA6, FBX8, or GEP100. In certain embodiments, the target protein is a protein with a protein-protein interaction domain such as ARM; BAR; BEACH; BH; BIR; BRCT; BROMO; BTB; C1; C2; CARD; CC; CALM; CH; CHROMO; CUE; DEATH; DED; DEP; DH; EF-hand; EH; ENTH; EVH1; F-box; FERM; FF; FH2;

FHA; FYVE; GAT; GEL; GLUE; GRAM; GRIP; GYF; HEAT; HECT; IQ; LRR; MBT; MH1; MH2; MIU; NZF; PAS; PB1; PDZ; PH; POLO-Box; PTB; PUF; PWWP; PX; RGS; RING; SAM; SC; SH3; SOCS; SPRY; START; SWIRM; TIR; TPR; TRAF; SNARE; TUBBY; TUDOR; UBA; UEV; UIM; VHL; VHS; WD40; WW; SH2; SH3; TRAF; Bromodomain; or TPR. In some embodiments, the target protein is a heat shock protein such as Hsp20, Hsp27, Hsp70, Hsp84, alpha B crystalline, TRAP-1, hsf1, or Hsp90. In certain embodiments, the target protein is an ion channel such as Cav2.2, Cav3.2, IKACh, Kv1.5, TRPA1, NAv1.7, Nav1.8, Nav1.9, P2X3, or P2X4. In some embodiments, the target protein is a coiled-coil protein such as geminin, SPAG4, VAV1, MAD1, ROCK1, RNF31, NEDP1, HCCM, EEA1, Vimentin, ATF4, Nemo, SNAP25, Syntaxin 1a, FYCO1, or CEP250. In certain embodiments, the target protein is a kinase such as Cyclin D1, ABL, ALK, AXL, BTK, EGFR, FMS, FAK, FGFR1, 2, 3, 4, FLT3, HER2/ErbB2, HER3/ErbB3, HER4/ErbB4, IGF1R, INSR, JAK1, JAK2, JAK3, KIT, MET, PDGFRA, PDGFRB, RET RON, ROR1, ROR2, ROS, SRC, SYK, TIE1, TIE2, TRKA, TRKB, KDR, AKT1, AKT2, AKT3, PDK1, PKC, RHO, ROCK1, RSK1, RKS2, RKS3, ATM, ATR, CDK1, CDK2, CDK3, CDK4, CDK5, CDK6, CDK7, CDK8, CDK9, CDK10, ERK1, ERK2, ERK3, ERK4, GSK3A, GSK3B, JNK1, JNK2, JNK3, AurA, AurB, PLK1, PLK2, PLK3, PLK4, IKK, KIN1, cRaf, PKN3, c-Src, Fak, PyK2, or AMPK. In some embodiments, the target protein is a phosphatase such as WIP1, SHP2, SHP1, PRL-3, PTP1B, or STEP. In certain embodiments the target protein is a ubiquitin or ubiquitin-like protein (such as NEDD8, ATG8 proteins, SUMO proteins, ISG15), activating enzyme (E1's such as UBA1, UBA2, UBA3, UBA5, UBA6, UBA7, ATG7, NAE1, SAE1), conjugation enzyme (E2's such as UBE proteins, ATG3, BIRC6), ligation enzyme (E3's such as BMI-1, MDM2, NEDD4-1, Beta-TRCP, SKP2, E6AP, CBL-B, or APC/C), and ubiquitin or ubiquitin-like protein protease. In some embodiments, the target protein is a chromatin modifier/remodeler such as a chromatin modifier/remodeler encoded by the gene BRG1, BRM, ATRX, PRDM3, ASH1L, CBP, KAT6A, KAT6B, MLL, NSD1, SETD2, EP300, KAT2A, or CREBBP. In some embodiments, the target protein is a transcription factor such as a transcription factor encoded by the gene EHF, ELF1, ELF3, ELF4, ELF5, ELK1, ELK3, ELK4, ERF, ERG, ETS1, ETV1, ETV2, ETV3, ETV4, ETV5, ETV6, FEV, FLII, GAVPA, SPDEF, SPI1, SPIC, SPIB, E2F1, E2F2, E2F3, E2F4, E2F7, E2F8, ARNTL, BHLHA15, BHLHB2, BHL-BHB3, BHLHE22, BHLHE23, BHLHE41, CLOCK, FIGLA, HAS5, HES7, HEY1, HEY2, ID4, MAX, MESP1, MLX, MLXIPL, MNT, MSC, MYF6, NEUROD2, NEUROG2, NHLH1, OLIG1, OLIG2, OLIG3, SREBF2, TCF3, TCF4, TFAP4, TFE3, TFEB, TFEC, USF1, ARF4, ATF7, BATF3, CEBPB, CEBPD, CEBPG, CREB3, CREB3L1, DBP, HLF, JDP2, MAFF, MAFG, MAFK, NRL, NFE2, NFIL3, TEF, XBP1, PROXI, TEAD1, TEAD3, TEAD4, ONECUT3, ALX3, ALX4, ARX, BARHL2, BARX, BSX, CART1, CDX1, CDX2, DLX1, DLX2, DLX3, DLX4, DLX5, DLX6, DMBX1, DPRX, DRGX, DUXA, EMX1, EMX2, EN1, EN2, ESX1, EVX1, EVX2, GBX1, GBX2, GSC, GSC2, GSX1, GSX2, HESX1, HMX1, HMX2, HMX3, HNF1A, HNF1B, HOMEZ, HOXA1, HOXA10, HOXA13, HOXA2, HOXAB13, HOXB2, HOXB3, HOXB5, HOXC10, HOXC11, HOXC12, HOXC13, HOXD11, HOXD12, HOXD13, HOXD8, IRX2, IRX5, ISL2, ISX, LBX2, LHX2, LHX6, LHX9, LMX1A, LMX1B, MEIS1, MEIS2, MEIS3, MEOX1, MEOX2, MIXL1, MNX1, MSX1, MSX2, NKX2-3, NKX2-8, NKX3-1, NKX3-2, NKX6-1, NKX6-2, NOTO, ONECUT1, ONECUT2, OTX1, OTX2, PDX1, PHOX2A, PHOX2B, PITX1, PITX3, PKNOX1, PROP1, PRRX1, PRRX2, RAX, RAXL1, RHOXF1, SHOX, SHOX2, TGIF1, TGIF2, TGIF2LX, UNCX, VAX1, VAX2, VENTX, VSX1, VSX2, CUX1, CUX2, POU1F1, POU2F1, POU2F2, POU2F3, POU3F1, POU3F2, POU3F3, POU3F4, POU4F1, POU4F2, POU4F3, POU5F1P1, POU6F2, RFX2, RFX3, RFX4, RFX5, TFAP2A, TFAP2B, TFAP2C, GRHL1, TFCP2, NFIA, NFIB, NFIX, GCM1, GCM2, HSF1, HSF2, HSF4, HSFY2, EBF1, IRF3, IRF4, IRF5, IRF7, IRF8, IRF9, MEF2A, MEF2B, MEF2D, SRF, NRF1, CPEB1, GMEB2, MYBL1, MYBL2, SMAD3, CENPB, PAX1, PAX2, PAX9, PAX3, PAX4, PAX5, PAX6, PAX7, BCL6B, EGR1, EGR2, EGR3, EGR4, GLIS1, GLIS2, GLI2, GLIS3, HIC2, HINFP1, KLF13, KLF14, KLF16, MTF1, PRDM1, PRDM4, SCRT1, SCRT2, SNAI2, SP1, SP3, SP4, SP8, YY1, YY2, ZBED1, ZBTB7A, ZBTB7B, ZBTB7C, ZIC1, ZIC3, ZIC4, ZNF143, ZNF232, ZNF238, ZNF282, ZNF306, ZNF410, ZNF435, ZBTB49, ZNF524, ZNF713, ZNF740, ZNF75A, ZNF784, ZSCAN4, CTCF, LEF1, SOX10, SOX14, SOX5, SOX18, SOX2, SOX21, SOX4, SOX7, SOX8, SOX9, SRY, TCF7L1, FOXO3, FOXB1, FOXC1, FOXC2, FOXD2, FOXD3, FOXG1, FOXI1, FOXJ2, FOXJ3, FOXK1, FOXL1, FOXO1, FOXO4, FOXO6, FOXP3, EOMES, MGA, NFAT5, NFATC1, NFKB1, NFKB2, TP63, RUNX2, RUNX3, T, TBR1, TBX1, TBX15, TBX19, TBX2, TBX20, TBX21, TBX4, TBX5, AR, ESR1, ESRRA, ESRRB, ESRRG, HNF4A, NR2C2, NR2E1, NR2F1, NR2F6, NR3C1, NR3C2, NR4A2, RARA, RARB, RARG, RORA, RXRA, RXRB, RXRG, THRA, THRB, VDR, GATA3, GATA4, or GATA5; or C-myc, Max, Stat3, Stat4, Stat6, androgen receptor, C-Jun, C-Fox, N-Myc, L-Myc, MITF, Hif-1alpha, Hif-2alpha, Bcl6, E2F1, NF-kappaB, Stat5, or ER(coact). In certain embodiments, the target protein is TrkA, P2Y14, mPEGS, ASK1, ALK, Bcl-2, BCL-XL, mSIN1, RORγt, IL17RA, elF4E, TLR7R, PCSK9, IgE R, CD40, CD40L, Shn-3, TNFR1, TNFR2, IL31RA, OSMR, IL12beta1,2, Tau, FASN, KCTD 6, KCTD 9, Raptor, Rictor, RALGAPA, RALGAPB, Annexin family members, BCOR, NCOR, beta catenin, AAC 11, PLD1, PLD2, Frizzled7, RaLP, MLL-1, Myb, Ezh2, RhoGD12, EGFR, CTLA4R, GCGC (coact), Adiponectin R2, GPR 81, IMPDH2, IL-4R, IL-13R, IL-1R, IL2-R, IL-6R, IL-22R, TNF-R, TLR4, MyD88, Keap1, or Nrlp3.

Protein Variants

A protein or polypeptide variant, as described herein, generally has an amino acid sequence that shows significant (e.g., 80% or more, i.e., 80%, 81%, 82%, 83%, 84%, 85%, 86%, 87%, 88%, 89%, 90%, 91%, 92%, 93%, 94%, 95%, 96%, 97%, 98%, 99%, or more) identity with that of a reference polypeptide (e.g., a presenter protein or target protein as described herein such as for example a mammalian presenter protein or target protein) but includes a limited number of particular amino acid changes (e.g., insertions, deletions, or substitutions, either conservative or non-conservative and/or including one or more amino acid variants or analogs (e.g., D-amino acids, desamino acids) relative to the reference polypeptide. In certain embodiments, a variant shares a relevant biological activity (e.g., binding to a particular compound or moiety thereof) with the reference polypeptide; in some such embodiments, the variant displays such activity at a level that is not less than about 50% of that of the reference polypeptide and/or is not less than about 0.5 fold below that of the reference polypeptide.

In some embodiments, a variant polypeptide has an amino acid sequence that differs from that of a reference polypeptide at least (or only) in that the variant has a larger number of cysteine residues and/or has one or more cysteine residues at a position corresponding to a non-cysteine residue in the reference polypeptide. For example, in some embodiments, addition of one or more cysteine residues to the amino or carboxy terminus of any of a polypeptide (e.g., of a presenter protein and/or of a target protein) as described herein can facilitate conjugation of such polypeptide by, e.g., disulfide bonding. In some embodiments, amino acid substitutions can be conservative (i.e., wherein a residue is replaced by another of the same general type or group) or non-conservative (i.e., wherein a residue is replaced by an amino acid of another type). In some embodiments, a naturally occurring amino acid can be substituted for a non-naturally occurring amino acid (i.e., non-naturally occurring conservative amino acid substitution or a non-naturally occurring non-conservative amino acid substitution), or vice versa.

Polypeptides made synthetically can include substitutions of amino acids not naturally encoded by DNA (e.g., non-naturally occurring or unnatural amino acid). Examples of non-naturally occurring amino acids include D-amino acids, an amino acid having an azide-containing side chain, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the structure (e.g., a local structure or global structure) of the original protein. Examples of substitutions identified as "conservative substitutions" are shown in Table 2. If such substitutions result in a change not desired, then other type of substitutions, denominated "exemplary substitutions" in Table 2, or as further described herein in reference to amino acid classes, are introduced and the products screened.

Substantial modifications in function or immunological identity are accomplished by selecting substitutions that differ significantly in their effect on maintaining (a) the structure of the protein backbone in the area of the substitution, for example, as a sheet or helical conformation. (b) the charge or hydrophobicity of the molecule at the target site, or (c) the bulk of the side chain. Naturally occurring residues are divided into groups based on common side chain properties:
(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe),
(2) neutral hydrophilic: Cysteine (Cys), Serine (Ser), Threonine (Thr)
(3) acidic/negatively charged: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro);
(6) aromatic: Tryptophan (Trp), Tyrosine (Tyr), Phenylalanine (Phe), Histidine (His),
(7) polar: Ser, Thr, Asn, Gln
(8) basic positively charged: Arg, Lys, His, and;
(9) charged: Asp, Glu, Arg, Lys, His Other amino acid substitutions are listed in Table 2.

TABLE 2

Amino acid substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Protein Variants with Altered Reactive Amino Acid Profiles

In some embodiments, a protein or polypeptide variant may include the addition of one or more reactive amino acid residues (e.g., cysteines) to a protein (e.g., at the amino or carboxy terminus of any of the proteins described herein) can facilitate conjugation of these proteins by, e.g., disulfide bonding. In some embodiments, one or more reactive amino acids (e.g., cysteines) may be removed to decrease the number of possible conjugation sites on a protein. Amino acid substitutions can be conservative (i.e., wherein a residue is replaced by another of the same general type or group) or non-conservative (i.e., wherein a residue is replaced by an amino acid of another type). In addition, a naturally occurring amino acid can be substituted for a non-naturally occurring amino acid (i.e., non-naturally occurring conservative amino acid substitution or a non-naturally occurring non-conservative amino acid substitution).

As is known in the art, e.g., as described in Chin, J. W., Expanding and Reprogramming the Genetic Code of Cells and Animals, Annual Review of Biochemistry, Vol. 83: 379-408, unnatural amino acids may be incorporated into proteins made in vitro. For example, in one system, UAG amber (stop) codons have been used to incorporate pyrrolysine via an archeal tRNA synthetase and tRNA and these can also be used to incorporate azides and alkynes via feeding. Other side chains on unnatural amino acids that have been demonstrated in the art include cyclopropene, trans-cyclooctene, bicyclo[6.1.0]nonyne-lysine, coumarins, p-azidophenylalanine, N6-[(2-propynloxy)carbonyl]-L-Lysine, bicyclo[6.1.0]non-4-yn-9-ylmethanol (BCN), N-5-norbornene-2-yloxycarbonyl-l-lysine, N-tert-butyloxycarbonyl-l-lysine, N-2-azidoethyloxycarbonyl-l-lysine, N-L-thiaprolyl-L-lysine, N-D-cysteinyl-L-lysine, N-L-cysteinyl-L-lysine, N6-[(2-propynyloxy)carbonyl]-L-lysine, N6-[(2-azidoethoxy)carbonyl]-L-lysine, benzophenone, 4-(6-methyl-s-tetrazin-3-yl)aminophenylalanine, and cyclooctynes.

Complexes

In naturally occurring protein-protein interactions, binding events are typically driven largely by hydrophobic residues on flat surface sites of the interacting proteins, in contrast to many small molecule-protein interactions which are driven by interactions between the small molecule in a cavity or pocket on the protein. Commonly, hydrophobic residues on a protein's flat surface site form a hydrophobic hot spot wherein most of the binding interactions between or among interacting proteins are van der Waals interactions. In some situations, a small molecule may provide a "portable hotspot" (or portion thereof) in that it participates in or generates such as a hydrophobic interaction site on a protein (e.g., a presenter proteins) where such does not exist absent the small molecule; aspects of the present disclosure are particularly applicable to such situations. For example, in some embodiments, a compound (and/or a tagged form thereof) as described herein forms a complex with a protein (e.g., a presenter protein/compound complex) and participates in pseudo protein-protein interactions (e.g., forming a tripartite complex with a target protein).

Many mammalian proteins are able to bind to any of a plurality of different partners; in some cases, such alternative binding interactions contribute to biological activity of the proteins. Many of these proteins adapt the inherent variability of the hot spot protein regions to present the same residues in different structural contexts. More specifically, the protein-protein interactions can be mediated by a class of natural products produced by a select group of fungal and bacterial species. These molecules exhibit both a common structural organization and resultant functionality that provides the ability to modulate protein-protein interaction. These molecules contain a presenter protein binding moiety that is highly conserved and a target protein interacting moiety that exhibits a high degree of variability among the different natural products. The presenter protein binding moiety confers specificity for the presenter protein and allows the molecule to bind to the presenter protein to form a complex; the mammalian target protein binding moiety confers specificity for the target protein and allows the binary complex to bind to the target protein, typically modulating (e.g., positively or negatively modulating) its activity. In the present invention, a binary complex (e.g., between a compound and presenter protein or a compound and a target protein) is mimicked by conjugating a presenter protein binding moiety to a target protein or a target protein binding moiety to presenter protein. The resulting conjugates of the invention may then bind to a presenter protein or target protein forming a complex that mimics the tripartite complex. These complexes may be used, e.g., to determine the structure of the interface between the presenter protein and the target protein. Furthermore, by simplifying the formation of the complex, e.g., by conjugated a presenter protein binding moiety to a target protein, the compounds of the invention may be used, e.g., to identify target proteins capable of binding to presenter proteins.

Uses

Identification of Target Proteins

In some embodiments, the compounds, conjugates, complexes, compositions, and/or methods of the present invention may be useful to identify target proteins capable of forming complexes with presenter proteins (e.g., in the presence of a small molecule). The target proteins may be identified by formation of conjugates including a presenter protein binding moiety conjugated to a target moiety and determining if the conjugate forms a complex with a presenter protein.

Most target proteins known in the art to form ternary complexes with presenter proteins and small molecules were identified fortuitously during determination of the mechanism of action of the small molecule. The present methods allow for the rational identification of target proteins capable of forming complexes with presenter proteins in the presence of small molecules by covalently conjugating a presenter protein binding moiety to the target molecule, allowing formation of a complex prior to identification of a compound capable of binding both the presenter protein and target protein simultaneously.

Screening of small molecules for their ability to facilitate complex formation between the presenter protein and identified target protein could then be carried out to identify potential therapeutics capable of modulating the biological activity of the target protein.

In some embodiments, the compounds of the invention may be used to identify target proteins capable of forming complexes with presenter proteins. For example, target proteins may be identified by combining one or more target proteins with a labeled presenter protein (e.g., labeled with biotin) in the presence of a compound of the invention under conditions suitable to allow for formation of a presenter protein/target protein complex. The target proteins which do not form complexes with presenter proteins may then be removed (e.g., washed out) and the target proteins which form complexes may then be pulled down using the label on the presenter protein and analyzed. In some embodiments, the pulled down target proteins may be analyzed by mass spectrometry to determine their identity.

Compound Design

In some embodiments, the compounds, conjugates, complexes, compositions, and/or methods of the present invention may be useful for the design of compounds capable of modulating the biological activity of target proteins for use in the treatment of disease.

For example, formation of complexes of presenter proteins and conjugates of the invention can facilitate determination of the structure of the protein-protein interface between a presenter protein and a target protein by crystallization and crystal structure determination of the complex. Once the crystal structure of a complex of the invention is determined, methods known in the art for rational drug design may be used to develop small molecules capable of facilitating complex formation between the presenter protein and the target protein such as computational chemistry methods to build structures de novo and/or fragment based drug design using methods such as fragment soaking the crystals of complexes of the invention and determining the resulting structure.

The compounds designed as described above may then be screened to determine their ability to modulate the biological activity of the target protein and modified using medicinal chemistry techniques, as necessary, to produce therapeutically useful compounds.

Identification of Covalent Small Molecule Therapeutics

In some embodiments, the compounds, conjugates, complexes, compositions, and/or methods of the present invention may be useful for identifying compounds capable of modulating the biological activity of target proteins through covalent interaction.

For example, the compounds of the inventions may be screened for their ability to covalently bind to target proteins in the presence and absence of presenter proteins to identify compounds capable of selectively binding to target proteins only in the presence of a presenter protein. These compounds may then be tested for their ability to modulate biological activity of the target protein and modified using medicinal chemistry techniques, as necessary, to produce therapeutically useful compounds.

Determination of Biochemical and/or Biophysical Properties

In some embodiments, the compounds, conjugates, complexes, compositions, and/or methods of the invention may be useful for determining biochemical and/or biophysical properties of a protein or complex.

For example, the free energy of binding between a conjugate including a presenter protein binding moiety and a target protein and a presenter protein may be determined, e.g., by isothermal titration calorimetry. The $K_d$ of a conjugate including a presenter protein binding moiety and a target protein for a presenter protein may be determined, e.g., by surface plasmon resonance. The $K_i$, $K_{inact}$, and/or $K_i/K_{inact}$ for a compound and a presenter protein for a target protein may be determined, e.g., by mass spectrometry.

Treatment of Diseases or Disorders

Compounds, conjugates, and complexes described herein may be useful in the methods of treating diseases or disorders related to the target proteins described herein, and, while not bound by theory, are believed to exert their desirable effects through their ability to modulate (e.g., positively or negatively modulate) the activity of a target protein (e.g., a eukaryotic target protein such as a mammalian target protein or a fungal target protein or a prokaryotic target protein such as a bacterial target protein), through interaction with presenter proteins and the target protein.

Kits

In some embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, for instance if the subject suffers from Alzheimer's disease, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Pharmaceutical Compositions

For use as treatment of human and animal subjects, the compounds and conjugates of the invention can be formulated as pharmaceutical or veterinary compositions. Depending on the subject to be treated, the mode of administration, and the type of treatment desired—e.g., prevention, prophylaxis, or therapy—the compounds are formulated in ways consonant with these parameters. A summary of such techniques is found in *Remington: The Science and Practice of Pharmacy*, 21$^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compounds described herein may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, compounds described herein may be used alone, or in combination with one or more other active agents. An example of other pharmaceuticals to combine with the compounds described herein would include pharmaceuticals for the treatment of the same indication. Another example of a potential pharmaceutical to combine with compounds described herein would include pharmaceuticals for the treatment of different yet associated or related symptoms or indications. Depending on the mode of administration, compounds are formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

Compounds of the invention may be prepared and used as pharmaceutical compositions comprising an effective amount of a compound described herein and a pharmaceutically acceptable carrier or excipient, as is well known in the art. In some embodiments, a composition includes at least two different pharmaceutically acceptable excipients or carriers.

Formulations may be prepared in a manner suitable for systemic administration or topical or local administration.

Systemic formulations include those designed for injection (e.g., intramuscular, intravenous or subcutaneous injection) or may be prepared for transdermal, transmucosal, or oral administration. A formulation generally include diluents as well as, in some cases, adjuvants, buffers, preservatives and the like. Compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with nontoxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluents (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention depends on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the subject. Chronic, long-term administration may be indicated.

EXAMPLES

Example 1: Synthesis of Certain Cross-linking Reagents

Synthesis of (R)-3-(3,4-dimethoxyphenyl)-1-(3-(3-(pyridin-2-yldisulfanyl)propanamido)phenyl)propyl (S)-1-(3,3-dimethyl-2-oxopentanoyl)piperidine-2-carboxylate (C3-SLF)

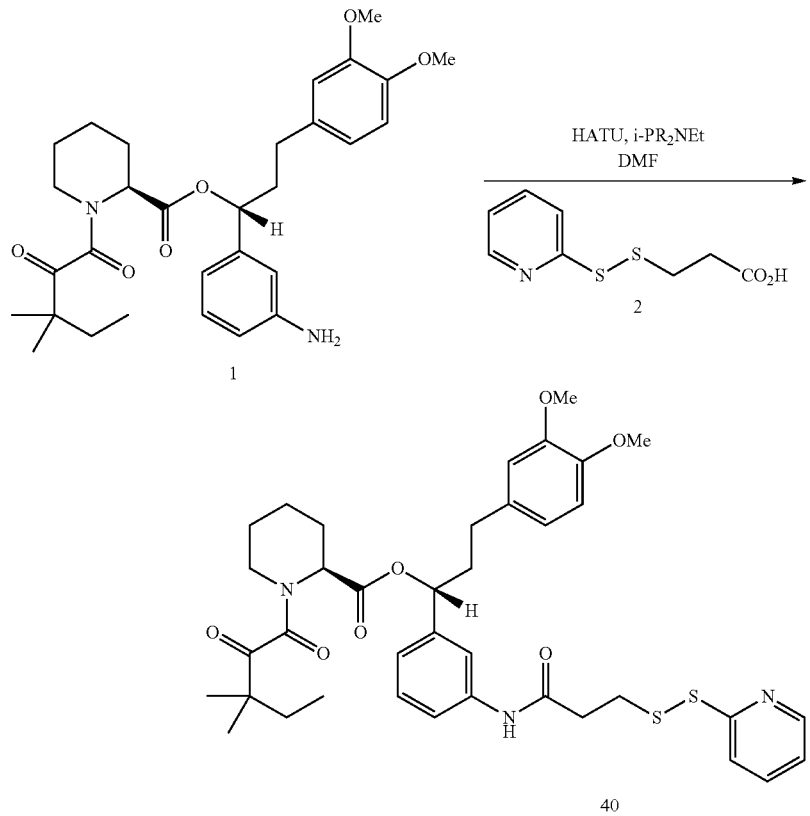

To a solution of Aniline 1 (90 mg, 1721 μmol, 1 eq), disulfide 2 (74 mg, 343 μmol, 2 eq) and diisopropylethylamine (1491 μL, 111 mg, 8581 μmol, 5 eq) in DNF (3 mL) was added HATU (130 mg, 343 μmol, 2 eq) and the reaction was stirred at room temperature for 24 h. The reaction mixture was diluted with water and extracted with ethyl acetate (3×). The organic extracts were washed with water, saturated sodium chloride, dried over magnesium sulfate and evaporated. The residue was purified on Silica gel gradient elution (20% ethyl acetate: 80% heptane→100% ethyl acetate) to provide the tittle compound C3-SLF (50 mg, 40%). MS (ESI) calc=722.3 (M+H), obs=722.3.

Synthesis of (R)-3-(3,4-dimethoxyphenyl)-1-(3-(4-(pyridin-2-yldisulfanyl)butanamido)phenyl)propyl (S)-1-(3,3-dimethyl-2-oxopentanoyl)piperidine-2-carboxylate (C4-SLF)

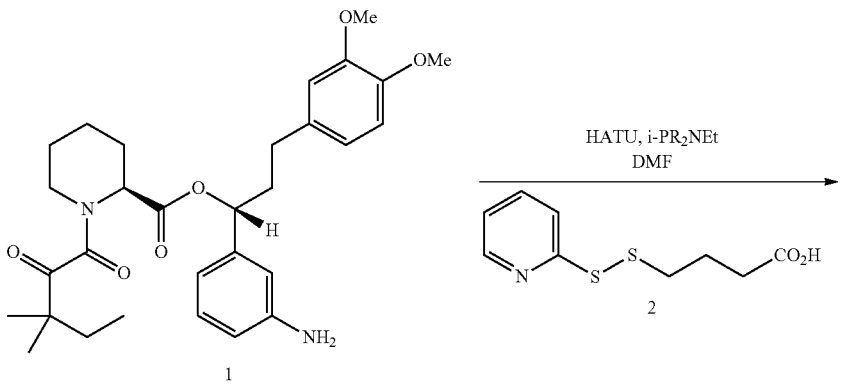

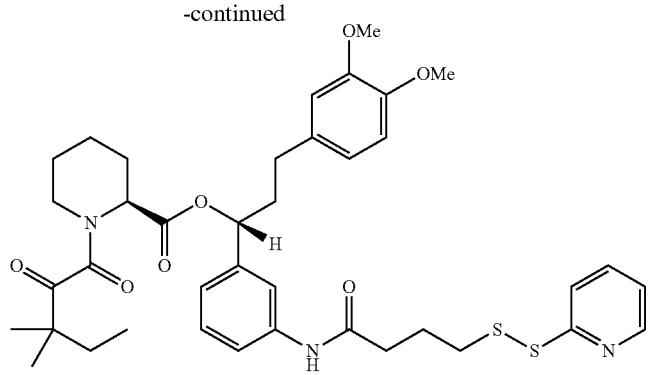

To a solution of Aniline 1 (90 mg, 172 μmol, 1 eq), disulfide 2 (79 mg, 343 μmol, 2 eq) and diisopropylethylamine (149 μL, 111 mg, 858 μmol, 5 eq) in DMF (3 mL) was added HATU (130 mg, 343 μmol, 2 eq) and the reaction mixture was stirred at room temperature for 24 h. The reaction mixture was diluted with water and extracted with ethyl acetate (3×). The organic extracts were washed with water, saturated sodium chloride, dried over magnesium sulfate and evaporated. The residue was purified on Silica gel gradient elution (20% ethyl acetate: 80% heptane→100% ethyl acetate) to provide the tittle compound C4-SLF (98 mg, 77%). MS (ESI) calc=736.3 (M+H), obs=736.3.

Synthesis of methyl (S)-1-((S)-3-(3-hydroxyphenyl)-2-((S)-3-methyl-2-(4-(pyridin-2-yldisulfanyl)butanamido)butanamido)propanoyl)hexahydropyridazine-3-carboxylate (SFAC4DS)

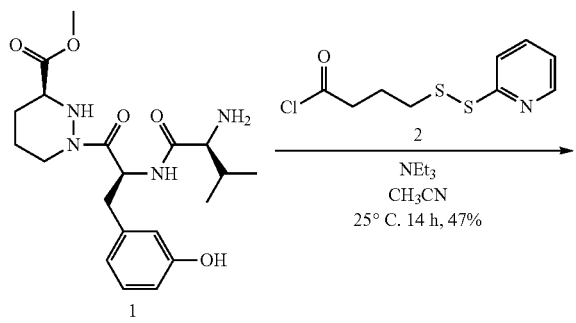

Amine 1 was prepared according to Paquette et al., JACS 2002(124), 4257-4270. To a solution of amine 1 (20 mg, 49.2 μmol) in 1 mL of acetonitrile was added triethylamine (16.51 μL, 118 μmol, 2.4 eq), followed by acid chloride 2 (13.8 mg, 59.2 μmol, 1.2 eq). The reaction mixture was stirred at room temperature for 14 h, then concentrated, and the residue was purified by preparative TLC (dichloromethane:MeOH:NH$_4$OH, 20:1:0.1) to afford 14.0 mg (47%) of the product as a colorless foam. R$_f$=0.59 (dichloromethane:MeOH:NH$_4$OH, 10:1:0.1). MS (ESI) calc=618.2 (M+H), obs=618.2.

Synthesis of methyl (S)-1-((S)-3-(3-hydroxyphenyl)-2-((S)-3-methyl-2-(3-(2-(pyridin-2-yldisulfanyl)ethoxy)propanamido)butanamido)propanoyl)hexahydropyridazine-3-carboxylate (SFAX6)

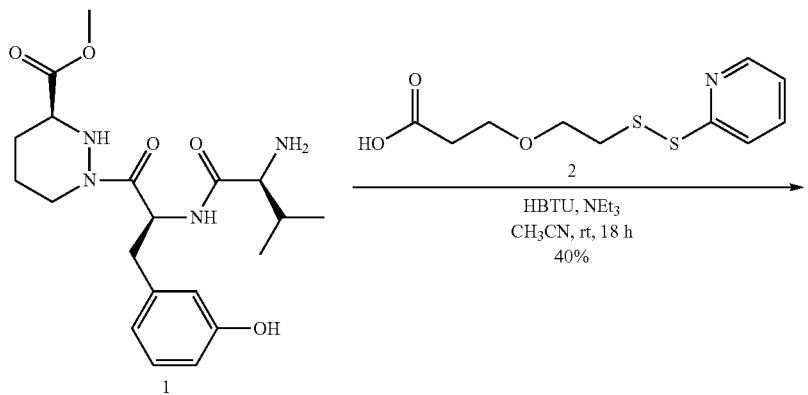

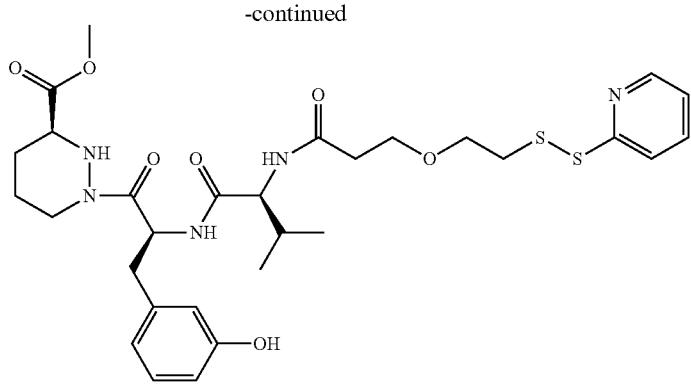

Carboxylic acid 2 (70 mg, 0.270 mmol) and HBTU (204 mg, 0.540 mmol, 2.00 eq) were mixed in 3 mL of acetonitrile, and the resulting suspension was stirred at room temperature for 15 min. Following this period, amine 1 (110 mg, 0.270 mmol, 1.00 eq) was added followed by triethylamine (113 μL, 0.810 mmol, 3.00 eq) and the mixture was stirred at room temperature for 18 h. The mixture was then treated with 20 mL of saturated sodium bicarbonate and extracted with 2×30 mL portions of ethyl acetate. The pooled organic extracts were washed with 2×20 mL portions of brine, dried over saturated sodium sulfate, filtered and concentrated under vacuum. The residue was purified using silica gel chromatography, eluting with dichloromethane: MeOH, 100:1 to 50:1, affording 70 mg (40%) of the product as a colorless oil. $R_f$=0.31 (dichloromethane:MeOH, 20:1). MS (ESI) calc=648.2 (M+H), obs=648.2.

Synthesis of N-(4-((2S,11R,14S,17S,20S,23S,26S)-26-ethyl-23-((1R,2R, E)-1-hydroxy-2-methylhex-4-en-1-yl)-14,17-diisobutyl-20-isopropyl-4,11,13,16,19,22,28,31-octamethyl-3,6,9,12,15,18,21,24,27,30,33-undecaoxo-1,4,7,10,13,16,19,22,25,28,31-undecaazacyclotritriacontan-2-yl)butyl)-4-(pyridin-2-yldisulfanyl)butanamide (CsA3)

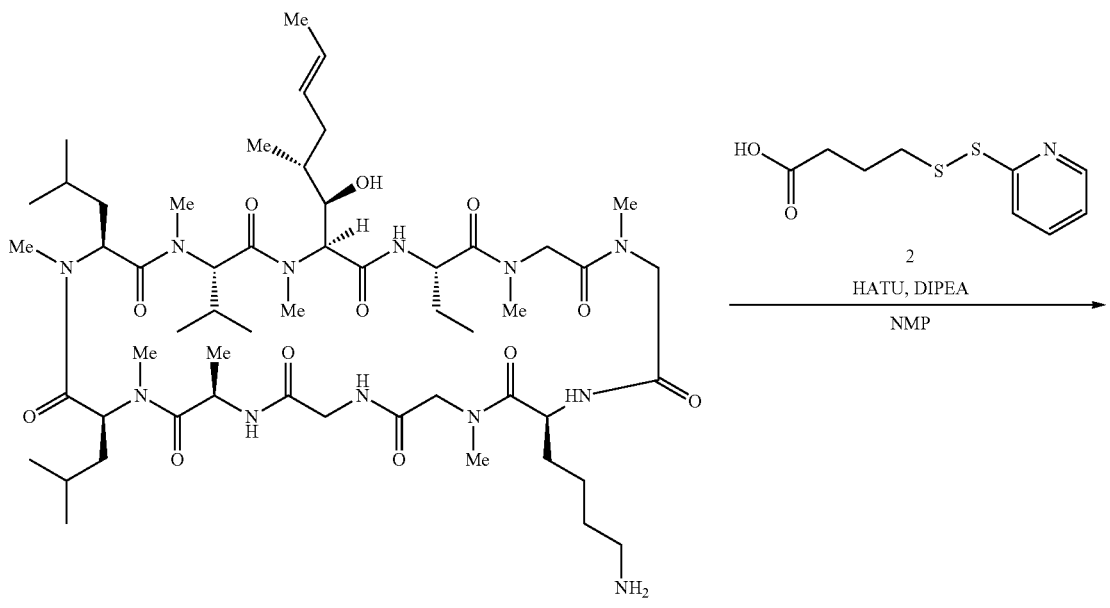

-continued

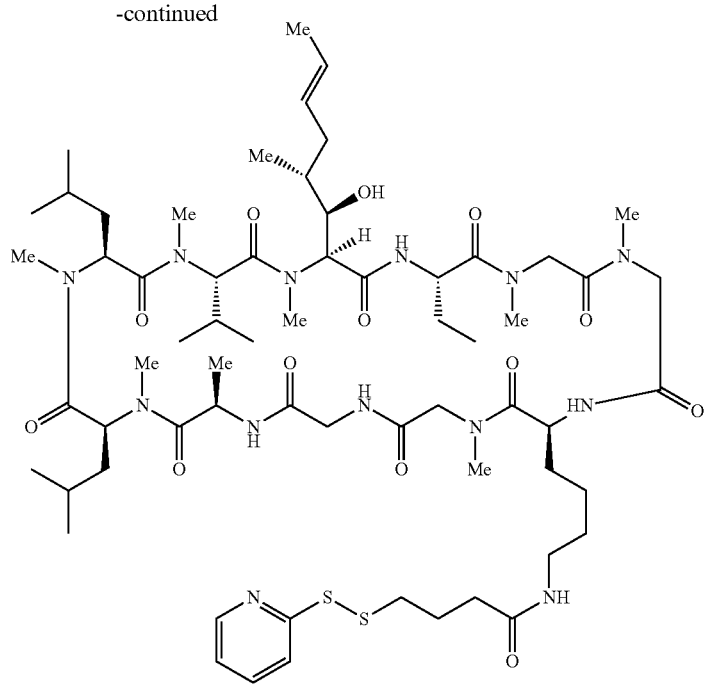

To a solution of amine 1 (100 mg, 90.5 µmol) and carboxylic acid 2 (31 mg, 135.2 µmol, 1.5 eq) in 6 mL of NMP was added HATU (51 mg, 134.1 µmol, 1.48 eq) and DIPEA (70 µL, 401.9 µmol, 4.4 eq). The reaction was stirred for 1 h at room temperature, then diluted with water and extracted with 3×30 mL portions of ethyl acetate. The organic extracts were washed with saturated sodium chloride solution and concentrated under vacuum. The crude material was purified by reversed phase chromatography on C18 media, eluting with gradient of 15% acetonitrile:85% water (both containing 0.1% formic acid) to 100% acetonitrile (containing 0.1% formic acid). MS (ESI) calc=658.9 (M+2H), obs=659.0.

Example 2: Synthesis of Certain Conjugates

General Protocol: This protocol describes a method for the formation of target protein-compound conjugates.

Reagents: Compound in 100% DMSO (in-house) and mammalian target protein (in-house)

Equipment: Mini-PROTEAN TGX Gel (Bio-Rad)

Experimental Protocol: A 1:2 molar ratio of target protein and compound are mixed together in 12.5 mM HEPES pH 7.4, 75 mM NaCl buffer containing 2% DMSO. The reaction is incubated at 37° C. for 30 min, followed by overnight incubation at room temperature. Cross-linking efficiency is assessed by SDS-PAGE gel. Conjugates migrate slower than non-cross-linked target protein. For thiol reactive compounds, the Cys specific attachment of the compound to the target protein can be further confirmed by SDS-PAGE after the addition of 100 mM DTT to the reaction mixture, which reduces the conjugate back into its components.

A. Formation of $KRAS_{GTP/S39C}$ Lite/C2-FK506 Conjugates

Reagents: C2-FK506 in 100% DMSO (in-house), $KRAS_{GTP/S39C}$ lite (in house; residues 1-169 containing G12V/S39C/C51 S/C80L/C118S).

Equipment: Mini-PROTEAN TGX Gel (Bio-Rad)

Experimental Protocol: A 1:2 molar ratio of $KRAS_{GTP/S39C}$ lite and C2-FK506 are mixed together in 12.5 mM HEPES pH 7.4, 75 mM NaCl buffer containing 2% DMSO. The reaction is incubated at 37° C. for 30 min, followed by overnight incubation at room temperature. Cross-linking efficiency is assessed by SDS-PAGE gel. Attachment of C2-FK506 to Cysteine 39 on $KRAS_{GTP/S39C}$ lite is also assessed by incubation of the reaction mixture with 100 mM DTT.

Results: C2-FK506 cross-links efficiently with $KRAS_{GTP/S39C}$ lite and is specific for Cysteine 39 (FIG. 1).

B. Formation of $KRAS_{GTP/G12C}$ Lite/SFAX9DS Conjugates

Reagents: SFAX9DS in 100% DMSO (in-house), $KRAS_{GTP/G12C}$ lite (in house; residues 1-169 containing G12C/C51S/C80L/C118S).

Equipment: Mini-PROTEAN TGX Gel (Bio-Rad)

Experimental Protocol: A 1:2 molar ratio of $KRAS_{GTP/G12C}$ lite and SFAX9DS are mixed together in 12.5 mM HEPES pH 7.4, 75 mM NaCl buffer containing 2% DMSO. The reaction is incubated at 37° C. for 30 min, followed by overnight incubation at room temperature. Cross-linking efficiency is assessed by SDS-PAGE gel. Wild-type CypA also cross-linked with the compound. Cysteine 52 as a reactive Cysteine on CypA and was mutated to Serine to abrogate presenter cross-linking.

Figure 2:
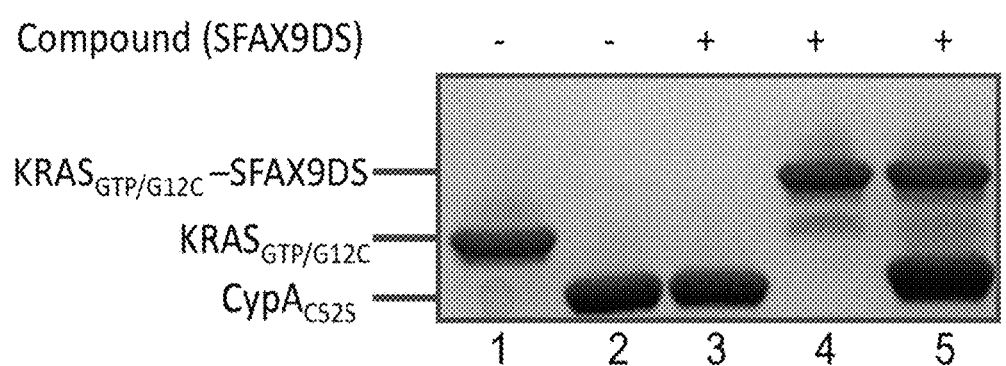
FIG. 2 is an image illustrating SDS-PAGE analysis of $KRAS_{GTP/G12C}$ lite/SFAX9DS conjugates.

Results: SFAX9DS cross-links efficiently with $KRAS_{GTP/G12C}$ lite protein and $CypA_{C52S}$ does not cross-link to SFAX9DS (FIG. 2).

Example 3: Formation of Certain Complexes

General Protocol: This protocol describes two methods for the formation and isolation of complexes comprised of presenter protein, compound, and mammalian target protein.

Reagents: Compound in 100% DMSO (in-house), presenter protein (in-house) and mammalian target protein (in-house)

Equipment: Mini-PROTEAN TGX Gel (Bio-Rad), Superdex 75 (GE Healthcare, CV 120 mL)

Experimental Protocol A: Pre-conjugated Compound and Protein

A 1:2 molar ratio of conjugate and presenter protein are mixed together in 12.5 mM HEPES pH 7.4, 75 mM NaCl buffer containing 2% DMSO. The reaction is incubated at 37° C. for 30 min, followed by overnight incubation at room temperature. Pure complex is isolated by Size Exclusion Chromatography (SEC) purification. The reaction mixture is directly injected on a Superdex 75 column (CV 120 mL) pre-equilibrated with buffer containing 12.5 mM HEPES pH 7.4, 75 mM NaCl. Complex elutes at a higher molecular weight than unreacted target protein and presenter protein. To confirm presence of complex in the elution peak, samples are assessed by SDS-PAGE.

Experimental Protocol B: Cross-linking reagent, presenter protein and target protein A 1:2:2 molar ratio of compound, presenter protein, and target protein are mixed together in 12.5 mM HEPES pH 7.4, 75 mM NaCl buffer containing 2% DMSO. The reaction is incubated at 37° C. for 30 min, followed by overnight incubation at room temperature. Pure complex is isolated by Size Exclusion Chromatography (SEC) purification. The reaction mixture is directly injected on a Superdex 75 column (CV 120 mL) pre-equilibrated with buffer containing 12.5 mM HEPES pH 7.4, 75 mM NaCl. Complex elutes at a higher molecular weight than unreacted target protein and presenter protein. To confirm presence of complex in the elution peak, samples are assessed by SDS-PAGE.

A. Formation of $KRAS_{GTP/S39C}$ Lite/C2-Holt/FKBP12 Ternary Complex

Reagents: C2-Holt in 100% DMSO (in-house), $KRAS_{GTP/S39C}$ lite (in house; residues 1-169 containing G12V/S39C/C51 S/C80L/C118S), and FKBP12 (in-house).

Equipment: Mini-PROTEAN TGX Gel (Bio-Rad), Superdex 75 (GE Healthcare, CV 120 mL)

Experimental Protocol: A 1:2:2 molar ratio of C2-Holt, FKBP12, and $KRAS_{GTP/S39C}$ lite are mixed together in 12.5 mM HEPES pH 7.4, 75 mM NaCl buffer containing 2% DMSO. The reaction is incubated at 37° C. for 30 min, followed by overnight incubation at room temperature. Pure complex is isolated by Size Exclusion Chromatography (SEC) purification. The reaction mixture is directly injected on a Superdex 75 column (CV 120 mL) pre-equilibrated with buffer containing 12.5 mM HEPES pH 7.4, 75 mM NaCl. Complex elutes at around 69 mL post injection and unreacted $KRAS_{GTP/S39C}$ lite and FKBP12 elutes at around 75 mL and 87 mL post injection respectively. To confirm the presence of $KRAS_{GTP/S39C}$ lite and FKBP12 in the elution peak, samples are also assessed by SDS-PAGE.

Figure 3A:
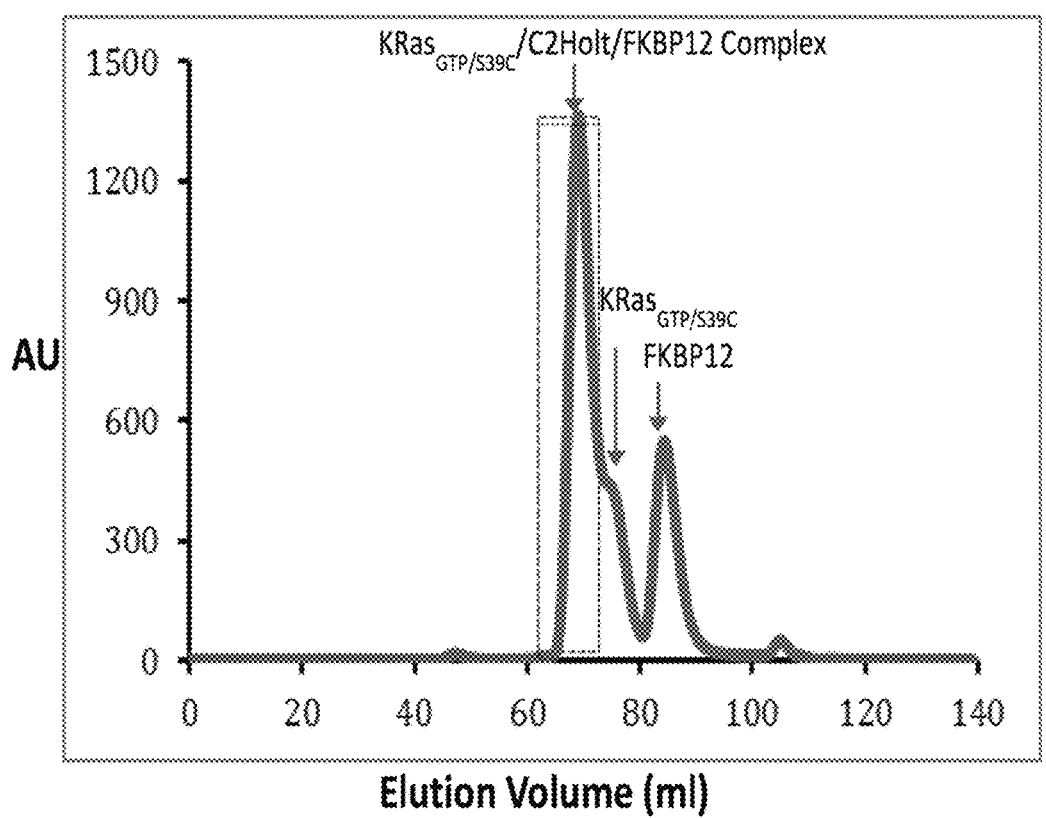
FIGS. 3A and 3B are images illustrating SEC and SDS-PAGE Analysis of $KRAS_{GTP/S39C}$ lite/C2-Holt/FKBP12 Complex Formation.
Figure 3B:
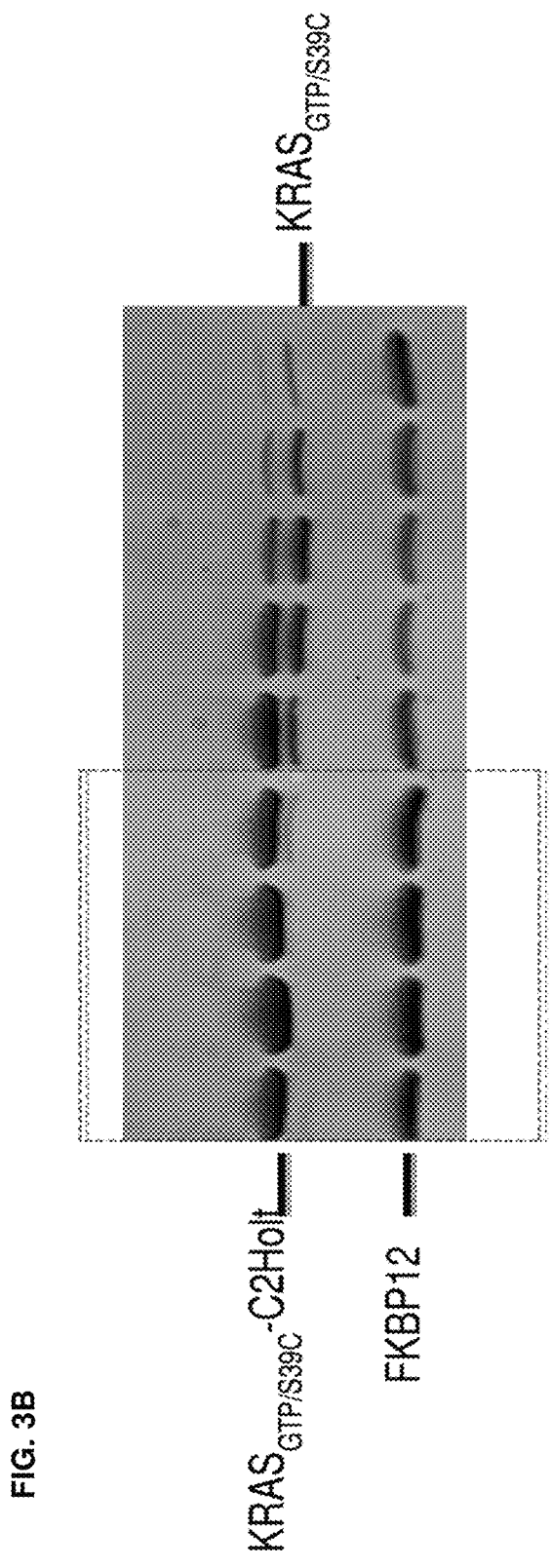

Results: The SEC profile and SDS-PAGE analysis of the elution peaks confirm the formation of $KRAS_{GTP/S39C}$ lite/C2-Holt/FKBP12 complex (FIGS. 3A and 3B).

B. Formation of $KRAS_{GDP/S39C}$ Lite/SFAC4DS/$CypA_{C52S}$ Ternary Complex

Reagents: SFAC4DS in 100% DMSO (in-house), $KRAS_{GDP/S39C}$ lite (in house; residues 1-169 containing G12V/S39C/C51 S/C80L/C118S), and $CypA_{C52S}$ (in-house).

Equipment: Mini-PROTEAN TGX Gel (Bio-Rad), Superdex 75 (GE Healthcare, CV 120 mL)

Experimental Protocol: A 1:2:2 molar ratio of SFAC4DS, $CypA_{C52S}$, and $KRAS_{GDP/S39C}$ lite are mixed together in 12.5 mM HEPES pH 7.4, 75 mM NaCl buffer containing 2% DMSO. The reaction is incubated at 37° C. for 30 min, followed by overnight incubation at room temperature. Pure complex is isolated by Size Exclusion Chromatography (SEC) purification. The reaction mixture is directly injected on a Superdex 75 column (CV 120 mL) pre-equilibrated with buffer containing 12.5 mM HEPES pH 7.4, 75 mM NaCl. Complex elutes at around 69 mL post injection and unreacted $KRAS_{GDP/S39C}$ lite and $CypA_{C52S}$ elutes at around 75 mL and 80 mL post injection respectively. To confirm the presence of $KRAS_{GDP/S39C}$ lite and $CypA_{C52S}$ in the elution peak, samples are also assessed by SDS-PAGE.

Results: The SEC profile and SDS-PAGE analysis of the elution peaks confirm the formation of $KRAS_{GDP/S39C}$ lite/SFAC4DS/$CypA_{C52S}$ complex (FIG. 4).

C. Formation of $PTP1B_{S187C}$ Lite/C3-SLF/FKBP12 Ternary Complex

Reagents: C3-SLF in 100% DMSO (in-house), $PTP1B_{E186C}$ lite (in house; residues 1-293 containing C32S/C92V/C121 S/S187C), and FKBP12 (in-house).

Equipment: Mini-PROTEAN TGX Gel (Bio-Rad), Superdex 75 (GE Healthcare, CV 120 mL)

Experimental Protocol: A 1:3:3 molar ratio of C3-SLF, FKBP12, and $PTP1B_{S187C}$ lite are mixed together in 12.5 mM HEPES pH 7.4, 75 mM NaCl buffer containing 4% DMSO. The reaction is incubated at 37° C. for 30 min, followed by overnight incubation at room temperature. Pure complex is isolated by Size Exclusion Chromatography (SEC) purification. The reaction mixture is directly injected on a Superdex 75 column (CV 120 mL) pre-equilibrated with buffer containing 12.5 mM HEPES pH 7.4, 75 mM NaCl. Complex elutes at around 62 mL post injection and unreacted FKBP12 elutes at around 75 mL (Dimer) and 90 mL (Monomer) post injection respectively. To confirm the presence of $PTP1B_{S187C}$ lite and FKBP12 in the elution peak, samples are also assessed by SDS-PAGE. Free $PTP1B_{S187C}$ lite and FKBP12 mixture are subjected to a Superdex 75 column under the same condition to determine their elution time.

Figure 5A:
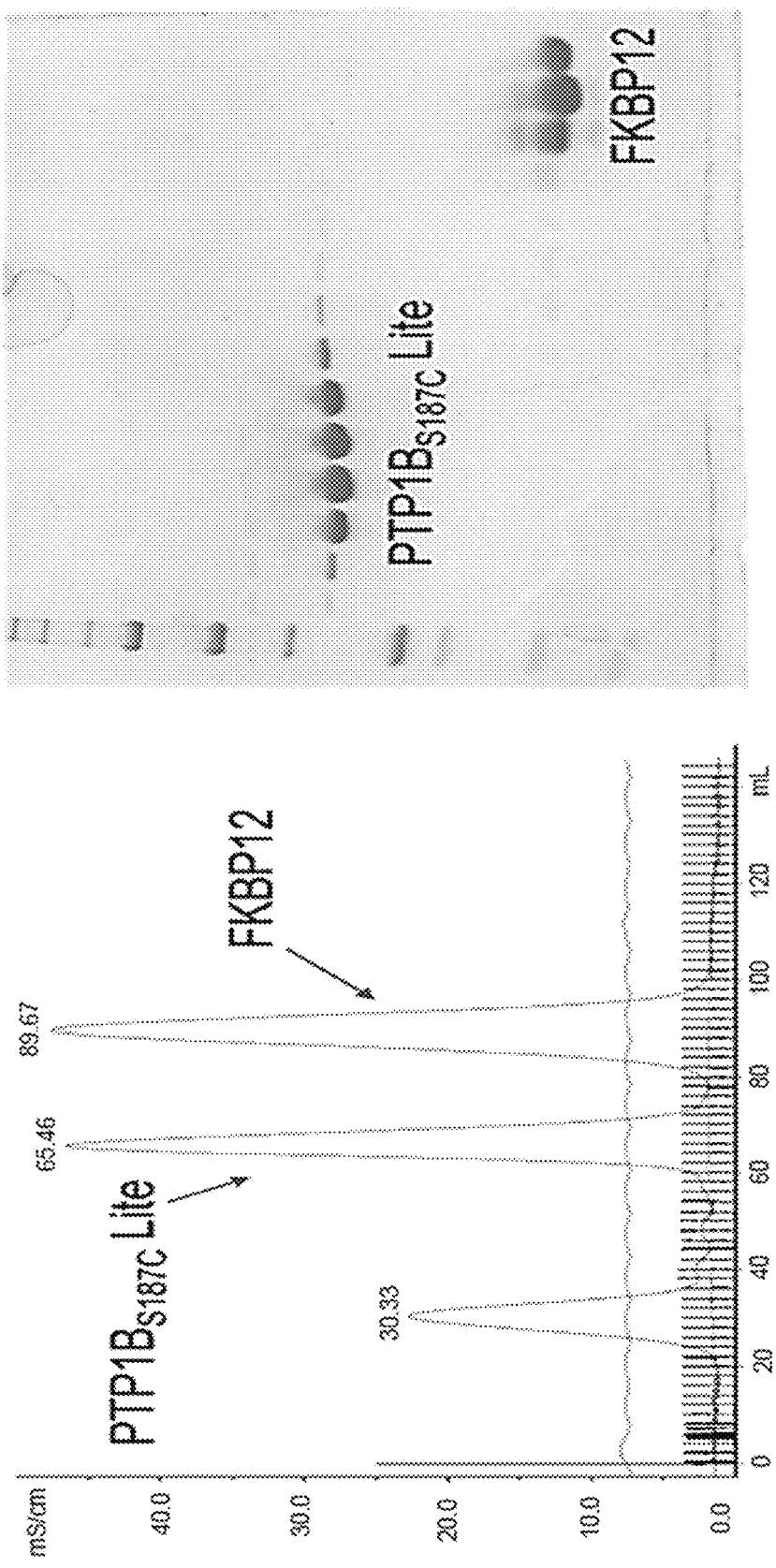
FIGS. 5A and 5B are images illustrating the SEC profile and SDS-PAGE analysis of free PTP1B$_{S187C}$ lite and FKBP12 proteins and the PTP1B$_{S187C}$ lite/C3-SLF/FKBP12 complex.
Figure 5B:
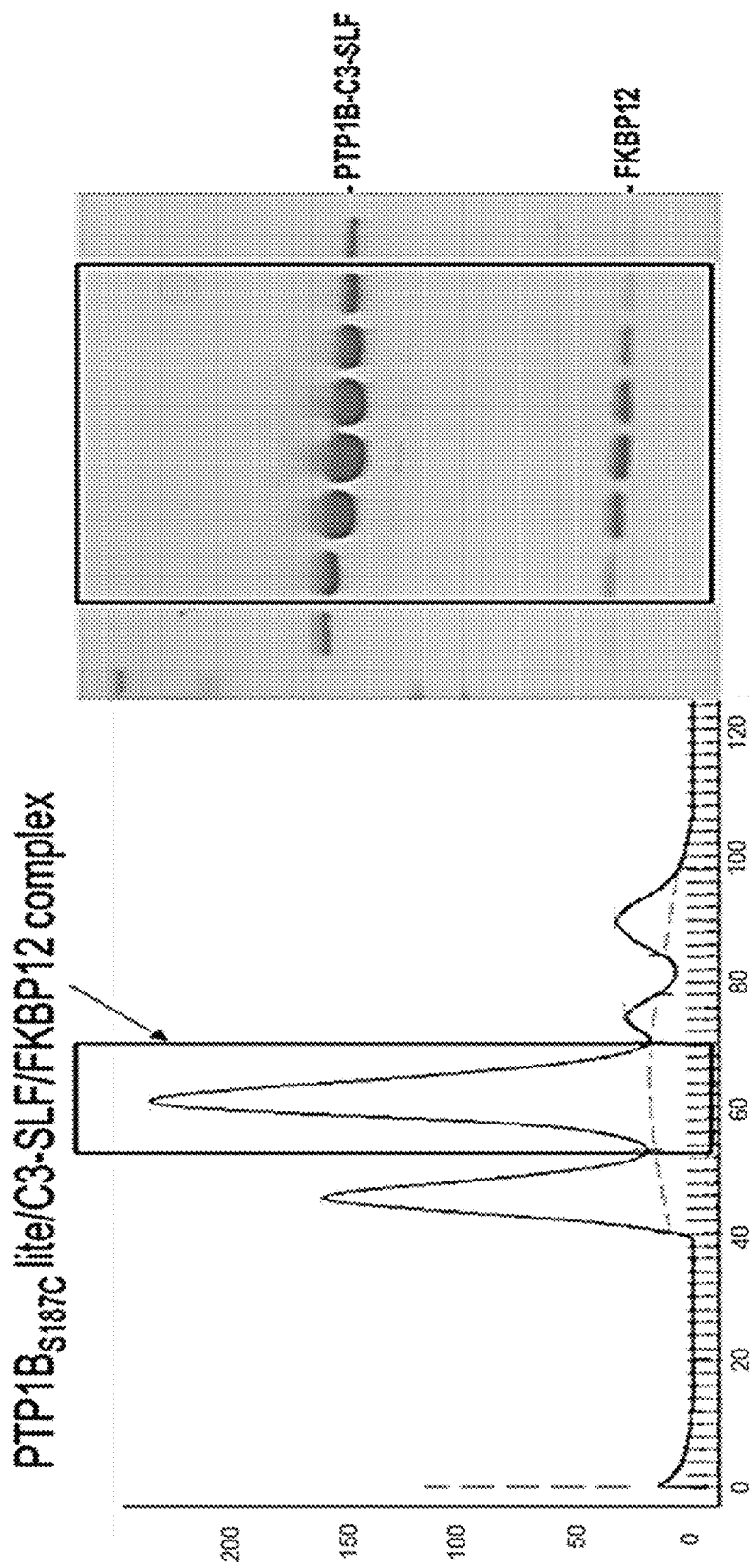

Results: The SEC profile and SDS-PAGE analysis of free $PTP1B_{S187C}$ lite and FKBP12 proteins (FIG. 5A) confirming the free $PTP1B_{S187C}$ lite elutes at around 64-65 ml. The SEC profile and SDS-PAGE analysis of the elution peaks confirm the formation of $PTP1B_{S187C}$ lite/C3-SLF/FKBP12 complex, which elutes at around 61 ml (FIG. 5B).

Example 4: Conjugate Formation when Presenter Protein is Present, but not when it is Absent This protocol describes methods to analyzing cross-linking efficiency using mass spectrometry and gel shift assay in effort to assess the presenter dependency of conjugate formation.

Reagents: Compound in 100% DMSO (in-house), FKBP12 (in-house), $KRAS_{GTP/G12C}$ (in-house, residues 1-169).

Experimental Protocol: In order to follow the kinetics of disulfide crosslinking reactions, Agilent 6230 TOF-LC/MS and Agilent 1260 HPLC instruments employing a Advance-Bio RP-mAb C4 column (2.1×100 mm, 3.5 μm) and equipped with an auto-sampler were used. HPLC grade acetonitrile and water (each containing 1.0 mM ammonium formate and 1% formic acid by volume) were used as mobile phase with the following ramp: 0.6 ml/min flow rate, water:acetonitrile=95:5 from 0.0 to 13.0 min ramping to water:acetonitrile=5:95 from 13.0 to 17.0 min. Total time=17.0 min.

All crosslinking reactions were performed in 1.5 mL amber colored glass vials equipped with 0.5 mL glass inserts. A water-soluble peptide (SEQ ID NO: 1: YQNLL-VGRNRGEEILD) was employed as an internal standard.

Although the actual sequence of the internal standard is inconsequential, choice of amino acid residues were critical to avoid interference in the crosslinking assays. Hence, proline (interfering with FKBP12) and cysteine (interfering with disulfide bond formation) residues were excluded. All reactions and standard solutions were prepared in HEPES (pH 7.4, 1.0 mM $MgCl_2$) buffer.

Prior to every reaction, a standard curve was obtained for the individual components using a series of standard solutions (an example of standard curve analysis for FKBP12 is shown in Table 3 below). Using the data from standard curve, µmol of protein samples were plotted against the ratio of areas (sample:std) and a linear fit (y=mx+c) was employed to obtain the slope and intercept. The value of slope and intercept involved in these standard curves were accounted for during evaluation of the substrate and product concentration before and during the course of the reaction. For every substrate/product, an initial injection was followed up by a blank injection to verify presence of any residual protein/reagents. Based on this analysis the sequence of auto-sampler can be adjusted to included appropriate number of blank injections for removal of residual components, if any. The MS spectra were analyzed using Agilent MassHunter v B.07.0 software.

TABLE 3

Standard curve for FKBP12. Slope = 6.53, Intercept = −0.64, $R^2$ = 0.999

| Solution | Concentration (mM) | Area under internal standard ($R_t$ = 7.1 min) | Area under FKBP-12 ($R_t$ = 8.9 min) | Ratio of Sample:Std |
|---|---|---|---|---|
| 1 | 100 | 2615940.1 | 40314760.1 | 15.41 |
| 2 | 10 | 5244417.4 | 8718886.5 | 1.66 |
| 3 | 1 | 5868006.9 | 1745344.5 | 0.30 |
| 4 | 0.5 | 5407354.8 | 910748.2 | 0.17 |
| 5 | 0.1 | 5626447.0 | 237074.5 | 0.04 |

In a representative experiment to assess the presenter dependency of ligand cross-linking on the target protein, $KRAS_{GTP/G12C}$ and either C3- or C4-SLF ligand were incubated in the presence or absence of FKBP12 at concentrations of 2 µM KRAS, 10 µM FKBP12, 10 µM C3- or C4-SLF for 4 hours at room temperature in 12.5 mM HEPES pH 7.4, 75 mM NaCl, 1 mM $MgCl_2$, 3% DMSO. Analysis of the amount of KRAS undergoing disulfide cross-linking with the ligand using the method above. As shown in Table 4, 5- to 10-fold increased cross-linking efficiency was observed in the presence of the presenter:

TABLE 4

Crosslinking efficiency of C3- and C4-SLF analyzed MS

|  | C3-SLF | | C4-SLF | |
|---|---|---|---|---|
| FKBP12 | − | + | − | + |
| % xlink to KRAS | 9.6 | 47.5 | 7.0 | 69.8 |

Figure 6:
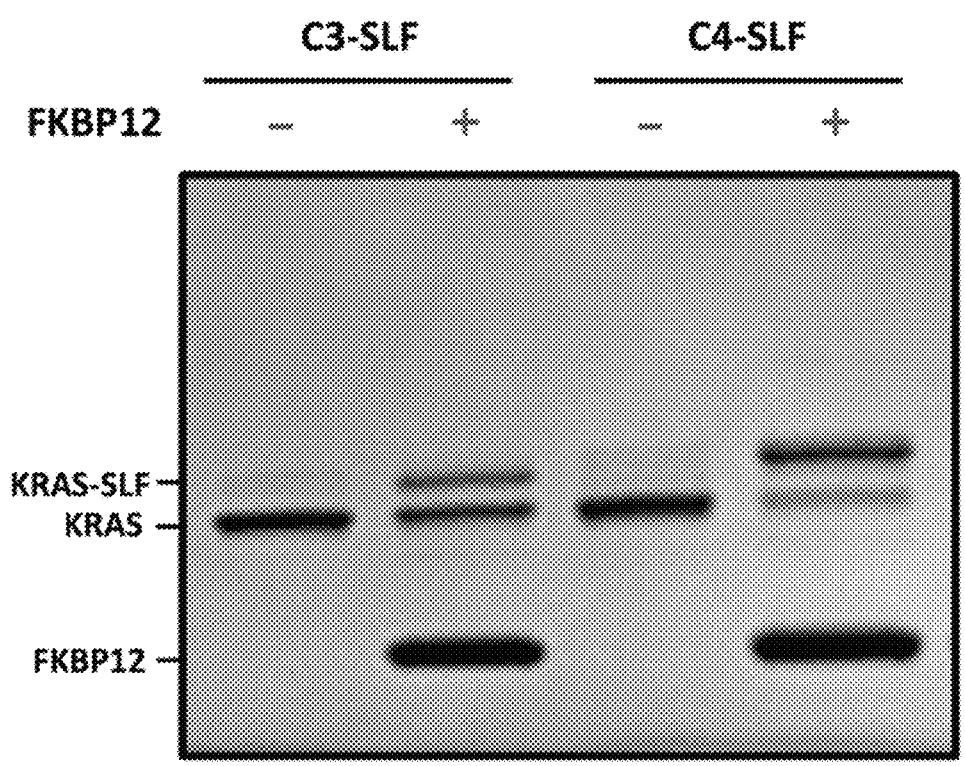
FIG. 6 is an image illustrating crosslinking efficiency of C3- and C4-SLF by SDS-PAGE.

In parallel to mass spectrometry analysis, cross-linking reactions with C3- or C4-SLF were subjected to gel shift assay using 12% SDS-PAGE in the presence or absence of FKBP12 at the same experimental condition described above except that cross-linking reactions were set up at higher concentrations (60 µM KRAS, 180 µM FKBP12, and 180 µM C3- or C4-SLF) and they were quenched by MMTS to terminate the reaction. Similar to the MS data, the ligand cross-linking efficiency was boosted significantly in the presence of FKBP12, which is more pronounced for C4-SLF (FIG. 6).

Example 5: Determination of Presenter Protein/Target Protein Interface Structure by X-ray Analysis This protocol describes the crystallization and structure determination method for the crystal structure of a ternary complex of FKBP12-C2Holt-$KRAS_{GTP/S39C}$.

A. Crystal Structure Determination of FKBP12-C2Holt-$KRAS_{GTP/S39C}$ Ternary Complex Reagents: Ligand (C2Holt) in 100% DMSO (in-house), FKBP12 (in-house), $KRAS_{GTP/S39C}$ lite (in-house, residues 1-169 containing G12V/S39C/C51S/C80L/C118S).

Equipment: Superdex 75 (GE Healthcare)

Experimental Protocol: C Holt and FKBP12 were added to $KRAS_{GTP/S39C}$ lite at 3:1 and 1.5:1 molar excess in 12.5 mM HEPES pH 7.4, 75 mM NaCl buffer, 1 mM $MgCl_2$, 2% DMSO, and incubated overnight at 20° C. or 36-72 hours at 4° C. Pure complex was isolated by size exclusion chromatography on a Superdex 75 column in 12.5 mM HEPES pH 7.4, 75 mM NaCl, and 1 mM $MgCl_2$. Purified complex (at 15-20 mg/ml) was subjected to crystallization screening at 20° C. using sitting drop vapor diffusion method. Crystals were grown in a well solution containing 0.1 M MES pH 6.5, 20-22% PEG 20,000. For data collection crystals were transferred to a solution containing mother liquor supplemented with 15% glycerol, and then frozen in liquid nitrogen. Diffraction datasets were collected at the Advanced Photon Source (APS) and processed with the HKL program. Molecular replacement solutions were obtained using the program PHASER in the CCP4 suite, using the published structure of FKBP12 (PDB-ID 1 FKD) and KRAS (PDB-ID 3GFT) as search models. Subsequent model building and refinement were performed according to standard protocols with the software packages CCP4 and COOT.

Figure 7A:
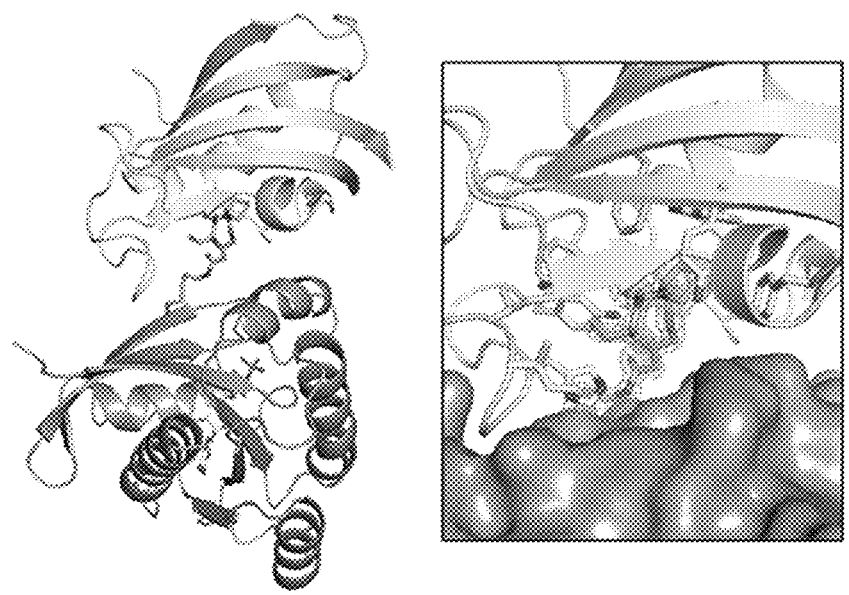
FIGS. 7A and 7B is an image illustrating the crystal structure of FKBP12-Compound 1-$KRAS_{GTP/S39C}$ complex.
Figure 7B:
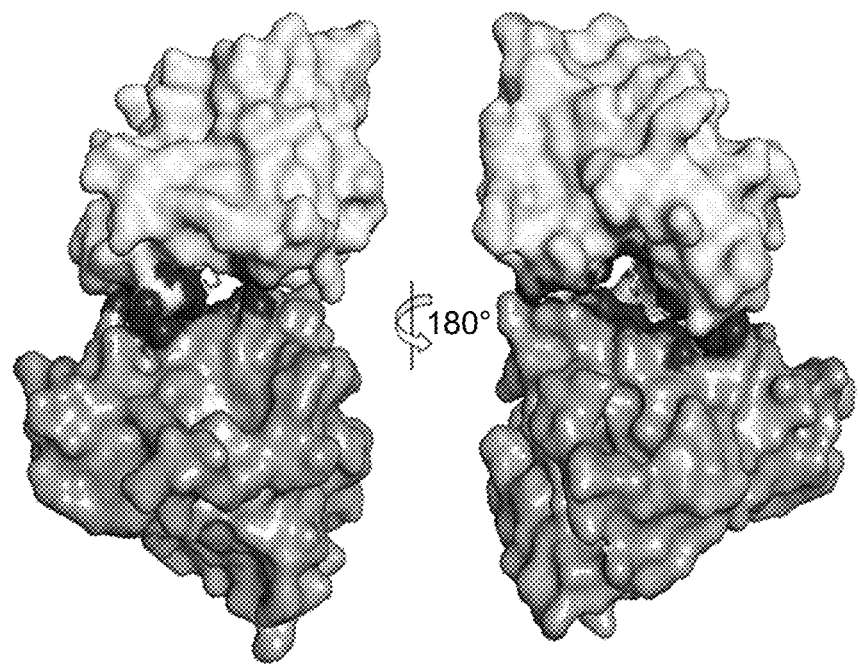

Results: Overall structure of FKBP12-C2Holt-$KRAS_{GTP/S39C}$: The crystal contains one heterodimer of FKBP12 and $KRAS_{GTP/S39C}$ in the asymmetric unit (FIG. 7). The model comprised residues Met1 to Glu108 of FKBP12 and Met1 to Lys169 of $KRAS_{GTP/S39C}$. The resulting electron density shows unambiguous binding mode, including the orientation and conformation of the ligand. The continuous electron density was observed for the disulfide generated from the cysteine of the protein and the sulfur from the ligand.

The $KRAS_{GTP/S39C}$ residues involved in binding C2Holt (4 Å distance cut-off) are Glu37, Cys39, Leu56, and Met67. The $KRAS_{GTP/S39C}$ residues involved in binding to FKBP12 are Glu3, Lys5, Ile36, Cys39, Tyr40, Arg41, Asp54, Glu63, Tyr64, Met67, and Arg73. The FKBP12 residues involved in binding $KRAS_{GTP/S39C}$ are Arg43, Lys53, Gln54, Glu55, Thr86, Pro89, Gly90, and Ile92. The FKBP12 residues involved in binding C2Holt are Tyr27, Phe37, Asp38, Phe47, Glu55, Val56, Ile57, Trp60, Tyr83, His88, Ile91, Ile92, and Phe100.

The total buried surface area of the complex is 1,947 Å$^2$. The buried surface area of $KRAS_{GTP/S39C}$ is 600 Å$^2$ of which 501 Å$^2$ is contributed by FKBP12 (83%), and 99 Å$^2$ contributed by C2Holt (17%). The buried surface area of FKBP12 is 762 Å$^2$ of which 500 Å$^2$ contributed by $KRAS_{GTP/S39C}$ (66%) and 262 Å$^2$ contributed by C2Holt (34%). The buried surface area of $C_2$ Holt is 584 Å$^2$ of which 132 Å$^2$ contributed by $KRAS_{GTP/S39C}$ (23%) and 452 Å$^2$ contributed by FKBP12 (77%). The protein-protein interface between KRAS$_{GTP/S39C}$ and FKBP12 is formed by both hydrophobic and polar interactions, including three intermolecular H-bonds. The binding interface between C$_2$ Holt and FKBP12 is largely contributed by hydrophobic interactions, but also contributed by three H-bonds between three carbonyl groups of the ligand and Tyr27, Ile57, and Tyr83 of FKBP12. C$_2$ Holt forms minimal contact with KRAS$_{GTP/S39C}$ by design (99 Å$^2$) but forms one H-bond with Glu37 of KRAS$_{GTP/S39C}$. Data collection and refinement statistics of the final structure are listed in Table 5 below.

B. Crystal Structure Determination of KRAS$_{GDP/S39C}$/SFAC4DS/CypA$_{C52S}$ Ternary Complex Reagents: Ligand (SFAC4DS) in 100% DMSO (in-house), CypA$_{C52S}$ (in-house), KRAS$_{GDP/S39C}$ lite (in-house, residues 1-169 containing G12V/S39C/C$_{51}$S/C$_{80}$L/C$_{118}$S).

Equipment: Superdex 75 (GE Healthcare)

Experimental Protocol: SFAC4DS and CypA$_{C52S}$ were added to KRAS$_{GDP/S39C}$ lite at 2:1 and 2:1 molar excess in 12.5 mM HEPES pH 7.4, 75 mM NaCl buffer, 1 mM MgCl$_2$, 2% DMSO, and incubated overnight at 20° C. Pure complex was isolated by size exclusion chromatography on a Superdex 75 column in 12.5 mM HEPES pH 7.4, 75 mM NaCl, and 1 mM MgCl$_2$. Purified complex (at 15 mg/ml) was subjected to crystallization screening at 20° C. using sitting drop vapor diffusion method. Crystals were grown in a well solution containing 0.1 M Bis-Tris pH 6.5, 25% PEG 3350. For data collection, crystals were transferred to a solution containing mother liquor supplemented with extra PEG 3350 to make it 40% of PEG, and then frozen in liquid nitrogen. Diffraction datasets were collected at the Advanced Light Source (ALS) and processed with the HKL program. Molecular replacement solutions were obtained using the program PHASER in the CCP4 suite, using the published structure of CypA (PDB-ID 1CWA) and KRAS (PDB-ID 3GFT) as search models. Subsequent model building and refinement were performed according to standard protocols with the software packages CCP4 and COOT.

Results: Overall structure of CypA$_{C52S}$-SFAC4DS-KRAS$_{GDP/S39C}$: The crystal contains one heterodimer of CypA$_{C52S}$ and KRAS$_{GDP/S39C}$ in the asymmetric unit (FIG. 8). The model comprised residues Met1 to Glu165 of CypA and Met1 to Lys169 of KRAS$_{GDP/S39C}$. The resulting electron density shows unambiguous binding mode, including the orientation and conformation of the ligand. The continuous electron density was observed for the disulfide generated from the cysteine of the protein and the sulfur from the ligand.

The KRAS$_{GDP/S39C}$ residues involved in binding SFAC4DS (4 Å distance cut-off) are Glu3, Lys5, Cys39, Arg41, Leu52, Asp54, Ile55 and Leu56. The KRAS$_{GDP/S39C}$ residues involved in binding to CypA$_{C52S}$ are Glu37, Asp38, Cys39, Arg41, Gln43, Leu56, Ala66, Met67, Gln70, and Thr74. The CypA$_{C52S}$ residues involved in binding KRAS$_{GDP/S39C}$ are Arg55, Ile57, Arg69, Asn71, Thr73, Ala81, Ala103, Arg148, and Asn149. The CypA$_{C52S}$ residues involved in binding SFAC4DS are Arg55, Phe60, Met61, Gln63, Gly72, Ala101, Asn102, Gln111, Phe113, and His126.

The total buried surface area of this complex cannot be calculated due to partial structural disorder at the protein-protein interface. Excluding the disordered region for calculation, the buried surface area at the protein-protein interface is greater than 1,350 Å$^2$, of which over 30% is contributed by SFAC4DS (443 Å$^2$). The protein-protein interface between KRAS$_{GDP/S39C}$ and CypA$_{C52S}$ is formed by both hydrophobic and polar interactions, including two intermolecular H-bonds. The binding interface between SFAC4DS and CypA is contributed both by hydrophobic and polar interactions. There are six H-bonds between carbonyl and N—H groups of the ligand and residues Arg55, Gln63, Asn102, and His126 of CypA$_{C52S}$. SFAC4DS forms minimal direct contact with KRAS$_{GDP/S39C}$ but forms one H-bond with Arg41 of KRAS$_{GDP/S39C}$. Data collection and refinement statistics of the final structure are listed in Table 5 below.

C. Crystal Structure Determination of PTP1B$_{S187C}$/C3SLF/FKBP12 Ternary Complex Reagents: Ligand (C3-SLF) in 100% DMSO (in-house), FKBP12 (in-house), PTP1B$_{S187C}$ lite (in-house, residues 1-169 containing C32S/C92V/C121 S/S187C).

Equipment: Superdex 75 (GE Healthcare), Gryphon (Art Robbins Instruments)

Experimental Protocol: C3SLF and FKBP12 were added to PTP1B$_{S187C}$ lite at 3:1 molar excess in 12.5 mM HEPES pH 7.4, 75 mM NaCl buffer, 4% DMSO, and incubated 36-72 hours at 4° C. Pure complex was isolated by size exclusion chromatography on a Superdex 75 column in 12.5 mM HEPES pH 7.4 and 75 mM NaCl. Purified complex (at 15 mg/ml) was subjected to crystallization screening at 20° C. using sitting drop vapor diffusion method. Crystals were grown in a well solution containing 0.2 M Magnesium Acetate, 20% w/v PEG 3350. For data collection, crystals were transferred to a solution containing mother liquor supplemented with 25% PEG400, and then frozen in liquid nitrogen. Diffraction datasets were collected at the Advanced Photon Source (APS) and processed with the XDS program. Molecular replacement solutions were obtained using the program PHASER in the CCP4 suite, using the published structure of FKBP12 (PDB-ID 2PPN) and PTP1B (PDB-ID 2NT7) as search models. Subsequent model building and refinement were performed according to standard protocols with the software packages CCP4 and COOT.

Figure 9A:
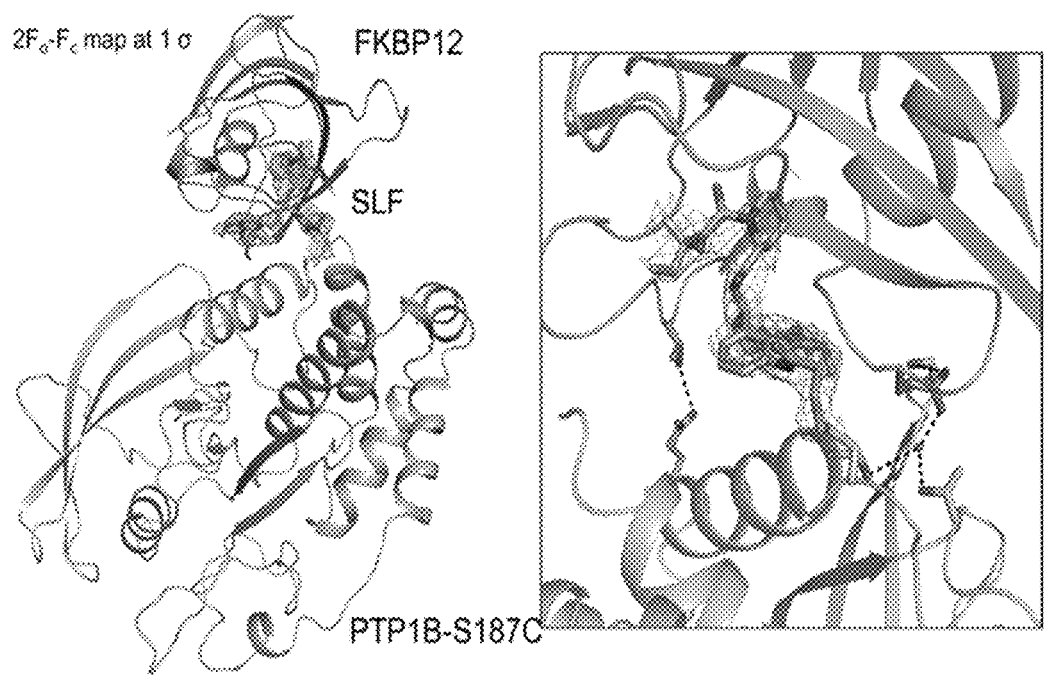
FIGS. 9A and 9B are images illustrating the crystal structure of FKBP12-C3SLF-PTP1B$_{S187C}$.

Results: Overall structure of FKBP12-C3SLF-PTP1B$_{S187C}$: The crystal contains two complex molecules of FKBP12-C3SLF-PTP1B$_{S187C}$ in the asymmetric unit (FIG. 9A). The model comprised residues Gly2 to Glu108 of FKBP12 and Glu6 to Phe280 of PTP1B$_{S187C}$. The resulting electron density shows unambiguous binding mode, including the orientation and conformation of the ligand. The continuous electron density was observed for the disulfide generated from the cysteine of the protein and the sulfur from the ligand.

Figure 9B:
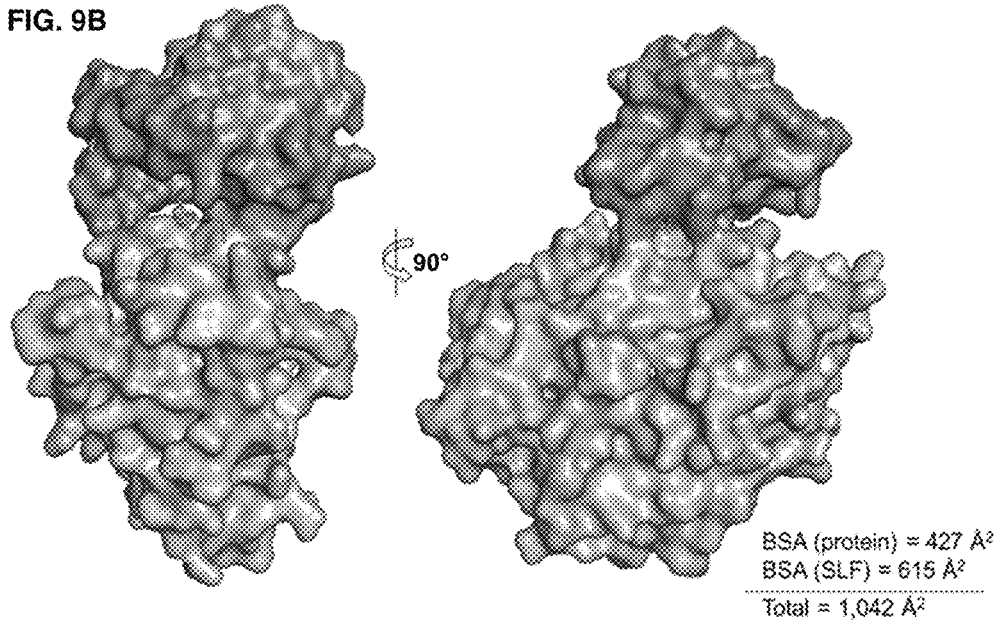

The total buried surface area of the complex is 1,042 Å$^2$. The buried surface area of PTP1B$_{S187C}$ is 427 Å$^2$. The buried surface area of C3-SLF is 615 Å$^2$ (FIG. 9B). The protein-protein interface between PTP1B$_{S187C}$ and FKBP12 is formed by both hydrophobic and polar interactions.

D. Crystal Structure Determination of MCL1$_{S245C}$/C3SLF/FKBP52 Ternary Complex Reagents:

Ligand (C3-SLF) in 100% DMSO (in-house), FKBP52 (in-house, residues 1-140), MCL1 S245C lite (in-house, residues 172-327 containing S245C/C286S).

Equipment: Superdex 75 (GE Healthcare), Gryphon (Art Robbins Instruments)

Experimental Protocol: C3SLF and FKBP52 were mixed with MCL1$_{S245C}$ lite at 3:1 molar excess in 12.5 mM HEPES pH 7.4, 75 mM NaCl buffer, 2% DMSO, and incubated 24-48 hours at 4° C. Pure complex was isolated by size exclusion chromatography on a Superdex 75 column in 12.5 mM HEPES pH 7.4 and 75 mM NaCl. Purified complex (at 15 mg/ml) was subjected to crystallization screening at 20° C. using sitting drop vapor diffusion method. Crystals were grown in a well solution containing 2.1 M Malic acid. For data collection, crystals were transferred to a solution containing mother liquor supplemented with 20% glycerol, and then flash-frozen in liquid nitrogen. 3.0 Å resolution diffraction dataset was measured at the Advanced Photon Source (APS) and processed with the XDS program. Molecular replacement solutions were obtained using the program PHASER in the CCP4 suite, using the published structure of FKBP52 (PDB-ID 1N1A) and PTP1B (PDB-ID 3MK8) as search models. Subsequent model building and refinement were performed according to standard protocols with the software packages CCP4 and COOT.

Results: The crystal contains one complex molecule of MCL1$_{S245C}$/C3SLF/FKBP52 in the asymmetric unit (FIG. 10). The resulting electron density revealed unambiguous binding between two proteins, including the orientation and conformation of the ligand. The continuous electron density was observed for the disulfide generated from the cysteine of the protein and the sulfur from the ligand. The total buried surface area of the complex is 1,410 Å$^2$, of which approximately 60% is contributed by FKBP52 (804 Å$^2$), and approximately 40% by C3-SLF (606 Å$^2$). Due to the limited resolution, the detailed analysis in the protein-protein and protein-ligand interaction was not feasible.

complex formation are identified as those eliciting an increase in the TR-FRET ratio relative to DMSO control wells.

Determination of CYPA-Compound 3-KRAS$_{G12C\text{-}GTP}$ Complex Formation by TR-FRET Avi-tagged Cyclophilin A and His-tagged KRAS G12C-GTP were mixed with increasing concentration of ligand (Compound 3) and incubated at room temperature for 15 minutes to allow formation of ternary complex. A pre-mixture of Anti-His Eu—W1024 and Streptavidin APC were then added and incubated for 60 minutes. TR-FRET signal is read on an EnVision microplate reader (Perkin Elmer, Ex 320 nm, Em 665/615 nm). A counter screen without presenter and target protein is also run to rule out the contribution of compounds alone.

Reagents and Instrument
His6-KRAS$_{G12C\text{-}GTP}$ (in house; residues 1-169); 1.2 mM in PBS buffer, pH 7.4
Avi-CYPA (in house; residues 1-165); 556 µM in PBS buffer, pH 7.4
Anti-His Eu—W1024 (Perkin Elmer)
Streptavidin APC (Perkin Elmer)
Ligand (W21487), 10 mM in 100% DMSO
EnVision (Perkin Elmer)

TABLE 5

Data collection and refinement statistics

|  | Structure A | Structure B | Structure C | Structure D |
| --- | --- | --- | --- | --- |
| Resolution [Å] | 47.8-1.4 | 70.1-1.6 | 49.0-2.4 | 65.9-3.0 |
| Number of reflections (working/test) | 50,557/2,708 | 34,377/1,790 | 30,175/1,543 | 5,343/245 |
| R$_{cryst}$ [%] | 18.9 | 17.9 | 23.0 | 33.2 |
| R$_{free}$ [%][1] | 21.7 | 21.2 | 28.1 | 37.8 |
| Total number of atoms: | | | | |
| Protein | 2,202 | 2,528 | 6,192 | 2,035 |
| Water | 268 | 171 | 38 | 0 |
| Ligands | 69 | 63 | 43 | 43 |
| Ions | 1 | 1 | 0 | 0 |
| Deviation from ideal geometry:[2] | | | | |
| Bond lengths [Å] | 0.007 | 0.011 | 0.004 | 0.010 |
| Bond angles [°] | 1.33 | 1.49 | 0.87 | 1.30 |
| Ramachandran plot:[3] | | | | |
| Most favoured regions [%] | 93.8 | 96.5 | 93.3 | 95.2 |
| Allowed regions [%] | 6.2 | 3.1 | 4.9 | 4.4 |
| Disallowed region [%] | 0.0 | 0.3 | 1.8 | 0.4 |

[1]Test-set contains 5% of measured reflections
[2]Root mean square deviations from geometric target values
[3]Calculated with RAMPAGE Example 6: Determination of Complex Formation by TR-FRET TR-FRET technology (LANCE, Perkin Elmer) is a standard method to detect the binary association of two fusion-tagged proteins, e.g., protein 1/tag A and protein 2/tag B, where A and B can be any of glutathione-S-transferase (GST), hexahistidine (His$_6$), FLAG, biotin-avi, Myc, and Hemagglutinin (HA). In this example, the technology is used to measure the compound-facilitated association of a presenter protein with a target protein. A mixture of a presenter protein/tag A and a target protein/tag B are added to a 384-well assay plate containing compounds of the invention and incubated for 15 minutes. A mixture of anti-fusion tag A or B Europium-chelate donor and anti-fusion tag A or B allophycocyanin acceptor or Ulight acceptor reagents are added and the reactions are incubated for 240 minutes. The TR-FRET signal is read on an Envision microplate reader (Perkin Elmer) using excitation=320 nm, emission=665/615 nm. Compounds that facilitate ternary Combi Mutidrop liquid dispenser with 8-channel small volume cassette
384-w ProxiPlate (black)
Experimental Protocol
1. Use Mosquito to dispense 100 nL/well of compounds (varying concentration in DMSO) into 384-w black ProxiPlate to make assay-ready-plate (ARP).
2. Make 2× assay buffer containing 40 mM Hepes pH 8.0, 200 mM NaCl, 2 mM MgCl$_2$, 0.1% BSA and 0.004% Tween-20.
3. Make 2×PRE-MIX A: 100 nM of His6-KRas G12C-GTP (1-169) and 1000 nM of Avi-CypA (1-165) in 1× assay buffer.
4. Use MutiDrop Combi to dispense 2×PRE-MIX A into ARP, 5 µl/well. Incubate 15 min at RT.
5. Make 2×PRE-MIX B: 10 nM of anti-His Eu—W1024 and 40 nM of SA APC.
6. Use MutiDrop Combi to dispense 2×PRE-MIX B into ARP, 5 µl/well. Shake briefly on Combi and incubate 60 min at RT.

7. Read on EnVision (Ex: 320 nm; Em1: 615 nm; Em2: 665 nm).
8. Data is processed using Dotmatics. Curves are fit using a 4 parameter non-linear fit to determine the EC50 value for formation of the ternary complex.

Figure 11:
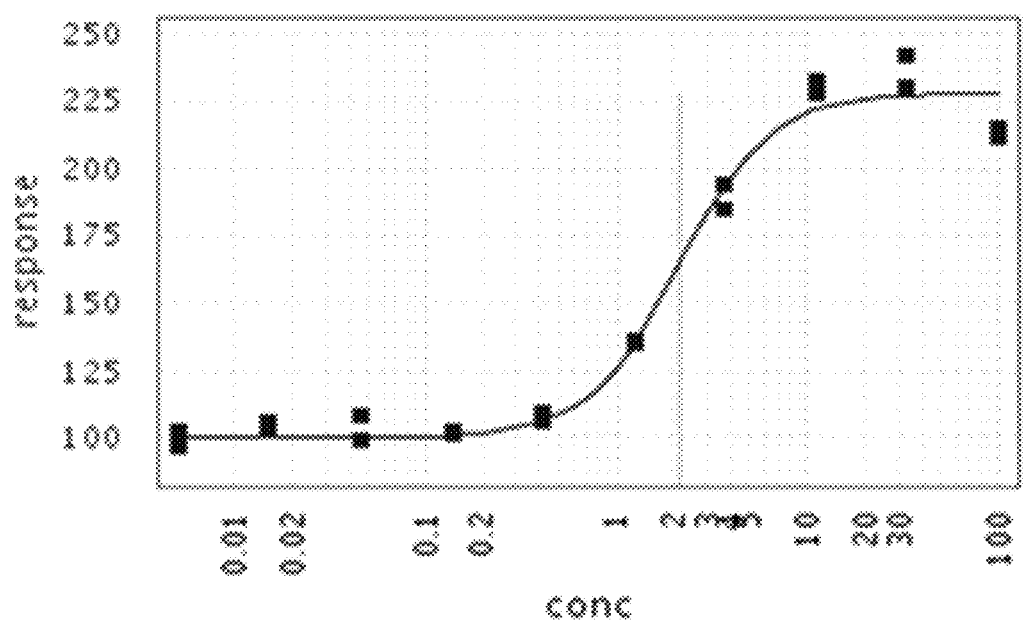
FIG. 11 is an image illustrating the binding curve of W21487 dependent complex formation of CYPA-W21487-KRAS$_{G12C\text{-}GTP}$ ternary complex.

Results: The binding curve (FIG. 11) demonstrates Compound 3 dependent complex formation of CYPA-Compound 3-KRAS$_{G12C\text{-}GTP}$ ternary complex, with a calculated EC50 value of 2.1 µM Example 7: Determination of Complex Formation by Amplified Luminescent Proximity Homogeneous Assay AlphaScreen technology (Perkin Elmer) is a standard method to detect the binary association of two fusion-tagged proteins, e.g., protein 1/tag A and protein 2/tag B, where A and B can be any of glutathione-S-transferase (GST), hexahistidine (His$_6$), FLAG, biotin-avi, Myc, and Hemagglutinin (HA). In this example, the technology is used to measure the compound-facilitated association of a presenter protein with a target protein. A mixture of presenter protein/tag A and target protein/tag B are added to a 384-well assay plate containing compounds of the invention and incubated for 15 minutes. A mixture of anti-fusion tag A or B AlphaScreen donor beads and anti-fusion tag A or B AlphaScreen acceptor beads are added and the reactions are incubated for 240 minutes. The AlphaScreen signal is read on an Envision microplate reader (Perkin Elmer) using excitation=680 nm, emission=585 nm. Compounds that facilitate ternary complex formation are identified as those eliciting an increase in the AlphaScreen signal relative to DMSO control wells.
Determination of CYPA-Compound 3-KRAS$_{G12C\text{-}GTP}$ Complex Formation by Alpha LISA Avi-tagged Cyclophilin A and His-tagged KRAS G12C-GTP were mixed with increasing concentration of ligand (Compound 3) and incubated at room temperature for 60 minutes to allow formation of ternary complex. A pre-mixture of Nickel chelate donor beads and Streptavidin acceptor beads were then added and incubated for 60 minutes. AlphaLISA signal is read on an EnVision microplate reader (Perkin Elmer, Ex 680 nm, Em 615 nm). A counter screen without presenter and target protein is also run to rule out the contribution of compounds alone.

Reagents and instrument:
His6-KRAS$_{G12C\text{-}GTP}$ (in house; residues 1-169); 1.2 mM in PBS buffer, pH 7.4
Avi-CYPA (in house; residues 1-165); 556 uM in PBS buffer, pH 7.4
Nickel chelate donor beads (Perkin Elmer)
Streptavidin acceptor beads (Perkin Elmer)
Ligand (W21487), 10 mM in 100% DMSO
EnVision (Perkin Elmer)
Combi Mutidrop liquid dispenser with 8-channel small volume cassette
alphaPlate-384 plate (white)

Experimental Protocol:
1. Use Mosquito to dispense 100 nL/well of compounds (varying concentration in DMSO) into 384-well black ProxiPlate to make assay-ready-plate (ARP).
2. Make 2× assay buffer containing 40 mM Hepes pH 8.0, 200 mM NaCl, 2 mM MgCl$_2$ and 0.004% Tween-20.
3. Make 2×PRE-MIX A: 300 nM of His6-KRas G12C-GTP (1-169) and 300 nM of Avi-CypA (1-165) in 1× assay buffer.
4. Use MutiDrop Combi to dispense 2×PRE-MIX A into ARP, 5 µl/well. Incubate 60 min at RT.
5. Make 2×PRE-MIX B: 30 pg/ml of streptavidin acceptor beads and 30 µg/ml of Nickel chelate donor beads.
6. Use MutiDrop Combi to dispense 2×PRE-MIX B into ARP, 5 µl/well. Shake briefly on Combi and incubate 60 min at RT.
7. Read on EnVision (Ex: 680 nm; Em1: 615 nm).
8. Data is processed using Dotmatics. Curves are fit using a 4 parameter non-linear fit to determine the EC50 value for formation of the ternary complex.

Figure 12:
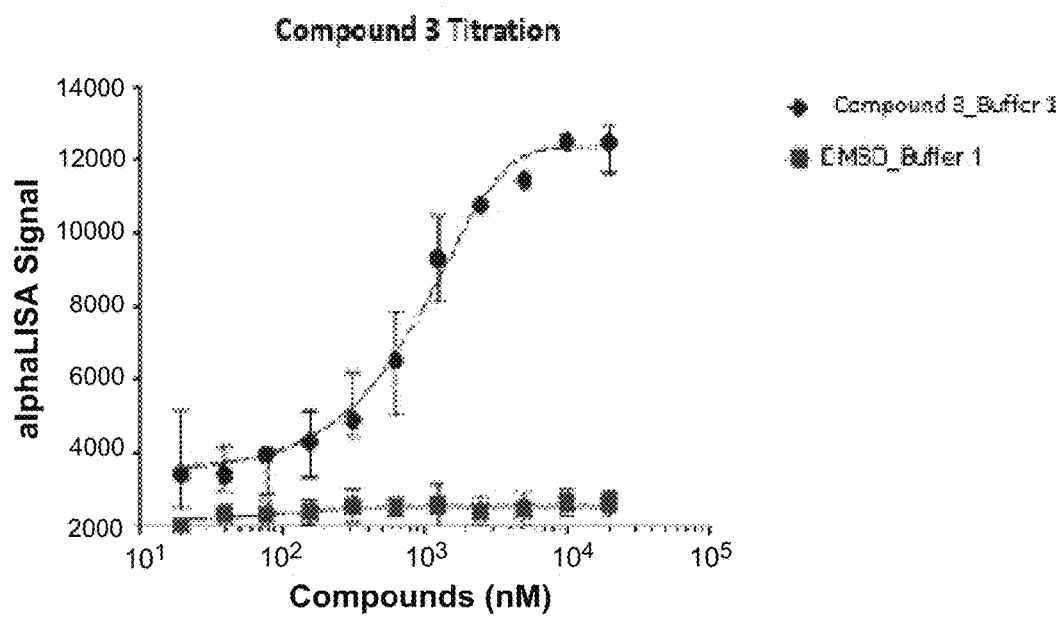
FIG. 12 is an image illustrating the binding curve of W21487 dependent complex formation of CYPA-W21487-KRAS$_{G12C\text{-}GTP}$ ternary complex.

Results: The binding curve (FIG. 12) demonstrates Compound 3 dependent complex formation of CYPA-Compound 3-KRAS$_{G12C\text{-}GTP}$ ternary complex, with a calculated EC50 value of 0.99 µM.

Example 8: Determination of Complex Formation by Isothermal Titration Calorimetry Isothermal Titration Calorimetry (ITC) is an established biophysical technique used to directly measure the heat change associated with the binary interaction of two proteins or protein to a ligand. Measurement of the heat change allows accurate determination of association constants ($K_a$), reaction stoichiometry (N), and the change in binding enthalpy (ΔH). Gibbs energy changes (ΔG) and entropy changes (ΔS) can also be determined using the relationship: ΔG=-RTlnK$_a$=ΔH-TΔS (where R is the gas constant and T is the absolute temperature). In this example, the method is used to measure binding (e.g., non-covalent or covalent binding) of a compound or conjugate of the invention to a presenter protein.
Determination of Kinetics and Thermodynamics of Binding Between FKBP12-Compound 1 and CEP250 by ITC Reagents: Compound 1 and Compound 2 in 100% DMSO (in-house), Protein Buffer (10 mM HEPES, pH 7.5, 75 mM NaCl, 0.5 mM TCEP), assay buffer (protein buffer+1% DMSO), FKBP12 (in-house), CEP250$_{29.4}$ (in-house, residues 1982-2231) and CEP250$_{11.4}$ (in-house, residues 2134-2231).

Equipment: MicroCal™ ITC$_{200}$ (GE Healthcare). Instrument parameters are shown in Table 6.

TABLE 6

| Isothermal Titration Calorimetry instrument parameters | |
|---|---|
| | MicroCal ™ ITC$_{200}$ (GE Healthcare) |
| Experimental device | |
| Sample cell volume (µl) | 270 |
| Injector volume (µl) | 40 |
| Experimental parameters | |
| Total number of Injections | 19 |
| Cell Temperature (° C.) | 25 |
| Reference Power (µCal/s) | 5 |
| Initial Delay (s) | 200 |
| Stirring Speed (rpm) | 750 |
| Injection parameters | |
| Volume (µl) | 2 |
| Duration (s) | 4 |
| Spacing (s) | 170-200 |
| Filter Period (s) | 5 |
| Feedback Mode/Gain | High |

Experimental Protocol: FKBP12 stock solution is diluted to 10 µM in assay buffer (1% DMSO final). Compound is added to FKBP12 to 20 µM (1% DMSO final), and binary complex is filled into the reaction cell of the ITC device after 5-10 min pre-incubation time. CEP250 protein stocks are diluted to 50 µM in assay buffer and supplemented with 20

µM compound (1% DMSO final) before being filled into the injection syringe. A control experiment in the absence of compound is also run to determine the heat associated with operational artifacts and the dilution of titrant as it is injected from the syringe into the reaction cell. More detailed experimental parameters are shown in Table 7.

TABLE 7

Final protein and ligand concentrations

| Experiment | Cell content | Syringe content | Ligand | DMSO conc. (%) |
|---|---|---|---|---|
| 3 | FKBP12, 10 µM | CEP250$_{29.2}$, 50 µM | None | 1.0 |
| 4 | FKBP12, 10 µM | CEP250$_{11.4}$, 50 µM | None | 1.0 |
| 5 | FKBP12, 10 µM | CEP250$_{29.2}$, 118 µM | Compound 1b, 20 µM | 1.0 |
| 6 | FKBP12, 10 µM | CEP250$_{29.2}$, 118 µM | Compound 2, 20 µM | 1.0 |
| 7 | FKBP12, 10 µM | CEP250$_{11.4}$, 68 µM | Compound 1b, 20 µM | 1.0 |
| 8 | FKBP12, 10 µM | CEP250$_{11.4}$, 68 µM | Compound 2, 20 µM | 1.0 |

Data Fitting: Data were fitted with the Origin ITC200 software according to the following procedure:
1) Read raw data
2) In "mRawITC": adjust integration peaks and baseline, integrate all peaks
3) In "Delta H"—data control: remove bad data (injection #1 and other artifacts), subtract straight line (background subtraction)
4) In "Delta H"—model fitting: select one set of sites model, perform fitting with Levenberg-Marquardt algorithm until Chi Square is not reduced further, finish with "done" (parameters N, $K_a$ and $\Delta H$ are calculated based on fitting)

Results:
ITC measurements for the binding of FKBP12-Compound 1 and FKBP12-Compound 2 binary complexes to CEP250 are summarized in Table 8 and FIG. 13. Overall, the data for FKBP12-Compound 1 and FKBP12-Compound 2 binary complexes binding to CEP250$_{11.4}$ and CEP250$_{29.4}$ show similar interaction parameters. $K_d$ values were similar for all combinations. All interactions show an almost identical thermodynamic profile in which binding is characterized by a purely enthalpic binding mode (−T*ΔS term is positive and does not contribute to the Gibbs free energy). Binding stoichiometries for all interactions were N=0.5-0.6 and support a 1:2 binding ratio for 1 CEP250 homodimer binding to 2 FKBP12 molecules, as evidenced in the crystal structure of CEP250$_{11.4}$/Compound 1/FKBP12.

Example 9: Determination of Kinetics of Binding Between Conjugates and Proteins by Surface Plasmon Resonance Surface Plasmon Resonance (SPR) is a biophysical technique used to measure the kinetics associated with the binary interaction of either two proteins or a protein to a ligand. Typically, one component of the binary interacting pair is immobilized on a flow cell of an activated sensor chip via a fusion tag. Increasing concentrations of the second component (the analyte) are then injected over the active surface for a fixed time. An increase in SPR signal (expressed in resonance units, RU) during the association phase and decrease in SPR signal during the dissociation phase is indicative of an interaction and can be fit to a binding model to determine associated $K_D$, $K_a$, $K_d$ values. In this example, the method is used to measure kinetics for the binding of a conjugate of the invention to a presenter protein, in which either (i) the conjugate is immobilized on the chip via fusion tag and a presenter protein is injected over the surface, or (ii) a presenter protein is immobilized on the chip via a fusion tag and a conjugate is injected over the surface.

Determination of Kinetics of Binding Between FKBP12-Compound 1 and CEP250 by SPR This protocol utilizes Surface Plasmon Resonance (SPR) as a method to determine kinetics ($K_D$, $K_a$, $K_d$) for the binding of CEP250 (analyte) to immobilized FKBP12-Compound 1 binary complex (ligand).

Reagents: Compound 1 in 100% DMSO (in-house), 10×HBS-P+ buffer (GE Healthcare BR-1006-71), Assay buffer (1×HBS-P+ buffer, 1% DMSO, 1 µM Compound 1), 12×HIS tagged FKBP12 (in-house), CEP250$_{29.2}$ (residues 1982-2231) and CEP250$_{11.4}$ (residues 2134-2231) (in-house).

Equipment: BIACORE™ X100 (GE Healthcare)
Supplies: NTA Sensor chip (GE Healthcare BR-1000-34)

TABLE 8

Determination of FKBP12-Compound 1-CEP250 ternary complex formation by ITC

| Experiment | T (K) | N | Kd (µM)* | ΔH (kJ * mol$^{-1}$)** | −T * ΔS (kJ * mol$^{-1}$)*** | ΔH (kJ * mol-1)**** |
|---|---|---|---|---|---|---|
| 3 | 298 | N.D. | N.D. | N.D. | N.D. | N.D. |
| 4 | 298 | N.D. | N.D. | N.D. | N.D. | N.D. |
| 5 | 298 | 0.50 | 0.19 | −52.21 | 13.80 | −38.41 |
| 6 | 298 | 0.57 | 0.36 | −58.48 | 21.73 | −36.74 |
| 7 | 298 | 0.56 | 0.07 | −49.37 | 8.62 | −40.75 |
| 8 | 298 | 0.54 | 0.08 | −47.78 | 7.41 | −40.36 |

*$K_d$ (calculated from $K_a$ = 1/$K_d$
**ΔH
***T * ΔS (calculated from − TΔS = ΔG − ΔH)
****ΔG = −RT ln $K_a$ = RT ln $K_d$ Experimental Protocol: Experiments are performed at 25° C. Stock solution of 12×HIS tagged FKBP12 is diluted to 100 nM in assay buffer containing 1 µM Compound 1 (1% DMSO final). Approximately 200-400 RU of FKBP12 is immobilized on one of two flow cells of an activated NTA chip. The second flow cell is not activated as a reference for non-specific interaction of the analyte to the sensor chip. Various concentrations of CEP250 (1 nM-1 µM range), serially diluted into the same assay buffer containing 1 µM Compound 1 (1% DMSO final), are injected onto the FKBP12 surface and reference surface at a flow rate of 10 µl/min. The surface is regenerated between analyte injections with 350 mM EDTA.

Data Fitting: The BiaEvaluation software program is used for data fitting. All data is reference subtracted against both the reference flow cell and a buffer injection. For kinetic analyses, data is locally fit to a 1:1 interaction model.

Figure 14:
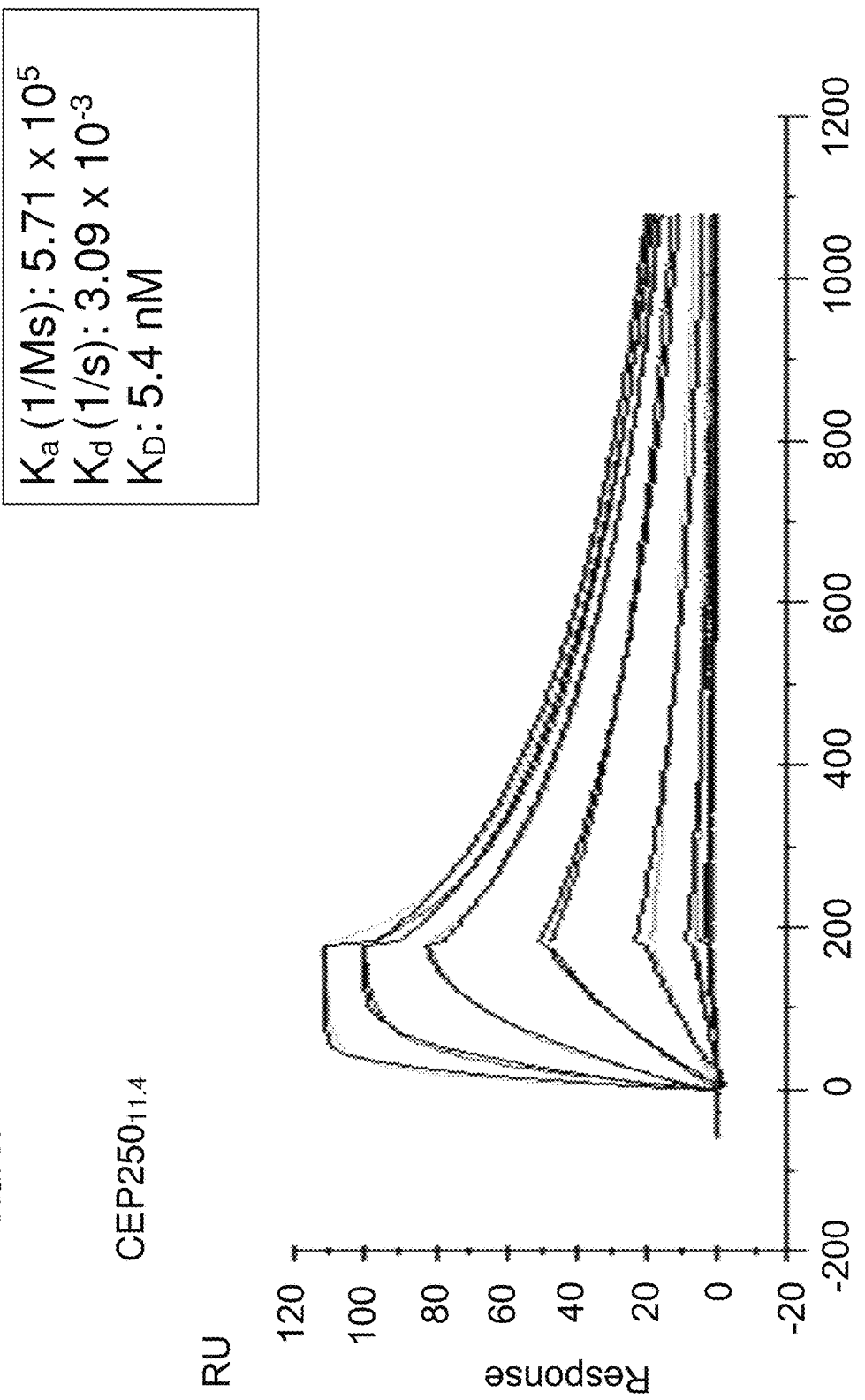
FIG. 14 is an image illustrating SPR sensorgrams for the binding of FKBP12/Compound 1 to CEP250$_{11.4}$ and CEP250$_{29.2}$.
Figure 14:
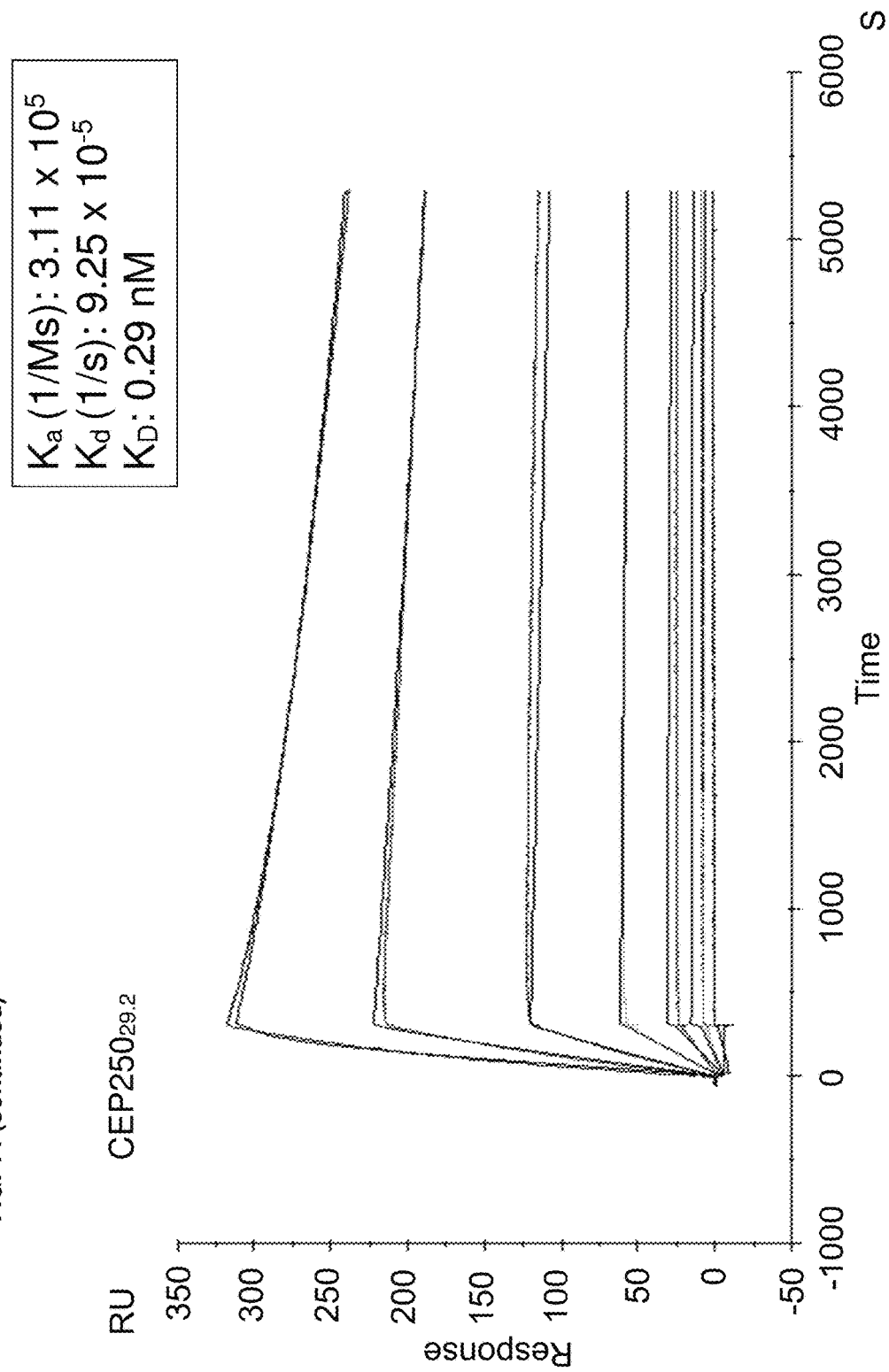

Results: SPR sensorgrams and are shown in FIG. 14. Dissociation constants ($K_D$) of 5.4 nM and 0.29 nM were determined for the binding of FKBP12/Compound 1 to CEP250$_{11.4}$ and CEP250$_{29.2}$, respectively.

Example 10: Determination of Kinetics of Binding Between Conjugates and Proteins by Biolayer Interferometry Biolayer Inferometry (BLI) is a biophysical technique used to measure the kinetics associated with the binary interaction of either two proteins or a protein to a ligand. Typically, one component of the binary interacting pair is immobilized on a biosensor tip via a fusion tag. Increasing concentrations of the second component (the analyte) are then injected over the biosensor tip for a fixed time. An increase in BLI signal (expressed in optical thickness, nm) during the association phase and decrease in BLI signal during the dissociation phase is indicative of an interaction and can be fit to a binding model to determine associated $K_D$, $K_a$, $K_d$ values. In this example, the method is used to measure kinetics for the binding of a conjugate of the invention to a presenter protein, in which either (i) the conjugate is immobilized on the tip via fusion tag and a presenter protein is injected over the surface, or (ii) a presenter protein is immobilized on the tip via a fusion tag and a conjugate is injected over the surface.

Determination of Kinetics of Binding Between CYPA-Compound 3 and KRAS$_{G12C-GTP}$ by BLI This protocol utilizes Biolayer Interferometry (BLI) as a method to determine the dissociation constant ($K_D$) for the binding of KRAS$_{G12C-GTP}$ (analyte) to immobilized CYPA-Compound 3 binary complex (ligand).

Reagents: Compound 3 in 100% DMSO (in-house), ForteBio Kinetic Buffer (FortéBio Inc., Menlo Park, Calif.), Assay Buffer (Kinetic Buffer, 1% DMSO, 2 µM Compound 3), Avi-tagged CYPA (in-house), KRAS$_{G12C-GTP}$ (residues 1-169) (in-house).

Equipment: Octet Red 96 instrument (FortéBio Inc., Menlo Park, Calif.)

Supplies: Streptavidin (SA) biosensors (FortéBio)

Experimental Protocol: Streptavidin (SA) biosensors were coated in a solution containing 10 µM Avi-CYPA protein at 25° C. to a loading signal of 0.6 nm. The loading of the protein showed stability over time and an absence of baseline drift. The formation of the ternary complex was evaluated in dose-response experiments with KRAS$_{G12C-GTP}$ protein concentrations starting from 200 µM in a 1:2 dilution series. For negative control, sensors coated with Avi-CYPA protein were dipped into wells containing only the screening buffer (supplemented with 2 µM Compound 3). Corrected binding response sensograms were recorded and analyzed.

Data Fitting: Analysis on the FortéBio Octet RED instrument was performed using the FortéBio software. The analysis accounts for non-specific binding, background, and signal drift and minimizes well based and sensor variability. Dose-dependent formation of the ternary complex was observed and the corresponding equilibrium dissociation constants ($K_D$) were determined.

Figure 15:
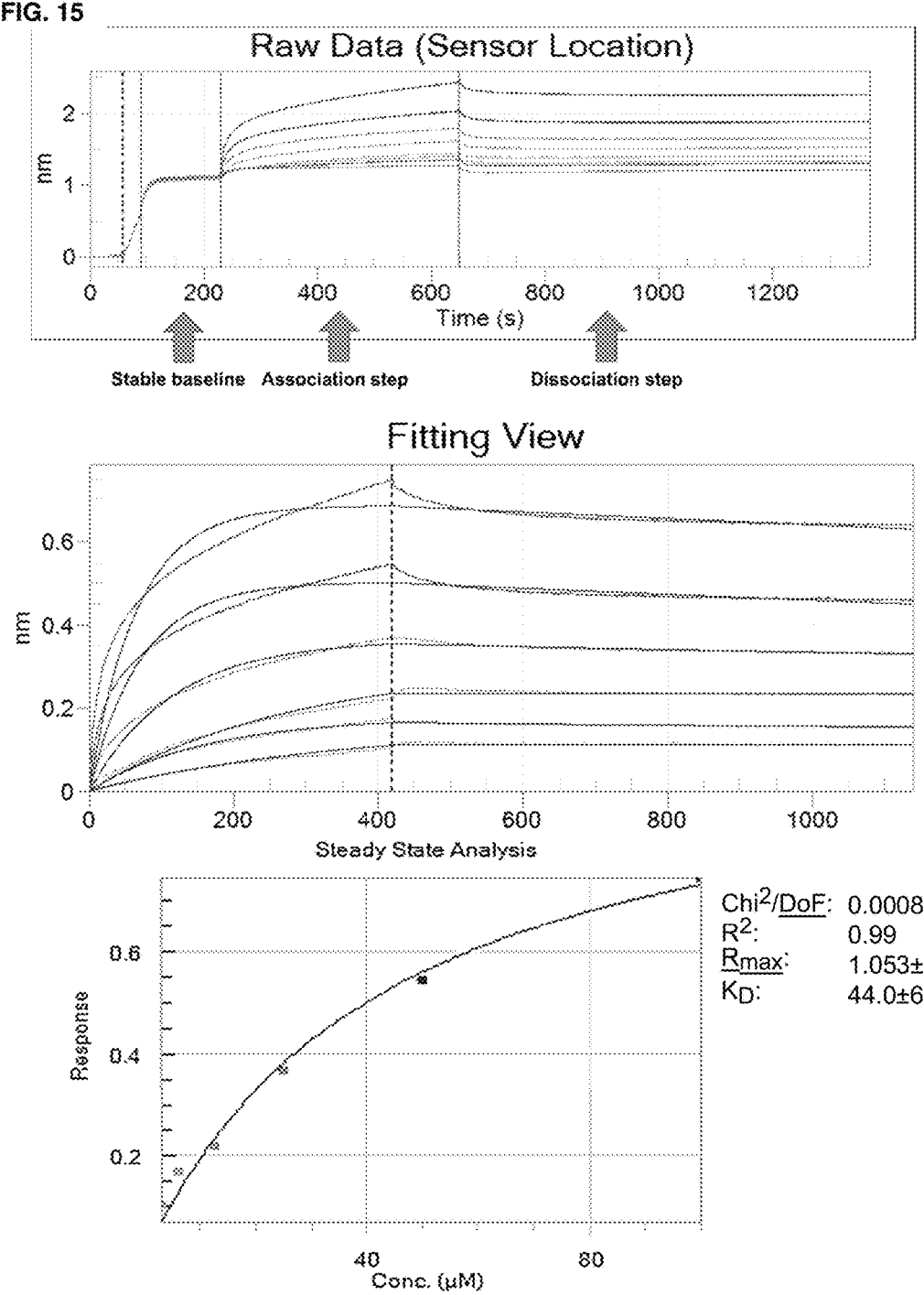
FIG. 15 is an image illustrating sensogram and steady state fitting curves for the binding of CYPA/Compound 3 to KRAS$_{G12C\text{-}GTP}$.

Results: Sensogram and steady state fitting curves are shown in FIG. 15. A dissociation constant ($K_D$) of 44 µM was determined for the binding of CYPA/Compound 3 to KRAS$_{G12C-GTP}$.

Example 11: Proteomic Identification of FKBP12 Bound Target Proteins for Cross-Linking Reagents Reagents: Compound in 100% DMSO (in-house), N-terminal biotin-FKBP12 (in-house), HEK293T cell lysate (in-house).

Experimental Protocol: HEK293T cell lysate was prepared using a lysis buffer consisting of 40 mM HEPES, pH 7.3, 120 mM NaCl, 2 mM MgCl$_2$, 2 mM CaCl$_2$, 0.5% octyl-b-glucoside, and EDTA free protease inhibitor cocktail (Roche) using sonication (4, 10 second pulses at 20% power) on ice. The lysate was first cleared via centrifugation and the resulting supernatant is passed through a 0.2 mm syringe filter on ice. N-terminal biotin labeled FKBP12 was added to 500 ml of the lysate to a final concentration of 4 mM, mixed via pipetting, and then compound was added to a final concentration of 10 mM with the reaction being mixed via pipetting. 60 mL of 50% slurry agarose-Streptavidin resin (pre-equilibrated in the lysis buffer) was added and the reaction is allowed to proceed at 4° C. with gentle rocking for 1 hour. After incubation, the resin was gently pelleted, washed 4 times with 1 mL of lysis buffer on ice via addition, centrifugation, and aspiration and then washed another 4 times with 1 mL of lysis buffer without detergent in the same physical manner. Retained proteins were eluted from the resin using 8M Urea, pH 8.0 in HEPES buffer, diluted to 7M Urea with 100 mM HEPES, pH 8.0 and Endoproteinase Lys-C added for protein digestion at 37° C. for 2 hours. Next, the sample was diluted to 0.8M Urea using 100 mM HEPES, pH8.0, Trypsin was added, and the sample digested for an additional 16 hours at 37° C. After digestion was complete, the sample was prepared for LC-MS/MS analysis using a C18 SPE filter onto which the sample was loaded, washed, eluted, desiccated in a speed-vac, and finally suspended in 10 ml of 5% acetonitrile, 5% formic acid buffer for LC-MS/MS analysis. LC-MS/MS analysis was performed on a Thermo-Fisher LTQ-Velos-Pro OrbiTrap mass spectrometer using a top 20 data dependent acquisition method and 8-35% acetonitrile gradient for the HPLC. Peptide sequences were assigned using the Sequest algorithm and identified proteins are compared to control samples (DMSO only) in order to identify candidate target proteins.

Results: Using the above protocol, >100 target proteins have been identified as being capable of binding to a presenter protein in the presence of a cross-linking compound. The identified target proteins include kinases, phosphatases, ubiquitin ligases, DNA binding proteins, heat shock proteins, DNA helicases, GTPase activating proteins, nucleotide binding proteins, and miscellaneous protein binding proteins.

Example 12: Determination of Binding Between Conjugates and Proteins by Fluorescence Polarization The technique of fluorescence polarization (FP) is based on the observation that when a fluorescently labeled molecule is excited by polarized light, it emits light with a degree of polarization that is inversely proportional to the rate of molecular rotation. Small molecules rotate quickly during the excited state, and upon emission, have low polarization values. Large complexes, formed by binding of a labeled molecule to a second molecule, rotate little during the excited state, and therefore have high polarization values. This property of fluorescence can be used to measure the interaction of a labeled ligand with a larger protein and provides a basis for direct and competition binding assays. In this example, the method is used to measure the binding of compound or conjugate of the invention to the presenter protein and establish ternary complex formation with a target protein.

Determination of CypA:C3DS:KRAS Complex Formation by FP

Reagents: C3DS in 100% DMSO (in-house), Protein Buffer (12.5 mM HEPES pH=7.4, 1 mM $MgCl_2$), assay buffer (25 mM HEPES, pH 7.3, 0.002% Tween 20, 0.1% BSA, 10 mM NaCl, 1 mM $MgCl_2$), CYPA (in-house), Mant-GMP-PNP loaded KRAS (1-169 residues).

Equipment: SpectraMax

Experimental Protocol: KRAS stock solution is loaded to final concentration of 0.8 µM in assay buffer (1% DMSO final). Compound (C3DS) is added to a final concentration of 10 µM and the reaction mixture is dispensed to a 384 well Costar black plate. CYPA is serially diluted into the wells of the plate and allowed to incubate for 15 mins at room temperature. A control experiment in the absence of compound is also run to determine the association of the CYPA to KRAS in the absence of compound. The reaction mixtures are excited at 355 nm and the emission signal is recorded at 455 nm. The signals are measured at perpendicular and parallel planes and the polarization is recorded using the following equation.

FP(polarization units×10^−3)=Signal(Parallel)−Signal(Perpendicular)/[Signal(Parallel)+Signal(Perpendicular)]

Figure 16:
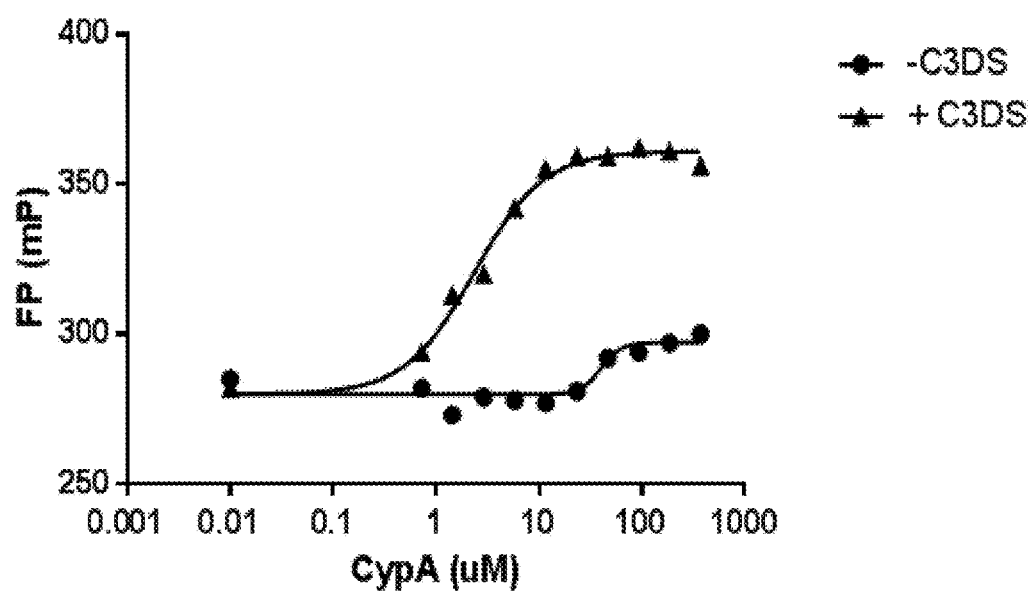
FIG. 16 is an image illustrating fluorescence polarization curves for CypA:C3DS:KRAS complex formation.

Results: A representative curve and is shown in FIG. 16 and a table listing the EC50 (concentration require to enhance the FP signal of the KRAS by 50%) is listed below. The curves were fit to a four-parameter equation and the EC50s obtained indicate the effect of the ligand C3DS towards enhancing the binding between CYPA and KRAS.

|  | CypA:Kras | CypA:C3DS:Kras |
|---|---|---|
| EC50 | 30 µM | 2.3 µM |

Example 13: Determination of Binding Between Conjugates and Proteins by Nuclear Magnetic Resonance Nuclear Magnetic Resonance (NMR) spectroscopy is a technique used to solve three-dimensional structures and study the dynamics of proteins and protein-ligand complexes. In addition, it can be used to identify the ligand binding site in protein-ligand interaction. Out of several available NMR approaches, protein structure based ligand screening (highly sensitive 2D $^1H$-$^{15}N$ TROSY-HSQC spectrum) and identification of critical residues involved in ligand (drug) binding is the most sensitive method for such studies. Addition of sequentially increasing ligand concentration into protein's NMR sample and collection of 2D $^1H$-$^{15}N$ TROSY-HSQC provides atomic level highly resolved residue perturbation information, called chemical shift perturbation (CSP), that directly provides more accurate information on identification of ligand binding site not possible by any other biophysical techniques available. With this approach weak, intermediate, and strong affinity of ligand binding to a protein or binary protein complex can be studied, and this information can be directly linked to existing structural, dynamic, and kinetic information. In this example, the method is used to demonstrate binding (e.g. non-covalent or covalent) of a compound (drug) or conjugate of the invention to a presenter protein.

Determination of KRAS(G12C)-Cyclophilin-Compound 3 Binding in Ternary Complex by Solution NMR Spectroscopy Reagents: Compound 3 in 100% DMSO (in-house), Protein Buffer (50 mM TRIS-$d_{11}$, 50 mM NaCl, pH 7.0, 1 mM TCEP-$d_{16}$, 1 mM $MgCl_2$), Additives in NMR sample of KRAS (100 µM DSS in 93% $H_2O$ and 7% $D_2O$), assay buffer (protein buffer+increasing equivalents of drug in DMSO (≤5%)), GMP-$^{15}N$-KRAS(G12C)-16 (N-His, residues 1-169, in-house), unlabeled (UL) Cyclophilin (CYPA; residues 1-165) (in-house).

Equipment: Bruker Avance 800 MHz Spectrometer equipped with 5 mm CPTCI $^1H$-$^{13}C/^{15}N/D$ Z-GRD Z44909/0026 cryoprobe (Bruker). High precision 5 mm NMR tubes are used in these experiments.

NMR Data Processing and Analysis: Linux computers running Topspin v3.1 and NMRPipe/NMRDraw for processing, and CCPNMR "analysis" program for data analysis.

Experimental Protocol: GMP-$^{15}N$-KRAS(G12C)-16 stock solution of 0.72 mM in protein buffer was used to prepare 0.18 mM NMR sample in 600 µl (including NMR additives). DSS was used as internal standard ($^1H$ peak at 0.0 ppm) for chemical shift referencing. 2D $^1H$-$^{15}N$ TROSY-HSQC spectrum of $^{15}N$ KRAS was collected (data size 2048×128). One equivalent (0.18 mM) of CYPA in protein buffer was added (from stock solution of 0.4 mM) into NMR sample and agitated for 10 minutes. Final NMR sample volume was maintained to 600 µl. 2D $^1H$-$^{15}N$ TROSY-HSQC spectrum of binary complex ($^{15}N$-KRAS+UL-CYPA) was collected (data size 2048×128) keeping other acquisition parameters the same (only KRAS $^1H$-$^{15}N$ correlation crosspeaks are visible in the spectrum). A stock solution of 20 mM Compound 3 in 100% DMSO was used for NMR titrations. Compound 3 was sequentially added into NMR sample to obtain its 0.5, 1.0, 2.5, and 5.0 equivalents (to that of 15N-KRAS concentration) in the NMR sample of binary complex ($^{15}N$-KRAS+UL-CYPA). At each stages sample volume of 600 µl was maintained while keeping the acquisition parameters the same. At each stages of Compound 3 addition, 2D $^1H$-$^{15}N$ TROSY-HSQC spectrum was acquired to investigate chemical shift perturbation (CSP) of KRAS residues. All spectra were superimposed to each other. Effective CSP at each Compound 3 titration point is determined using the difference of chemical shifts of each residue of KRAS in ternary complex (KRAS+CYPA+Compound 3) versus the binary complex (KRAS+CYPA). Subsequently, weighted average chemical shift ($\Delta\delta_{weighted}$) of each KRAS residue are determined using the below formula:

$$\Delta\delta_{weighted}=[(\Delta^1H)^2+(\Delta^{15}N/5)^2]^{1/2}$$

Residues eliciting $\Delta\delta_{weighted}$ greater than one standard deviation from overall average are considered significantly perturbed and used in the binding site mapping. In separate titration experiments, we have collected 2D $^1$H-$^{15}$N TROSY-HSQC spectra on binary complex (KRAS+CYPA) by sequentially adding DMSO equivalents (to meet equivalent solvent concentration as in above experiment) to subtract contribution from DMSO addition. In second control experiment, we have collected series of 2D $^1$H-$^{15}$N TROSY-HSQC spectra of 15N-KRAS titrated with Compound 3 at different equivalents (in absence of CYPA).

The effective CSP is tabulated and analyzed. Drug binding residues of KRAS (in presence of CYPA) is mapped onto the protein surface. Dissociation constant, $K_D$, is determined.

Figure 17A:
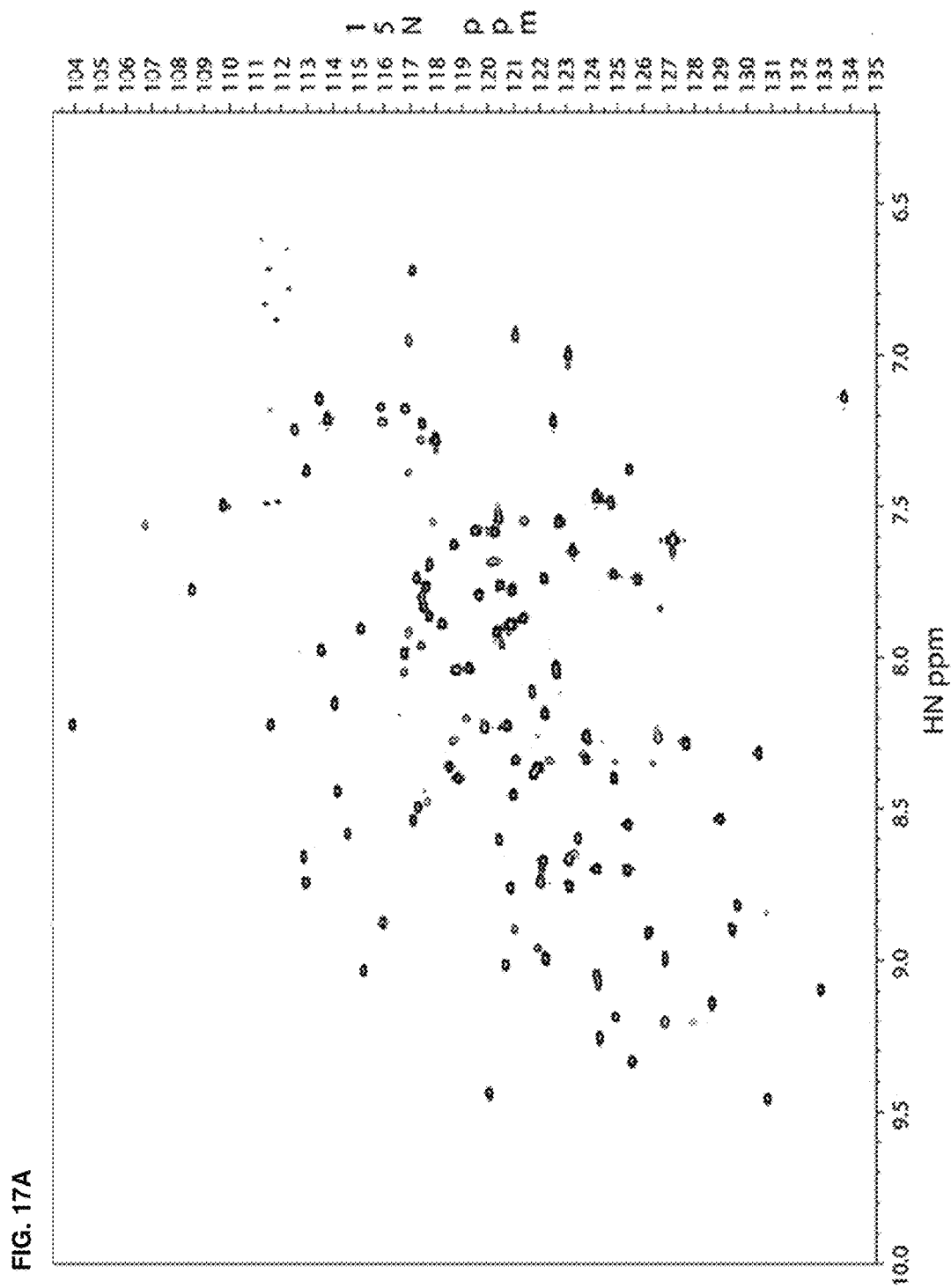
Figure 17B:
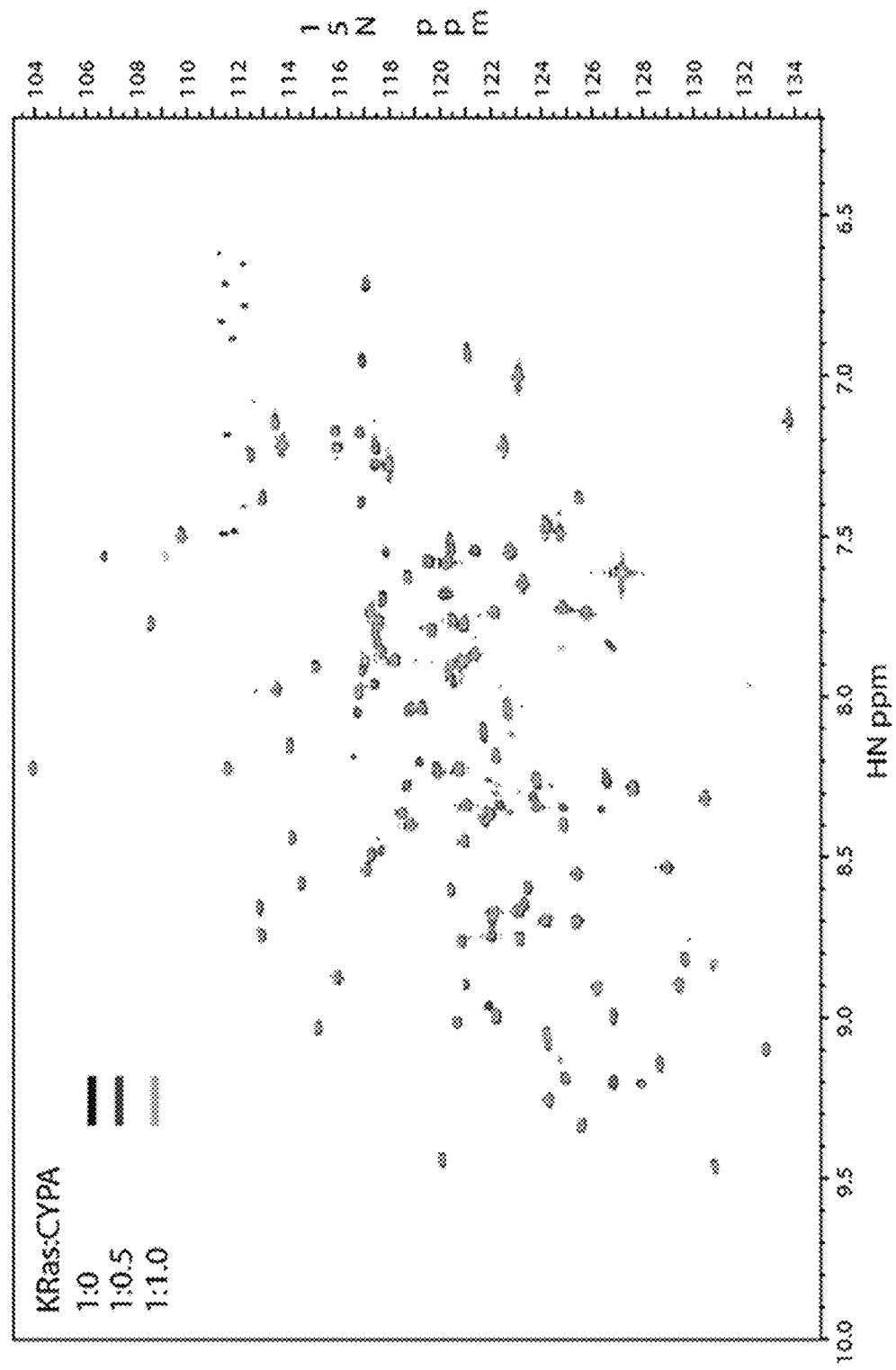

Experimental and Processing Parameters:
Spectrum data size: 2048 (1H dimension)×128 (15N-dimension)
Number of scans: 4
Temperature: 298 K
Quadrature Detection Mode: DQD (1H) and Echo-AntiEcho (15N)
Data sizes were extended by applying forward-backward linear prediction within the indirect dimension.
Data sets were extrapolated by zero filling once in each dimension prior to Fourier transformation.
Results: 2D 1H-15N TROSY-HSQC spectrum of KRAS$_{G12C\text{-}GTP}$ is shown in FIG. 17A. Adding a stoichiometric amount of CYPA has no effect on KRAS amide backbone crosspeaks (FIG. 17B), indicating that KRAS and CYPA do not interact directly. Titration of W21487 into a 1:1 sample of CYPA:KRAS elicits distinct chemical shifts (FIG. 17C), indicative of a direct interaction with KRAS.

Example 14. Determination of Binding Between Conjugates and Proteins by Microscale Thermophoresis Microscale Thermophoresis (MST) is a technique for characterization of biomolecular interactions by correlating any changes in the molecular properties of the molecule such as size, conformation to its mobility in a directed temperature gradient. The generation of the gradient is induced by an infrared laser. The movement of the biomolecule is frequently characterized by labeling the molecule using covalently attached fluorophores or even intrinsic fluorescence. In this example, the method is used to measure the binding of compound or conjugate of the invention to the presenter protein and establish ternary complex formation with a target protein, in which either (i) the conjugate is labelled with a fluorophore and a presenter protein is titrated in, or (ii) a presenter protein is labelled with a fluorophore and a conjugate is titrated in.

Example 15. Determination of Binding Between Conjugates and Proteins by Second Harmonic Generation Technology Second Harmonic Generation (SHG) is an optical phenomenon that can be used to measure conformational changes in aqueous solution in real time. SHG signal intensity is sensitive to average angular orientation of dye labeled to a protein tethered to a surface and magnitude of signal change directly correlates to amount of angular change. Different conformations can be classified by magnitude of signal change upon binding, signal relative to baseline (more vertical orientations relative to surface produce positive signal changes and vice versa) and kinetics. In this example, the method is used to measure the binding of compound or conjugate of the invention to the presenter protein and establish ternary complex formation with a target protein, in which either (i) a dye labelled conjugate is immobilized on the surface via a fusion tag and a presenter protein is injected over the surface, or (ii) a dye labelled presenter protein is immobilized on the surface via a fusion tag and a conjugate is injected over the surface.

Example 16. Determination of Binding Between Conjugates and Proteins by Differential Scanning Fluorimetry Differential Scanning Fluorimetry (DSF) is a solution based biophysical technique used to measure the melting temperature ($T_m$) of a protein. In a typical experiment, protein of interest is subject to increasing heat (typically from 4° C.–95° C.) in the presence of a fluorescent dye (e.g. SYPRO orange). Fluorescent intensities are plotted as a function of temperature and the $T_m$ is calculated from the negative derivative minimum of the fluorescence signal. For a target protein, the thermal shift ($\Delta T_m$) in the presence of a small molecule can be measured to assess whether the small molecule binds to and stabilizes the protein. In this example, the method is used to measure the thermal shift (e.g., non-covalent or covalent binding) of a compound or conjugate of the invention to a presenter protein, in which either (i) the conjugate is labelled with a fluorescent dye and a presenter protein is titrated in, or (ii) a presenter protein is labelled with a fluorescent dye and a conjugate is titrated in.

Example 17. Determination of Binding Between Conjugates and Proteins by NanoDSF NanoDSF is an advanced DSF method for measuring the $T_m$ of a protein using intrinsic tryptophan or tyrosine fluorescence. In a typical experiment, protein of interest is subject to increasing heat (typically from 4° C.–95° C.) and fluorescent intensities of intrinsic tryptophan or tyrosine residues are monitored as a function of temperature. $T_m$ can be calculated from the changes in tryptophan fluorescence intensity, or from the ratio of tryptophan emission at 330 and 350 nm, which describes the shift of tryptophan emission upon unfolding. For a target protein, $\Delta T_m$ in the presence of a small molecule can be measured to assess whether the small molecule binds to and stabilizes the protein. In this example, the method is used to measure the thermal shift (e.g., non-covalent or covalent binding) of a compound or conjugate of the invention to a presenter protein, in which either (i) the fluorescence of the conjugate is measured and a presenter protein is titrated in, or (ii) the fluorescence of a presenter protein is monitored and a conjugate is titrated in.

Example 18. Determination of Complex Formation by Differential Light Scattering Dynamic light scattering (DLS) is an established biophysics method used to measures time-dependent fluctuations in the scattering intensity arising from particles undergoing random Brownian motion. Diffusion coefficient and particle size information can be obtained from the analysis of these fluctuations. More specifically, the method provides the ability to measure size characteristics including radius and molecular weight of proteins in aqueous solution. In this example, the method is used to measure change in radius or molecular weight in either (i) the presenter protein upon binding of conjugate of the invention or (ii) the conjugate of the invention upon binding to a presenter protein.

Example 19. Determination of Binding Between Conjugates and Proteins by Sonic Wave Acoustic Technology Surface Acoustic Wave (SAW) technology is a biophysical method used for the real-time detection of binding-induced conformational changes through monitoring the shift in the phase of surface acoustic waves that travel along the biosensor. It can be used to measure the kinetics associated with the binary interaction of either two proteins or a protein to a ligand. Typically, one component of the binary interacting pair is immobilized on the biosensor via a fusion tag. Increasing concentrations of the second component (the analyte) are then injected over the biosensor for a fixed time. An increase in signal (measured either through a change in wave phase or amplitude) during the association phase and decrease in signal during the dissociation phase is indicative of an interaction and can be fit to a binding model to determine associated $K_D$, $K_a$, $K_d$ values. In this example, the method is used to measure kinetics for the binding of a conjugate of the invention to a presenter protein, in which either (i) the conjugate is immobilized on the biosensor chip via fusion tag and a presenter protein is injected over the surface, or (ii) a presenter protein.

Example 20: Determination of Complex Formation by Small-Angle X-Ray Scattering

Small-Angle X-Ray Scattering (SAXS) is a solution based method used to determine the structure of a protein in terms of average particle size and shape. It is capable of delivering structural information in the resolution range between 1 and 25 nm, and of repeat distances in partially ordered systems of up to 150 nm in size. Ultra small-angle scattering (USAS) can resolve even larger dimensions. In a typical scattering experiment, a solution of protein or protein complex are exposed to X-rays (with wavelength λ typically around 0.15 nm). The scattered intensity i(s) is recorded as a function of momentum transfer s ($s=4\pi \sin \theta/\lambda$, where $2\theta$ is the angle between the incident and scattered radiation). From the intensity of the solution the scattering from only the solvent is subtracted. An X-ray scattering curve (intensity versus scattering angle) is then used to create a low-resolution model of a protein or protein complex. In this example, the method is used to identify existence of a ternary complex (e.g., non-covalent or covalent binding) of a compound or conjugate of the invention to a presenter protein.

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polynucleotide or protein encoded thereby; any method of production; any method of use) can be excluded from any one or more claims, for any reason, whether or not related to the existence of prior art.

What is claimed is:

1. A compound having the structure:

A-L-B wherein A has the structure of Formula IIa:

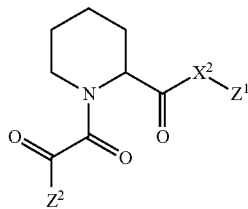

Formula IIa wherein $Z^1$ and $Z^2$ are each, independently, optionally substituted $C_1$-$C_6$ alkyl, optionally substituted $C_1$-$C_6$ heteroalkyl; and $Z^2$ includes a point of attachment to the L;

$X^2$ is absent, $CH_2$, O, S, SO, $SO_2$, or $NR^4$;

each $R^4$ is, independently, hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl;

L is a linker having the structure:

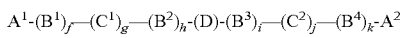

wherein $A^1$ is a bond between the linker and A; $A^2$ is a bond between B and the linker; $B^1$, $B^2$, $B^3$, and $B^4$ each, independently, is selected from optionally substituted $C_1$-$C_2$ alkyl, optionally substituted $C_1$-$C_3$ heteroalkyl, O, S, and $NR^N$; $R^N$ is hydrogen, optionally substituted $C_1$-$C_4$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; $C^1$ and $C^2$ are each, independently, selected from carbonyl, thiocarbonyl, sulphonyl, or phosphoryl; f, g, h, i, j, and k are each, independently, 0 or 1; and D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$13 $(C^1)_g$—$(B^2)_h$— to —$(B^3)_i$—$(C^2)_j$—$(B^4)_k$-$A^2$; and B comprises a cross-linking group, wherein the cross-linking group is a maleimide, vinyl sulfone, isocyanate, isothiocyanate, sulfonyl chloride, acid anhydride, acyl-azide, imidoester, haloheteroaryl, diazo, carbodiimide, hydrazide, or alkoxyamine, or a salt thereof.

2. The compound of claim 1, wherein the cross-linking group is a maleimide or a vinyl sulfone, or a salt thereof.

* * * * *

UNITED STATES PATENT AND TRADEMARK OFFICE
CERTIFICATE OF CORRECTION

PATENT NO. : 10,466,249 B2
APPLICATION NO. : 15/974923
DATED : November 5, 2019
INVENTOR(S) : Gregory Lawrence Verdine et al.

It is certified that error appears in the above-identified patent and that said Letters Patent is hereby corrected as shown below:

In the Claims

Column 120, Line 26, In Claim 1, replace "$A^1-(B^1)_f 13\ (C^1)_g -(B^2)_h -$" with -- $A^1 -(B^1)_f-(C^1)_g -(B^2)_h -$ --.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*